(12) United States Patent
Tomonaga et al.

(10) Patent No.: US 9,365,865 B2
(45) Date of Patent: Jun. 14, 2016

(54) VECTOR UTILIZING BORNA DISEASE VIRUS AND USE THEREOF

(75) Inventors: Keizo Tomonaga, Osaka (JP); Takuji Daito, Osaka (JP); Tomoyuki Honda, Tokyo (JP)

(73) Assignee: KYOTO UNIVERSITY, Kyoto (JP)

( * ) Notice: Subject to any disclaimer, the term of this patent is extended or adjusted under 35 U.S.C. 154(b) by 540 days.

(21) Appl. No.: 13/258,698

(22) PCT Filed: Mar. 17, 2010

(86) PCT No.: PCT/JP2010/054600
§ 371 (c)(1),
(2), (4) Date: Nov. 8, 2011

(87) PCT Pub. No.: WO2011/113647
PCT Pub. Date: Oct. 7, 2010

(65) Prior Publication Data
US 2012/0151614 A1    Jun. 14, 2012

(30) Foreign Application Priority Data

Mar. 31, 2009  (JP) ................. 2009-087608

(51) Int. Cl.
*C12N 15/00* (2006.01)
*A61K 39/12* (2006.01)
*C12N 15/86* (2006.01)
*C12N 15/11* (2006.01)

(52) U.S. Cl.
CPC ............. *C12N 15/86* (2013.01); *C12N 15/111* (2013.01); *C12N 2310/121* (2013.01); *C12N 2310/123* (2013.01); *C12N 2310/128* (2013.01); *C12N 2330/51* (2013.01); *C12N 2760/00043* (2013.01); *C12N 2760/00045* (2013.01); *C12N 2800/80* (2013.01); *C12N 2810/6072* (2013.01); *C12N 2810/6081* (2013.01)

(58) Field of Classification Search
None
See application file for complete search history.

(56) References Cited

U.S. PATENT DOCUMENTS 6,015,660 A * 1/2000 Lipkin et al. ............. 435/5

FOREIGN PATENT DOCUMENTS

JP   2010-022338       2/2010
WO   WO 9621020 A2 *  7/1996

OTHER PUBLICATIONS

Schneider et al., A Borna Disease Virus Vector for Expression of Foreign Genes in Neurons of Rodents, 2007, Journal of Virology, 81(13):7293-7296.*

(Continued)

*Primary Examiner* — Benjamin P Blumel
*Assistant Examiner* — M. Franco Salvoza
(74) *Attorney, Agent, or Firm* — Wenderoth, Lind & Ponack, L.L.P.

(57) ABSTRACT

Disclosed is a viral vector comprising
(a) a cDNA of a recombinant viral RNA
  having at least the N gene, the X gene, the P gene, and the L gene of a Borna disease virus genome in the same order as that in the Borna disease virus genome, and
  having a sequence in which a foreign gene is inserted into the untranslated region connected to the downstream of the open reading frame of the P gene,
(b) a DNA encoding a ribozyme, and
(c) a promoter sequence,
each being disposed in a position in which (b) is placed upstream and downstream of (a), and (a) and (b) are placed downstream of (c).

5 Claims, 14 Drawing Sheets

(56) References Cited

OTHER PUBLICATIONS

Fukuda et al., "Possible Mechanism of adenovirus generation from a Cloned Viral Genome Tagged with Nucleotides at Its Ends," Microbiol. Immunol. 50(8): 643-654 (2006).*
Cubitt et al., "Identification and characterization of a new intron in Borna disease virus," Journal of General Virology, 82: pp. 641-646 (2001).*
Chase et al., "Borna Disease Virus Matrix Protein Is an Integral Component of the Viral Ribonucleoprotein Complex That Does Not Interfere with Polymerase Activity," J. Virol. 81(2): pp. 743-749 (2007).*
Extended European Search Report issued Jun. 28, 2013 in corresponding European Patent Application No. 10758423.7.
Takuji Daito et al., "A Novel Borna Disease Virus Vector System That Stably Expresses Foreign Proteins from an Intercistronic Noncoding Region", Journal of Virology, vol. 85, No. 23, Dec. 1, 2011, pp. 12170-12178, XP55066984.
Patrick Schneider et al., "Biochemical and Functional Analysis of the Borna Disease Virus G Protein", Journal of Virology, vol. 71, No. 1, Jan. 1997, pp. 331-336, XP 55066997.
Réza Etessami et al., "Spread and pathogenic characteristics of a G-deficient rabies virus recombinant: an in vitro and in vivo study", Journal of General Virology, vol. 81, No. 9, 2000, pp. 2147-2153, XP 8153169.
Naoto Ito et al., "Characterization of M Gene-Deficient Rabies Virus with Advantages of Effective Immunization and Safety as a Vaccine Strain", Microbiology and Immunology, Center for Academic Publications Japan, vol. 49, No. 11, Jan. 2005, pp. 971-979, XP 8153170.
U. Schneider et al., "A Borna Disease Virus Vector for Expression of Foreign Genes in Neurons of Rodents", Journal of Virology, vol. 81, No. 13, pp. 7293-7296, Jul. 2007.
T. Daito et al., "BDV o Riyo shita RNA Virus Vector no Kaihatsu no Kokoromi", Dai 147 Kai Japanese Society of Veterinary Science Koen Yoshishu, p. 247, Mar. 1, 2009 (with English translation).
T. Daito et al., "BDV Reverse Genetics no Kakuritsu to BDV Vector no Kaihatsu ni Muketa Kento", The 56th Annual Meeting of the Japanese Society for Virology, Program Shorokushu, p. 238, Oct. 1, 2008 (with English translation).
T. Daito et al., "BDV Genome Kaihen ni Motozuita Shinki RNA Virus Vector no Juritsu", The 57th Annual Meeting of The Japanese Society for Virology, Program Shorokushu, p. 172, Oct. 1, 2009 (with English translation).
U. Schneider et al., "Genome Trimming: A Unique Strategy for Replication Control Employed by Borna Disease Virus", Proc. Natl. Acad. Sci., USA, vol. 102, No. 9, pp. 3441-3446, Mar. 1, 2005.
R. Etessami et al., "Spread and Pathogenic Characteristics of a G-Deficient Rabies Virus Recombinant: An In Vitro and In Vivo Study", Journal of General Virology, vol. 81, Pt. 9, pp. 2147-2153, 2000.
N. Ito et al., "Characterization of M Gene-Deficient Rabies Virus with Advantages of Effective Immunization and Safety as a Vaccine Strain", Microbiol. Immunol., vol. 49, No. 11, pp. 971-979, 2005.
K. Tomonaga, "Cell Nucleus and RNA Virus Mechanism of Nuclear Transport and Persistent Infection of Borna Disease Virus", Protein, Nucleic Acid and Enzyme, vol. 52, No. 10, pp. 1168-1174, 2007 (with partial English translation).
K. Tomonaga, "Borna Disease Virus Infection and Neurological Disorders", Saishin Igaku, vol. 60, No. 2, pp. 79-85, Feb. 2005 (with partial English translation).
H. Yanai et al., "Development of a Novel Borna Disease Virus Reverse Genetics System Using RNA Polymerase II Promoter and SV40 Nuclear Import Signal", Microbes and Infection 8, pp. 1522-1529, 2006.
English translation of the International Preliminary Report on Patentability issued in corresponding PCT Application No. PCT/JP2010/054600.

* cited by examiner

Fig. 8

|  | αM | GFP |
|---|---|---|
| rBDVwt | a | b |
| p/mGFP | c | d |
| 5'GFP | e | f |

Fig. 9

Recombinant BDV

Neonatal rat → 1w  2w  3w  4w → Persistent infection

Fig. 10

1. Anterior part
2. Middle part
3. Posterior part

Left brain | Right brain

Inoculation site

Fig. 11

BDV genome PCR

Vero | p/mGFP | 5' GFP
I U | a b a b | a b a b a. Cerebrum
b. Cerebellum

Fig. 14

(a) α-N (b) DsRed

Fig. 15

(a) rBDV-p/mLuci (b)

```
SEQUENCE LISTING

<160> NUMBER OF SEQ ID NOS: 45

<210> SEQ ID NO 1
<211> LENGTH: 8908
<212> TYPE: DNA
<213> ORGANISM: Borna disease virus

<400> SEQUENCE: 1
gttgcgttaa caacaaacca atcattatcc ttctaacaaa atgaacacac gcaatgccac     60
ccaagagacg cctggttgat gacgccgatg ccatggagga ccaagattta tatgaacccc    120
cagcgagcct ccccaagctc cccggaaaat tcctacaata caccgttggg gggtctgacc    180
cgcatccggg tatagggcat gagaaggata tcaggcagaa cgcagtggca ttgttagacc    240
agtcacggcg cgatatgttt catacagtaa cgcccagcct tgtgtttcta tgtttgctaa    300
tcccaggact gcacgctgcg tttgttcacg gaggggtgcc tcgtgaatct tacctgtcga    360
cgcctgttac gcgtggggaa cagactgtcg ttaagactgc aaagttttac ggggaaaaga    420
caacacagcg tgatctcacc gagctggaga tctcctctat attcagccat tgttgctcat    480
tactaattgg ggttgtgata ggatcgtcat ctaagattaa agcaggagcc gagcagatca    540
agaaaaggtt taaaactatg atggcagcct taaaccggcc atcccatggt gagactgcta    600
cactacttca gatgtttaat ccacatgagg ctatagattg gattaacggc cagccctggg    660
taggctcctt tgtgttgtct ctactaacta cagactttga gtccccaggt aaagaattca    720
tggatcagat taaacttgtc gcaagttatg cgcagatgac tacgtacact actataaagg    780
agtacctcgc agaatgtatg gatgctaccc ttacaatccc tgtagttgca tatgagattc    840
```

```
gtgacttttt agaagtttca gcaaagctta agaggaaca tgctgacctg tttccgttcc      900
tgggggctat tcggcacccc gacgctatca agcttgcgcc acggagcttt cccaatctgg     960
cttctgcagc gttttactgg agtaagaagg agaatcccac aatggcgggc taccgggcct    1020
ccaccatcca gccgggcgcg agtgtcaagg agacccagct tgcccggtat aggcgccgcg    1080
agatatctcg cggggaagac ggggcagagc tctcaggtga gatctctgcc ataatgagaa    1140
tgataggtgt gactggtcta aactagaaaa caatgaacaa accaataaaa aaccaaatgc    1200
ggcaaacccc ccgcgacctg tgatgagttc cgacctccgg ctgacattgc ttgaattagt    1260
caggaggctc aatggcaacg ggaccatcga gtctggtcga ctccctggag gacgaagaag    1320
atccccagac actacgacgg gaacgatcgg ggtcaccaag accacggaag atcccaagga    1380
atgcattgac ccaaccggta gaccagctcc tgaaggacct caggaagaac ccctccatga    1440
tctcagaccc agaccagcga accggaaggg agcagctatc gaatgatgag cttatcaaga    1500
agctagtgac ggagctggcc gagaatagca tgatcgaggc tgaggaggtg cggggcactc    1560
ttggggacat ctcggctcgc atcgaggcag ggtttgagtc cctgtccgcc ctccaagtgg    1620
aaaccatcca gacagctcag cggtgcgacc actccgatag catcagaatc cttggcgaga    1680
acatcaagat actggatcgc tccatgaaga caatgatgga gacaatgaag ctcatgatgg    1740
agaaggtgga cctcctctac gcatcaaccg ccgttgggac ctctgcaccc atgttgccct    1800
cccatcctgc acctccgcgc atttatcccc agctcccaag tgccccgaca gcggatgagt    1860
gggacatcat accataaaaa aatcgaatca ccatgaattc aaagcattcc tatgtggagc    1920
tcaagggcaa ggtaatcgtc cctggatggc ccacactgat gcttgagata gactttgtag    1980
gagggacttc acggaaccag ttccttaaca tcccatttct ttcagtgaaa gagcctctgc    2040
agcttccacg cgagaagaag ttgaccgact acttcaccat tgacgtagag ccagcaggtc    2100
attccctggt caacatatac ttccagattg acgacttctt gctcctaaca ctcaactcac    2160
tgtccgtata caaggacccg attaggaaat acatgttcct acgcctcaac aaggaacaga    2220
gcaagcacgc aattaatgca gctttcaatg tcttctctta tcggcttcgg aacattggtg    2280
ttggccctct cggcccagac attcgatctt cagggcctta gttgcaatac tgactccact    2340
cctggattaa tcgatctgga gataaggcga cttttgccaca ccccaacgga aaatgtcatt    2400
tcatgcgagg ttagttatct taaccacacg actattagcc tcccggcagt ccacacgtca    2460
tgcctcaagt accactgcaa aacctattgg ggattctttg gtagctacag cgctgaccga    2520
atcatcaatc ggtacactgg tactgttaag ggttgtttaa caactcagc gccagaggat    2580
cccttcgagt gcaactggtt ctactgctgc tcggcgatta acagagat ctgccgatgc    2640
tctattacaa atgtcacggt ggctgtacag acattccac cgttcatgta ctgcagtttc    2700
gcggactgta gtactgtgag tcagcaggag ctagagagtg gcaaggcaat gctgagcgat    2760
ggcagtacct taacttatac cccgtatatc ttacaatcag aagtcgtgaa caaaaccctt    2820
aatgggacta tactctgcaa ctcatcctcc aagatagttt ccttcgatga atttaggcgt    2880
tcatactccc tagcgaatgg tagttaccag agctcatcaa tcaatgtgac gtgtgtaaac    2940
tacacgtcgt cctgccggtc caagttgaga aggcggcgta gggatactca acagattgag    3000
tacctagttc acaagcttag gcctacactg aaagatgcgt gggaggactg tgagatcctc    3060
cagtctctgc tcctagggat gttttggtact gggattgcaa gtgcttcgca attcttgagg    3120
ggctggctca accaccctga tatcatcggg tatatagtta atggagttgg ggtagtctgg    3180
caatgccatc gtgttaatgt cacgttcatg gcgtggaatg agtccacata ttaccctcca    3240
```

```
gtagattaca atggacggaa gtactttctg aatgatgagg ggaggctaca aacaaacacc    3300
cccgaggcaa ggccagggct taagcgggtc atgtggttcg gcaggtactt cctagggaca    3360
gtagggtctg gggtgaaacc gaggaggatt cggtacaata agacctcaca tgattaccat    3420
ctagaggagt ttgaggcaag tctcaacatg acccccagga ccagtatcgc ctcgggtcat    3480
gagacagacc ccataaatca tgcctacgga acgcaggctg acctccttcc atacaccagg    3540
tctagtaata taacgtctac agatacaggc tcaggctggg tgcacatcgg cctaccctca    3600
tttgctttcc tcaatcctct cgggtggctt agggacctac ttgcgtgggc ggcctggttg    3660
ggtggggttc tatacttaat aagtctttgt gtttccttac cagcctcctt cgcgaggagg    3720
agacgcctcg gccggtggca ggaataaacc gtaccgacca aactcttaaa aaccctcttc    3780
tcgggacaga ggtctctttc tgccttaaat cgagttcact cccccatcac gtacgagcat    3840
tgggccagat taaagcaaag aacctggcat cctgtgacta ttacttgcta ttccgccaag    3900
ttgtattgcc ccctgaagta tatcccattg gtgtcttaat aagagctgcg gaggccatac    3960
taacagttat agtatcagct tggaagctgg atcacatgac aaagacccta tactcctctg    4020
tgagatatgc actcaccaat ccccgggtcc gggcccaact tgagctccac attgcctacc    4080
agcgcatagt gggtcaggtc tcgtatagcc gggaagcaga tagggcca aaaaggcttg    4140 ggaatatgtc attgcaattc atccaatccc tcgttattgc caccatagac acaacgagct    4200
gcctaatgac ctacaaccac tttcttgctg cagcagacac agccaagagc agatgccacc    4260
tcctaatcgc ctcagtggtc caaggagccc tttgggagca agggtcattt cttgatcata    4320
taatcaacat gatcgacaca attgactcaa tcaacctccc ccatgatgat tacttcacaa    4380
ttattaagtc tatctctccc tactcccaag ggcttgttat ggggaggcac aatgtgtcag    4440
tctcctctga ttttgcgtcc gtatttacta ttcctgaatc atgcccacaa ctagacagct    4500
tactaaaaaa actgcttcaa cttgaccctg ttctcctcct catggtctct tcggtgcaga    4560
agtcatggta cttccctgag atccgaatgg ttgacgggtc acgggagcag ctccacaaga    4620
tgcgtgtcga gctggagacg ccccaagccc tgctgtcata cggccatacc ctcctgtcaa    4680
tatttcgagc agagtttatc aaaggctatg tctcaaagaa tgcgaagtgg ccgcctgtac    4740
acctgctccc aggctgtgac aaatccataa agaatgcgag agagctgggc cgctggagcc    4800
cggtgtttga ccgacgatgg cagctcttcg cgaaggttgt cattctaaga attgctgacc    4860
tagatatgga tcccgacttc aacgatattg ttagcgacaa ggcgataatc agctcaagaa    4920
gggactgggt atttgagtac aatgcagcag cctttttggaa gaaatacagt gagcggttgg    4980
agaggccccc tgccagatcg ggaccatcac ggcttgtgaa tgctctgatc gatggacgct    5040
tagataatat cccagccctg ctagagccat tttacagggg agcggttgag tttgaggatc    5100
ggctgactgt gctcgtgcct aaggagaagg agttgaaggt aaagggaagg ttcttctcga    5160
agcaaacatt ggcaatcagg atatatcagg ttgttgctga agctgcactt aagaacgagg    5220
ttatgccata cttaaaaaca cattcaatga ccatgagctc aacggcccta acccatcttc    5280
ttaaccggct atcacatact atcactaagg gtgactcctt tgttattaac ttagattata    5340
gctcctggtg caacggtttc cgaccagaac tacaagcccc actctgtcgt cagttggatc    5400
agatgttcaa ttgcgggtac ttcttcagga ctgggtgcac actgccatgc tttaccacgt    5460
ttattattca ggacagattc aacccgcccct attccttccg tggtgagccc gttgaagacg    5520
gtgtcacatg cgcggttggg actaagacaa tgggagaggg tatgaggcag aaactatgga    5580
```

```
caattcttac gagctgctgg gagataattg ctcttcggga aattaacgtg acgtttaata    5640
tactaggcca gggtgataat cagacaatca ttgtacataa atctgcaagc caaaataatc    5700
agctattagc ggagcgagca ttgggagctt tgtacaagca tgctagatta gctggccata    5760
accttaaggt agaagaatgt tgggtgtcag attgtctgta tgagtatgga aagaagctct    5820
tcttccgtgg tgtacctgtc ccaggctgtt tgaagcagct ctcgcgggtg acggactcca    5880
ctggggagtt attcccaaac ctatactcaa agttagcctg cttaacatca tcatgcttaa    5940
gcgcagcgat ggcagacaca tccccatggg tggcactcgc gacaggtgtc tgtctgtatc    6000
ttatcgagtt gtatgttgag ctgcctccgg caatcatgca ggacgagtcg ctgttaacga    6060
ccctctgtct cgtaggtcca tccattggtg ggcttccaac tcctgcaacc ctgcccagtg    6120 tcttttcag aggaatgtcc gacccattgc cctttcagct agcactcttg cagaccctca    6180
ttaaaacgac aggggtgact tgtagcttgg tgaatcgtgt ggttaagtta cggatagcac    6240
cctatccaga ctggctctcc ctagtgactg acccgacttc actcaacatt gctcaggtgt    6300
accggccaga acgtcaaatc aggaggtgga ttgaggaggc aatagcaaca agctcacact    6360
cgtcacgcat agcaactttt ttccagcagg ccctcacgga gatggcccag ctgcttgcga    6420
gggacctctc aacaatgatg cctcttcggc cccgggatat gtcggcctta ttcgcattat    6480
caaatgtcgc atatggtcta agcattatag atctatttca aaagtcctct accgttgtct    6540
ctgcaagtca agctgtccat atcgaagatg ttgccctaga gagtgtaagg tataaggaat    6600
ctatcattca gggtctgtta gacactactg aggggtacaa catgcaacct tatttggaag    6660
gttgcactta ccttgcagcc aagcagctac ggaggttgac gtggggtcga gacctagttg    6720
gagttacaat gccgtttgtt gccgagcaat ccatcccca tagttctgtc ggtgcaaaag    6780
cagaactcta cctcgatgct atcatatact gcccacaaga gacgttgcgg tcacaccatc    6840
tgactaccag gggggaccag ccgctttacc ttggatctaa tacggctgtc acggttcagc    6900
gaggtgagat cacaggccta acaaagtcaa gggctgcaaa tctagtcaag gacactctcg    6960
ttctccacca gtggtacaag gtccgtaagg ttaccgatcc acacttgaac actctcatgg    7020
cgcgcttctt gcttgagaag ggatacacat ctgacgctcg gcctagcatt cagggtggga    7080
ccctcacaca tcgtctccca tcccgtggag actcacgcca agggctcact gggtatgtga    7140
atatactcag cacgtggctc cggttctcaa gtgattatct tcactctttc tcgaaatcat    7200
cagatgacta cacaatccac ttccagcatg tattcacata cggttgcctc tatgctgatt    7260
cggtgattag atcgggcggt gttatttcca ctccttacct tttgagtgca agttgtaaaa    7320
catgctttga gaagatagac tcagaggagg tcgtcctggc atgcgaacct caatatagggg    7380 gtgctgagtg gctgatatca aagccagtta ctgtccctga gcagataatt gacgctgaag    7440
tcgagtttga cccctgtgtg agtgcgagtt attgtctcgg gattctcatt ggcaagtcat    7500
tcttggttga cataagggca agtgggcatg atattatgga gcagcggaca tgggctaact    7560
tggagaggtt ttctgtgtcg acatgcagaa acttccatg gagtattgta attcggtctc    7620
tctggagatt ccttattggc gcacgactcc tccagtttga aaggctggc cttattagga    7680 tgctgtatgc tgcaacaggt ccaaccttta gcttcctaat gaaagtcttt caagactcag    7740
ccctacttat ggactgcgca cctcttgatc ggctgtaccc taggatcaac tttcatagtc    7800
ggggagacct cgtcgccaag ctcgttttat taccttcat caacccgggt atagtggaga    7860
ttgaagtgtc tagaattaat agcaagtatc atgcagtatc ggaggctaat atggatctgt    7920
acatcgctgc tgcaaaatct gtgggcgtaa agcccacaca gtttgttgag gaaacaaacg    7980
```

```
actttacggc cgcggccac caccatggtt gttattccct ttcttggtct aagtcacgca    8040
atcaatcaca ggtcctaaag atggtagtgc ggaagctgaa gctatgtgtc ctgtatatat    8100
accccacagt cgatcccgcc gttgctctcg acctgtgcca cctgccagca ctaactataa    8160
tcctagtgct cggcggtgac ccagcgtact acgagcgatt acttgagatg gacctatgcg    8220
gggctgtgtc aagtcgcgtt gatatccccc attccctagc tgccagaacg cacaggggt     8280 tcacaatagg cccagacgct ggtccaggtg tgattagact tgacaagtta gagtcggttt    8340
gttacgccca cccctgtttg gaggagctag agtttaatgc gtacctagac tctgagttag    8400
ttgatattag tgatatgtgc tgcctccccc tagcgacacc ctgtaaggcc ctattcaggc    8460
cagtgtatcg gagcttacag tcgttcaggt tagccttaat ggacaactat agttttgtaa    8520
tggacctcat tacgatccgg ggggtggaca tcaggcctca ccttgaggag tttgatgaac    8580
tgcttgtggt ggggcagcat atcctcggtc agcccgtcct agtggaggtt gtttactacg    8640
ttggagttgt tgggaagcgt cctgtgttag cgaggcatcc ctggtcagca gatcttaagc    8700
gaatcactgt aggggggcga gcgccctgcc cttctgctgc tggactgcgt gatgaggatt    8760 gtcggggtc tctgctggtt gggcttcccg ctggattgac gcagttgttg gtggttgatt     8820
gaggttgagc catctactgc cctattctta aaaaaccata cgtcagtggt gcagtgcttg    8880
ggtttggttg ttgctttgtt gtagcgct                                       8908

<210> SEQ ID NO 2
<211> LENGTH: 72
<212> TYPE: RNA
<213> ORGANISM: Artificial
<220> FEATURE:
<223> OTHER INFORMATION: Synthetic oligonucleotide

<400> SEQUENCE: 2
uuguagccgu cugaugaguc cgugaggacg aaacuauagg aaaggaauuc cuauagucag    60
cgcuacaaca aa                                                        72

<210> SEQ ID NO 3
<211> LENGTH: 72
<212> TYPE: RNA
<213> ORGANISM: hepatitis delta virus

<400> SEQUENCE: 3
ggccggcaug gucccagccu ccucgcuggc gccggcuggg caacaccauu gcacuccggu    60
ggcgaauggg ac                                                        72

<210> SEQ ID NO 4
<211> LENGTH: 113
<212> TYPE: DNA
<213> ORGANISM: SV40 virus

<400> SEQUENCE: 4 aagcttttg caaaagccta ggcctccaaa aaagcctcct cactacttct ggaatagctc     60
agaggccgag gcggcctcgg cctctgcata ataaaaaaa attagtcagc cat            113

<210> SEQ ID NO 5
<211> LENGTH: 30
<212> TYPE: DNA
<213> ORGANISM: Artificial
<220> FEATURE:
<223> OTHER INFORMATION: Oligonucleotide for primer
```

```
<400> SEQUENCE: 5
ggaatgcatt gacccaaccg gtagaccagc                                    30

<210> SEQ ID NO 6
<211> LENGTH: 34
<212> TYPE: DNA
<213> ORGANISM: Artificial
<220> FEATURE:
<223> OTHER INFORMATION: Oligonucleotide for primer

<400> SEQUENCE: 6
aacatgtatt tcctaatcgg gtccttgtat acgg                               34

<210> SEQ ID NO 7
<211> LENGTH: 41
<212> TYPE: DNA
<213> ORGANISM: Artificial
<220> FEATURE:
<223> OTHER INFORMATION: Oligonucleotide for primer

<400> SEQUENCE: 7
ttcgaaggtt ggttaattaa ccataaaaaa atcgaatcac c                       41

<210> SEQ ID NO 8
<211> LENGTH: 41
<212> TYPE: DNA
<213> ORGANISM: Artificial
<220> FEATURE:
<223> OTHER INFORMATION: Oligonucleotide for primer

<400> SEQUENCE: 8
ttaattaacc aaccttcgaa ggtgattcga ttttttatg g                        41

<210> SEQ ID NO 9
<211> LENGTH: 30
<212> TYPE: DNA
<213> ORGANISM: Artificial
<220> FEATURE:
<223> OTHER INFORMATION: Oligonucleotide for primer

<400> SEQUENCE: 9
ggaatgcatt gacccaaccg gtagaccagc                                    30

<210> SEQ ID NO 10
<211> LENGTH: 34
<212> TYPE: DNA
<213> ORGANISM: Artificial
<220> FEATURE:
<223> OTHER INFORMATION: Oligonucleotide for primer

<400> SEQUENCE: 10
aacatgtatt tcctaatcgg gtccttgtat acgg                               34

<210> SEQ ID NO 11
<211> LENGTH: 16
<212> TYPE: DNA
<213> ORGANISM: Borna disease virus

<400> SEQUENCE: 11
taaaaaaatc gaatca                                                   16

<210> SEQ ID NO 12
<211> LENGTH: 34
<212> TYPE: DNA
<213> ORGANISM: Artificial
```

-continued

```
<220> FEATURE:
<223> OTHER INFORMATION: Oligonucleotide for primer

<400> SEQUENCE: 12
ccgtatacaa ggacccgatt aggaaataca tgtt                                    34

<210> SEQ ID NO 13
<211> LENGTH: 32
<212> TYPE: DNA
<213> ORGANISM: Artificial
<220> FEATURE:
<223> OTHER INFORMATION: Oligonucleotide for primer

<400> SEQUENCE: 13
aagagaagac gttgaaagct gcgttaattg cg                                      32

<210> SEQ ID NO 14
<211> LENGTH: 32
<212> TYPE: DNA
<213> ORGANISM: Artificial
<220> FEATURE:
<223> OTHER INFORMATION: Oligonucleotide for primer

<400> SEQUENCE: 14
cgcaattaac gcagctttca acgtcttctc tt                                      32

<210> SEQ ID NO 15
<211> LENGTH: 29
<212> TYPE: DNA
<213> ORGANISM: Artificial
<220> FEATURE:
<223> OTHER INFORMATION: Oligonucleotide for primer

<400> SEQUENCE: 15
gggtctgcaa gagtgctagc tgaaagggc                                          29

<210> SEQ ID NO 16
<211> LENGTH: 33
<212> TYPE: DNA
<213> ORGANISM: Artificial
<220> FEATURE:
<223> OTHER INFORMATION: Oligonucleotide for primer

<400> SEQUENCE: 16
gcgaaggagg ctcgcatgaa atgacatttt ccg                                     33

<210> SEQ ID NO 17
<211> LENGTH: 35
<212> TYPE: DNA
<213> ORGANISM: Artificial
<220> FEATURE:
<223> OTHER INFORMATION: Oligonucleotide for primer

<400> SEQUENCE: 17
tcatttcatg cgagcctcct tcgcgaggag gagac                                   35

<210> SEQ ID NO 18
<211> LENGTH: 35
<212> TYPE: DNA
<213> ORGANISM: Artificial
<220> FEATURE:
<223> OTHER INFORMATION: Oligonucleotide for primer

<400> SEQUENCE: 18
tcggtaccat gcagctttca atgtcttctc ttatc                                   35
```

<210> SEQ ID NO 19
<211> LENGTH: 22
<212> TYPE: DNA
<213> ORGANISM: Artificial
<220> FEATURE:
<223> OTHER INFORMATION: Oligonucleotide for primer

<400> SEQUENCE: 19
ataggagact tcgcatgaaa tg                                            22

<210> SEQ ID NO 20
<211> LENGTH: 26
<212> TYPE: DNA
<213> ORGANISM: Artificial
<220> FEATURE:
<223> OTHER INFORMATION: Oligonucleotide for primer

<400> SEQUENCE: 20
ttcatgcgaa gtctcctatc ttaacc                                        26

<210> SEQ ID NO 21
<211> LENGTH: 62
<212> TYPE: DNA
<213> ORGANISM: Artificial
<220> FEATURE:
<223> OTHER INFORMATION: Oligonucleotide for primer

<400> SEQUENCE: 21
tcccccgggt tattcctgcc accggccgag gcgtctcctc ctcgcgaagc ttgcgggtaa    60
gg                                                                  62

<210> SEQ ID NO 22
<211> LENGTH: 41
<212> TYPE: DNA
<213> ORGANISM: Artificial
<220> FEATURE:
<223> OTHER INFORMATION: Oligonucleotide for primer

<400> SEQUENCE: 22
ccgaattcac cgccaccatg aagtgccttt tgtacttagc c                        41

<210> SEQ ID NO 23
<211> LENGTH: 74
<212> TYPE: DNA
<213> ORGANISM: Artificial
<220> FEATURE:
<223> OTHER INFORMATION: Oligonucleotide for primer

<400> SEQUENCE: 23
gggatatctt attcctgcca ccggccgagg cgtctcctcc tcgcgagaac caagaatagt    60
ccaatgatta accc                                                     74

<210> SEQ ID NO 24
<211> LENGTH: 44
<212> TYPE: DNA
<213> ORGANISM: Artificial
<220> FEATURE:
<223> OTHER INFORMATION: Oligonucleotide for primer

<400> SEQUENCE: 24
ccggtaccgc caccatggtt ccgcaagctc ttctgcttgt accc                     44

<210> SEQ ID NO 25
<211> LENGTH: 80

<212> TYPE: DNA
<213> ORGANISM: Artificial
<220> FEATURE:
<223> OTHER INFORMATION: Oligonucleotide for primer

<400> SEQUENCE: 25
gggatatctt attcctgcca ccggccgagg cgtctcctcc tcgcacaaca tgtcattagg    60
aaaattatca acatcaaggc                                                80

<210> SEQ ID NO 26
<211> LENGTH: 73
<212> TYPE: DNA
<213> ORGANISM: Artificial
<220> FEATURE:
<223> OTHER INFORMATION: Oligonucleotide for primer

<400> SEQUENCE: 26
gtaattaatt aaccataaaa aaatcgaatc accatgtcat ttcatgcgag cctccttcgc    60
gaggaggaga cgc                                                       73

<210> SEQ ID NO 27
<211> LENGTH: 29
<212> TYPE: DNA
<213> ORGANISM: Artificial
<220> FEATURE:
<223> OTHER INFORMATION: Oligonucleotide for primer

<400> SEQUENCE: 27
gggtctgcaa gagtgctagc tgaaagggc                                      29

<210> SEQ ID NO 28
<211> LENGTH: 30
<212> TYPE: DNA
<213> ORGANISM: Artificial
<220> FEATURE:
<223> OTHER INFORMATION: Oligonucleotide for primer

<400> SEQUENCE: 28
ggaatgcatt gacccaaccg gtagaccagc                                     30

<210> SEQ ID NO 29
<211> LENGTH: 43
<212> TYPE: DNA
<213> ORGANISM: Artificial
<220> FEATURE:
<223> OTHER INFORMATION: Oligonucleotide for primer

<400> SEQUENCE: 29
atttaaatgg ttggcctgca ggggtgattc gattttttta tgg                      43

<210> SEQ ID NO 30
<211> LENGTH: 63
<212> TYPE: DNA
<213> ORGANISM: Artificial
<220> FEATURE:
<223> OTHER INFORMATION: Oligonucleotide for primer

<400> SEQUENCE: 30
aaggttcgaa ggtgattcga tttttttatg gtatttaaat ggttggcctg caggggtgat    60
tcg                                                                  63

<210> SEQ ID NO 31
<211> LENGTH: 128
<212> TYPE: DNA

```
<213> ORGANISM: Artificial
<220> FEATURE:
<223> OTHER INFORMATION: Vector

<400> SEQUENCE: 31
ttcgaactgg aggcttgctg aaggctgtat gctgttgtct tcaagatctg gaagacacag      60
gacacaaggc ctgttactag cactcacatg gaacaaatgg ccaccgtggg aggatgacaa     120
ttaattaa                                                              128

<210> SEQ ID NO 32
<211> LENGTH: 64
<212> TYPE: DNA
<213> ORGANISM: Artificial
<220> FEATURE:
<223> OTHER INFORMATION: miR155

<400> SEQUENCE: 32
gctgttaatg ctaattgtga tagggtttt ggcctctgac tgactcctac ctgttagcat       60
taac                                                                   64

<210> SEQ ID NO 33
<211> LENGTH: 64
<212> TYPE: DNA
<213> ORGANISM: Artificial
<220> FEATURE:
<223> OTHER INFORMATION: miR155

<400> SEQUENCE: 33
aattacgatt aacactatcc ccaaaaccgg agactgactg aggatggaca atcgtaattg      60
agga                                                                   64

<210> SEQ ID NO 34
<211> LENGTH: 35
<212> TYPE: DNA
<213> ORGANISM: Artificial
<220> FEATURE:
<223> OTHER INFORMATION: Oligonucleotide for primer

<400> SEQUENCE: 34
ggtcttcgaa atgggcaagt cagaaagtca gatgg                                 35

<210> SEQ ID NO 35
<211> LENGTH: 41
<212> TYPE: DNA
<213> ORGANISM: Artificial
<220> FEATURE:
<223> OTHER INFORMATION: Oligonucleotide for primer

<400> SEQUENCE: 35
gtgcagttaa ttaatcacca aacccggcac ttcttttctg g                          41

<210> SEQ ID NO 36
<211> LENGTH: 27
<212> TYPE: DNA
<213> ORGANISM: Artificial
<220> FEATURE:
<223> OTHER INFORMATION: Oligonucleotide for primer

<400> SEQUENCE: 36
attacgtgtc ctatgaccat gccgatg                                          27

<210> SEQ ID NO 37
<211> LENGTH: 25
```

```
<212> TYPE: DNA
<213> ORGANISM: Artificial
<220> FEATURE:
<223> OTHER INFORMATION: Oligonucleotide for primer

<400> SEQUENCE: 37
cgtaatcacc catggcttcg atgac                                     25

<210> SEQ ID NO 38
<211> LENGTH: 34
<212> TYPE: DNA
<213> ORGANISM: Artificial
<220> FEATURE:
<223> OTHER INFORMATION: Oligonucleotide for primer

<400> SEQUENCE: 38
gcggaaattc gtcgacctgg aggcttgctg aagg                           34

<210> SEQ ID NO 39
<211> LENGTH: 34
<212> TYPE: DNA
<213> ORGANISM: Artificial
<220> FEATURE:
<223> OTHER INFORMATION: Oligonucleotide for primer

<400> SEQUENCE: 39
cgctctagac tcgagttgtc atcctcccac ggtg                           34

<210> SEQ ID NO 40
<211> LENGTH: 64
<212> TYPE: DNA
<213> ORGANISM: Artificial
<220> FEATURE:
<223> OTHER INFORMATION: miR-GAPDH

<400> SEQUENCE: 40
gctgttgatg acaagcttcc cattcttttt ggcctctgac tgaagaatgg aatttgtcat    60
caac                                                                64

<210> SEQ ID NO 41
<211> LENGTH: 64
<212> TYPE: DNA
<213> ORGANISM: Artificial
<220> FEATURE:
<223> OTHER INFORMATION: miR-GAPDH

<400> SEQUENCE: 41
aactactgtt cgaagggtaa gaaaaaccgg agactgactt cttaccttaa acagtagttg    60
tcct                                                                64

<210> SEQ ID NO 42
<211> LENGTH: 62
<212> TYPE: DNA
<213> ORGANISM: Artificial
<220> FEATURE:
<223> OTHER INFORMATION: miR-APP

<400> SEQUENCE: 42
gctgttctgg acattcatgt gcatgttttt ggcctctgac tgatatgccc gaatgtccag    60
aa                                                                  62

<210> SEQ ID NO 43
<211> LENGTH: 62
<212> TYPE: DNA
```

```
<213> ORGANISM: Artificial
<220> FEATURE:
<223> OTHER INFORMATION: miR-APP

<400> SEQUENCE: 43
ttctggacat cgggcatat cagtcagagg ccaaaaacat gcacatgaat gtccagaatc      60
ct                                                                    62

<210> SEQ ID NO 44
<211> LENGTH: 20
<212> TYPE: DNA
<213> ORGANISM: Artificial
<220> FEATURE:
<223> OTHER INFORMATION: Oligonucleotide for primer

<400> SEQUENCE: 44
ctggcctgct ggctgaaccc                                                 20

<210> SEQ ID NO 45
<211> LENGTH: 20
<212> TYPE: DNA
<213> ORGANISM: Artificial
<220> FEATURE:
<223> OTHER INFORMATION: Oligonucleotide for primer

<400> SEQUENCE: 45
gccccgcttg caccagttct                                                 20
```

VECTOR UTILIZING BORNA DISEASE VIRUS AND USE THEREOF

This application is a U.S. national stage of International Application No. PCT/JP2010/054600 filed Mar. 17, 2010.

TECHNICAL FIELD

The present invention relates to a viral vector and a recombinant virus for introducing a foreign gene into a cell and to use of the viral vector and the recombinant virus.

BACKGROUND ART

Use of a viral vector is known as a method for delivering a foreign gene into living bodies or cells. Until now various vectors have been developed utilizing a retrovirus, a lentivirus, an adenovirus, an adeno-associated virus, and Sendai virus.

These conventional viral vectors, however, have the following disadvantages. For example, in cases where the vector is a DNA virus, the viral gene is integrated into a host chromosome, thereby exhibiting pathogenicity for the host (for example, humans). Some of the conventional viral vectors have a narrow host range and thus can only be applied to a particular organism. In addition, the gene transfer efficiency of the conventional viral vectors is poor because it varies with the insertion site of a foreign gene into the viral genome. Furthermore, the stability and persistency of the conventional viral vectors are poor due to elimination of the introduced virus by the immune response in a living body, mutation of the viral gene, and/or changes in the promoter efficiency.

In gene therapy and the like, a gene transfer technique capable of introducing a gene into only a target cell has been desired. In particular, since gene therapy is considered to be effective for treating neurological diseases, development of a viral vector capable of selectively introducing a gene into a neuron and having excellent safety, stability, persistency, and gene transfer efficiency has been desired.

Borna disease virus (hereinafter also referred to as BDV) is a neurotropic virus belonging to the order Mononegavirales and having a single nonsegmented minus-strand RNA as a genome. BDV replicates itself in the cell nucleus, and is characterized by non-cytotoxic, prolonged persistent infection and very wide host range (Protein, Nucleic Acid and Enzyme, Vol. 52, No. 10, 1168-1174 (2007); and Keizo Tomonaga, Boruna Byou Uirus Kansen To Tyuusuushinkeikei Shikkan (Borna Disease Virus Infection and Neurological Disorders), Saishin Igaku, Vol. 60, No. 2 (offprint from the February, 2005 issue), 79-85).

A technique, utilizing BDV, for foreign gene transfer into cells has been reported in U. Schneider et al., Journal of Virology, 7293-7296 (2007). In this literature, an expression cassette encoding a green fluorescent protein (GFP) is inserted into the untranslated region at the 5' end of the BDV genome, and this recombinant virus is used with a high-activity polymerase to infect a rat. As a result, the GFP gene is expressed in the neurons of the rat.

JP-2010-22338-A discloses a viral vector comprising (a) a cDNA encoding a recombinant Borna disease virus genome in which a foreign gene is inserted into the open reading frame of the G gene, (b) a cDNA encoding a ribozyme, and (c) a promoter sequence, each being disposed in a position in which (b) is placed upstream and downstream of (a), and (a) and (b) are placed downstream of (c).

The above technique using BDV would enable selective insertion of a foreign gene into central nervous system cells. However, the gene transfer efficiency of this technique using BDV is not high enough and hence needs to be improved. Thus, so far there has not been developed any viral vector having a high replicative efficiency of a recombinant virus, a wide host range, a high safety, a high foreign gene transfer efficiency, excellent stability and persistency, and a capability of selectively introducing a foreign gene into the central nervous system.

SUMMARY OF INVENTION

Technical Problem

An object of the present invention to provide a viral vector having a wide host range, a high foreign gene transfer efficiency, safety due to no integration of the viral genome into a host chromosome, excellent intracellular stability and persistency due to non-cytotoxic expression of the foreign gene in the cell nucleus, a capability of selectively introducing the foreign gene into a target cell (for example, a central nervous system cell such as a cranial nerve system cell, or the like), and a capability of efficiently producing a low pathogenic (highly safe) recombinant virus due to transmissibility only to the target cell; and to provide the recombinant virus, a process for introducing a foreign gene using the recombinant virus, a foreign gene transfer agent, and the like.

Solution to Problem

In order to solve the above problems, the inventors conducted extensive research on the insertion site of a foreign gene into the BDV genome (RNA viral genome) by preparing various viral vectors each containing a cDNA encoding a recombinant BDV genome (a cDNA of a recombinant BDV genome RNA) in which a foreign gene is inserted into a different site, and introducing the viral vector together with the helper plasmid described below (a plasmid (group) expressing the N gene, the P gene, and the L gene of BDV) into a cell to produce a recombinant virus, and infecting a cell with the obtained recombinant virus. As a result, the inventors found out that, in cases where a foreign gene is inserted into the untranslated region between the open reading frame (ORF) of the P gene and the open reading frame of the M gene (the untranslated region connected to the downstream of the ORF of the P gene) in the BDV genome, a vector having a high recombinant virus productivity (having a high replicative efficiency of the recombinant virus produced from the vector) can be obtained. The inventors also found out that the recombinant virus produced from the vector efficiently expresses a foreign gene in a cell, i.e., the recombinant virus can very efficiently introduce a foreign gene into a cell.

The production of such a recombinant BDV vector in which a foreign gene is inserted into the untranslated region between the open reading frame of the P gene and the open reading frame of the M gene has been considered to be impossible until now. The inventors, however, succeeded in the production of the recombinant BDV vector for the first time. In conventional recombinant BDV vectors, a foreign gene is inserted into the G gene region (JP-2010-22338-A) or the 5' end region of the genome (U. Schneider et al., Journal of Virology, 7293-7296 (2007)) for expression of the gene. However, the vector in which a foreign gene is inserted into the G gene region has a low recombinant virus productivity, and the infection of a cell with the recombinant virus produced from the vector is temporary and thus the virus cannot express a foreign gene persistently. In addition, the recombinant BDV vector in which a foreign gene is inserted into the 5' end region of the genome has a low transfer efficiency of the gene. The inventors found out that a recombinant BDV vector in which a foreign gene is inserted into the untranslated region between the open reading frame of the P gene and the open reading frame of the M gene has a higher virus productivity than conventional recombinant BDV vectors and that the recombinant virus produced from the vector can highly efficiently express a target gene for a prolonged periods even in a cranial nerve system cell. The inventors then conceived that with the use of the novel recombinant BDV vector, various kinds of foreign genes can be efficiently introduced into a target cell.

The inventors also found out that the pathogenicity of the recombinant virus produced from the vector can be reduced by destructing (deleting) the sequence encoding the G gene in the above viral vector obtained by using the cDNA of the recombinant BDV genome in which a foreign gene is inserted into the untranslated region between the ORF of the P gene and the ORF of the M gene (the untranslated region connected to the downstream of the ORF of the P gene) of the BDV genome. The recombinant virus produced from such a G gene deleted viral vector can establish persistent infection in a cell that the virus has been introduced because the intracellular replication ability of the virus is maintained; however, the recombinant virus is not transmissible to other cells since the virus cannot produce a G protein. The inventors also found out that destruction of the G gene and the M gene in such a recombinant viral vector can further reduce the transmissibility of the recombinant virus, while the intracellular replication ability thereof is maintained. The inventors further found out that connecting the ORFs of the L gene, which are divided by the G gene in the BDV genome, by deleting an intron of the L gene (part of the G gene) in the viral vector can improve the replication ability of the produced recombinant virus, i.e., can make faster the replication rate of a foreign gene in a cell.

The inventors further found out that the cell tropism of the recombinant virus can be altered through the viral production using a gene encoding the coat protein of another virus together with the above G gene deleted viral vector and therefore a target gene can be efficiently introduced into various kinds of cells.

The BDV genome encodes at least six proteins: a nucleoprotein (N protein), the X protein, a phosphoprotein (P protein), a matrix protein (M protein), a surface glycoprotein (G protein), and an RNA-dependent RNA polymerase (L protein). FIG. 1 is a schematic view of the construct of the BDV genome. In FIG. 1, N, X, P, M, G, and L schematically represent the ORFs of each gene. The BDV genome has, from the 3' end, the N, X, P, M, G, and L genes in this order as shown in FIG. 1. The viral RNAs encoding the G protein, the m protein, the N protein, the P protein, and the L protein are herein referred to as the G gene, the M gene, the N gene, the P gene, and the L gene, respectively. For example, "the cDNA of the G gene" means a cDNA encoding the G gene.

That is, the present invention relates to the following (1) to (14).

(1) A viral vector comprising
(a) a cDNA of a recombinant viral RNA
  having at least the N gene, the X gene, the P gene, and the L gene of a Borna disease virus genome in the same order as that in the Borna disease virus genome, and
  having a sequence in which a foreign gene is inserted into the untranslated region connected to the downstream of the open reading frame of the P gene,
(b) a DNA encoding a ribozyme, and
(c) a promoter sequence, each being disposed in a position in which (b) is placed upstream and downstream of (a), and (a) and (b) are placed downstream of (c).

(2) The viral vector according to (1), wherein (a) the cDNA of a recombinant viral RNA has a sequence in which the G gene of the Borna disease virus genome is destructed and has a sequence in which a foreign gene is inserted into the untranslated region connected to the downstream of the open reading frame of the P gene.

(3) The viral vector according to (1) or (2), wherein (a) the cDNA of a recombinant viral RNA has a sequence in which the G gene and the M gene of the Borna disease virus genome are destructed and has a sequence in which a foreign gene is inserted into the untranslated region connected to the downstream of the open reading frame of the P gene.

(4) The viral vector according to (1), wherein (a) the cDNA of a recombinant viral RNA is a cDNA encoding a recombinant Borna disease virus genome in which a foreign gene is inserted into the untranslated region between the open reading frame of the P gene and the open reading frame of the M gene.

(5) The viral vector according to any of (1) to (4), wherein (c) the promoter sequence is an RNA polymerase II promoter sequence.

(6) The viral vector according to any of (1) to (5), wherein (b1)) a cDNA encoding a hammer head ribozyme is placed upstream of (a) the cDNA of a recombinant viral RNA and (b2) a cDNA sequence encoding a hepatitis δ virus ribozyme is placed downstream of (a).

(7) A recombinant virus comprising an RNA encoded by the viral vector according to any of (1) to (6).

(8) A process for preparing a recombinant virus, the process comprising the steps of
  introducing, into an in vitro cell, a plasmid or a plasmid group expressing the N gene, the P gene and the L gene of a Borna disease virus as a helper plasmid, together with the viral vector according to any of (1) to (6), and
  culturing the cell having the introduced viral vector and helper plasmid to produce a recombinant virus.

(9) The process for preparing a recombinant virus according to (8), wherein a plasmid expressing the coat gene of a virus is further introduced as a helper plasmid into the in vitro cell.

(10) The process for preparing a recombinant virus according to (8) or (9), wherein a plasmid expressing the M gene of a Borna disease virus is further introduced as a helper plasmid into the in vitro cell.

(11) A process for introducing a foreign gene, the process comprising the step of infecting a cell or an animal with the recombinant virus according to (7) or a recombinant virus prepared by the process according to any of (8) to (10).

(12) A foreign gene transfer agent comprising the recombinant virus according to (7) or a recombinant virus prepared by the process according to any of (8) to (10).

(13) A foreign gene transfer agent for a cranial nerve system cell, the agent comprising the recombinant virus according to (7) or a recombinant virus prepared by the process according to any of (8) to (10).

(14) A kit for introducing a foreign gene, the kit comprising the viral vector according to any of (1) to (6).

The present invention also includes the following processes, uses, and the like:
a process for introducing a foreign gene into a cranial nerve system cell, the process comprising administering, to an animal, the recombinant virus according to (7) or a recombinant virus prepared by the process according to any of (8) to (10);
a use of the recombinant virus according to (7) or a recombinant virus prepared by the process according to any of (8) to (10) for producing a foreign gene transfer agent;

a use of the recombinant virus according to (7) or a recombinant virus prepared by the process according to any of (8) to (10) for producing a foreign gene transfer agent for a cranial nerve system cell;

the recombinant virus according to (7) or a recombinant virus prepared by the process according to (8) to (10) for introducing a foreign gene into an in vitro cell or an animal; and The recombinant virus according to (7) or a recombinant virus prepared by the process according to (8) to (10) for introducing a foreign gene into a cranial nerve system cell.

Advantageous Effects of Invention

The present invention enables the preparation of a viral vector having a wide host range, a high foreign gene transfer efficiency, safety due to no integration of the viral genome into a host chromosome, excellent host-intracellular stability and persistency due to non-cytotoxic foreign gene expression in the cell nucleus, a capability of selectively introducing a foreign gene into a target cell such as a cranial nerve system cell, and a capability of producing, with a high productivity, a low pathogenic (highly safe) recombinant virus due to transmissibility only to a target cell; and enables the preparation of such a recombinant virus. The present invention also enables the selective and efficient introduction of a foreign gene into a target cell such as a cranial nerve system cell, and enables the persistent expression of the foreign gene in the cell. In addition, the recombinant virus produced from the viral vector of the present invention causes persistent infection in the nucleus of a cell such as a cranial nerve system cell and therefore the recombinant virus is hardly attacked and eliminated by host immunity. Further, the P protein contained in the recombinant virus of the present invention has a function of inhibiting a host immune response, and consequently natural immunity is not activated by the virus-infected cell.

BRIEF DESCRIPTION OF DRAWINGS

FIG. 1 is a schematic view of the construct of the Borna disease virus genome (wild-type).

FIG. 2 (*a*) is a schematic view of the untranslated region between the ORF of the P gene and the ORF of the M gene (Base No. of the BDV genome: 1875 to 1895) in the cDNA of a wild-type BDV genome, and FIG. 2 (*b*) is a schematic view showing an example of the insertion site of a foreign gene in the viral vector of the present invention.

FIG. 3 is a schematic view showing an example of the construct of the viral vector of the present invention.

FIG. 4 is a schematic view of the construct of a recombinant viral vector (rBDV-5'GFP) obtained by inserting the GFP gene into the untranslated region at the 5' end in the BDV genome.

FIG. 5 is a graph showing the time course of the infection rates in Vero cells infected with a wild-type BDV or a recombinant BDV (changes in the infection rates from the zero day to the 19th day after infection).

FIG. 6 (*a*) and FIG. 6 (*b*) are the results of Northern blot for the gene expression and the results of Western blot for the protein expression, in cells infected with a wild-type BDV, a recombinant virus p/mGFP, or a recombinant virus 5' GFP, respectively.

FIG. 7*a* to FIG. 7*f* are photomicrographs showing the results of the protein expression in cells infected with a wild-type BDV, a recombinant virus p/mGFP, or a recombinant virus 5' GFP.

FIG. 8*a* to FIG. 8*f* are photomicrographs showing the results of the protein expression in cells infected with a wild-type BDV, a recombinant virus p/mGFP, or a recombinant virus 5' GFP.

FIG. 9 is an explanatory diagram of an experimental method for investigating the infection of a rat brain with the virus.

FIG. 10 is an illustration showing the inoculation site of the virus in a rat brain.

FIG. 11 is the results of electrophoresis of the PCR products of the BDV genomes expressed in rat brains.

FIG. 12*a* to FIG. 12*d* are the macro photographs (a and b) and fluorescent macro photographs (c and d) of the reversed side of a rat brain incised 14 days after inoculation of a recombinant virus.

The top figure in FIG. 13 and FIGS. 13*a* to 13*d* are the macro photograph (top) of the cerebral cortex and the photomicrographs (a to d) of the sections of the cerebral cortex of a virus-infected rat brain.

FIGS. 14 (*a*) and (*b*) are photomicrographs showing the results of the protein expression in cells infected with a recombinant virus obtained from an rBDV-p/mDsRed vector.

FIGS. 15 (*a*) and (*b*) are a photomicrograph (a) showing the results of the protein expression and a graph (b) showing the luciferase activity, in cells infected with a recombinant virus obtained from an rBDV-p/mLuci vector, respectively.

FIG. 16 is a schematic view showing an example of the construct of the viral vector of the present invention.

FIG. 17 is a schematic view showing an example of the construct of the viral vector of the present invention.

FIG. 18 is fluorescent photomicrographs showing a cross section of a mouse brain eight months after the inoculation of a recombinant virus (FIG. 18*a*: a macro photograph; and FIG. 18*b*: the 400-fold enlarged photograph of FIG. 18*a*).

FIG. 19 is a schematic view of the preparation procedure of a plasmid p/mGFP ΔG.

FIG. 20 is a schematic view of the preparation procedure of a plasmid p/mGFP ΔG LL.

FIG. 21 is a schematic view of the preparation procedure of a BDV G gene expression plasmid.

FIG. 22 is a graph showing the comparison of recombinant BDV productivities between a plasmid p/mGFP ΔG and a plasmid p/mGFP ΔG LL.

FIG. 23 is a graph showing the time course of the infection rates of a p/mGFP ΔG-LL virus in G gene stably expressing Vero cells and in Vero cells.

FIG. 24*a* is the results of Western blot for the protein expression in cells infected with a wild-type BDV or a G-deleted recombinant virus, and FIG. 24*b* is the fluorescent photomicrograph of Vero cells that express GFP as a result of infection with a G-deleted recombinant virus.

FIG. 25 is a schematic view of the preparation procedure of a plasmid expressing a chimeric protein having the intracellular region of the G gene of BDV and having the extracellular region and the transmembrane region of the G gene of vesicular stomatitis virus (VSV).

FIG. 26 is a graph showing the recovery efficiencies of G-deleted recombinant viruses prepared using, as a helper plasmid, the G gene of BDV, the coat gene of VSV, or the coat gene of rabies virus (Rab).

FIG. 27 is a schematic view of the preparation procedure of an M gene deleted plasmid p/mGFP ΔM-G LL.

FIG. 28 is a schematic view of the preparation procedure of a P/mGFP ΔM-G LL P-M tandem vector.

FIG. 29 is the results of Western blotting for cells infected with a recombinant virus p/mNEP.

FIG. 30 is a graph showing the enzyme activity of NEP in cells infected with a recombinant virus.

FIG. 33 is a graph showing the transcription inhibition rate of a target gene in cells infected with a recombinant virus.

FIG. 34 is a schematic view of the preparation procedure of a plasmid p/m miR×2.

FIG. 35 is a schematic view of a p/m vector into which miRNA×1 (p/m miR155), miRNA×2, or miRNA×4 is inserted.

FIG. 36 is a graph showing the effect of infection with a recombinant virus p/m-miR-GAPDH having a recombinant viral RNA into which miRNA for GAPDH is inserted.

FIG. 37 is a graph showing the effect of infection with a recombinant virus p/m-miR-APP having a recombinant viral RNA into which miRNA for APP (amyloid precursor protein) is inserted.

DESCRIPTION OF EMBODIMENTS

Figure 1:
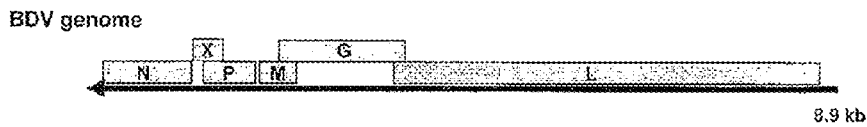

The present invention will be described below.
1. Viral Vector
The viral vector of the present invention comprises
(a) a cDNA of a recombinant viral RNA
    having at least the N gene, the X gene, the P gene, and the L gene of a Borna disease virus genome in the same order as that in the Borna disease virus genome, and
    having a sequence in which a foreign gene is inserted into the untranslated region connected to the downstream of the open reading frame of the P gene,
(b) a DNA encoding a ribozyme, and
(c) a promoter sequence,
each being disposed in a position in which (b) is placed upstream and downstream of (a), and (a) and (b) are placed downstream of (c).

Hereinafter the above (a) cDNA of a recombinant viral RNA is sometimes simply referred to as "(a) the cDNA of a recombinant BDV genome." The viral vector of the present invention may also contain another sequence besides the above (a), (b), and (c), as long as the viral vector exerts the effect of the present invention.

(a) cDNA of Recombinant BDV Genome (a) the cDNA of a recombinant BDV genome in the present invention has at least the N gene, the X gene, the P gene, and the L gene of the BDV genome in the same order as that in the Borna disease virus genome, and the recombinant BDV RNA has a sequence in which a foreign gene is inserted into the untranslated region connected to the downstream of the open reading frame of the P gene.

(a) the cDNA of a recombinant BDV genome is preferably a cDNA encoding the BDV genome or BDV genome sequence in which either or both of the G gene and the M gene are destructed and in which a foreign gene is inserted into the untranslated region connected to the downstream of the open reading frame of the P gene; and the like.

Among these, (a) the cDNA of a recombinant BDV genome in the present invention is preferably a cDNA of an RNA having a BDV genome sequence in which either or both of the G gene and the M gene are destructed and in which a foreign gene is inserted into the untranslated region connected to the downstream of the open reading frame of the P gene.

(a) the cDNA of a recombinant BDV genome in the present invention is more preferably a cDNA of a recombinant viral RNA having a BDV genome sequence in which the G gene is destructed and in which a foreign gene is inserted into the untranslated region connected to the downstream of the open reading frame of the P gene. A viral vector containing, as (a) the cDNA of a recombinant BDV genome, such a cDNA of a recombinant viral RNA having a sequence in which the G gene is destructed is hereinafter sometimes referred to as "the G gene deleted viral vector." The destruction of the G gene enables the viral vector to produce a recombinant virus that is not transmissible to other cells, except for a cell into which the virus is to be introduced, and thus the pathogenicity of the recombinant virus is reduced, which makes the recombinant virus safer. (a) the cDNA of a recombinant BDV genome in the present invention is further preferably a cDNA of a recombinant viral RNA having a BDV genome sequence in which the G gene and the M gene are destructed and in which a foreign gene is inserted into the untranslated region connected to the downstream of the open reading frame of the P gene. A viral vector containing such a cDNA of a recombinant viral RNA is hereinafter sometimes referred to as "the G gene and M gene deleted viral vector." The destruction of the G gene and the M gene can further reduce the pathogenicity of the recombinant virus and, as a result, makes the recombinant virus much safer.

"Destruction of a gene" usually means that the gene does not exist in such a form that the gene can encode a protein (for example, the G protein in the case of the G gene). Destruction of a gene can be carried out by, besides deleting the whole gene, deleting part of the gene, inserting another sequence into the gene, replacing an amino acid contained in the gene with another amino acid, or the like.

Figures 14, 15, 16, 17:
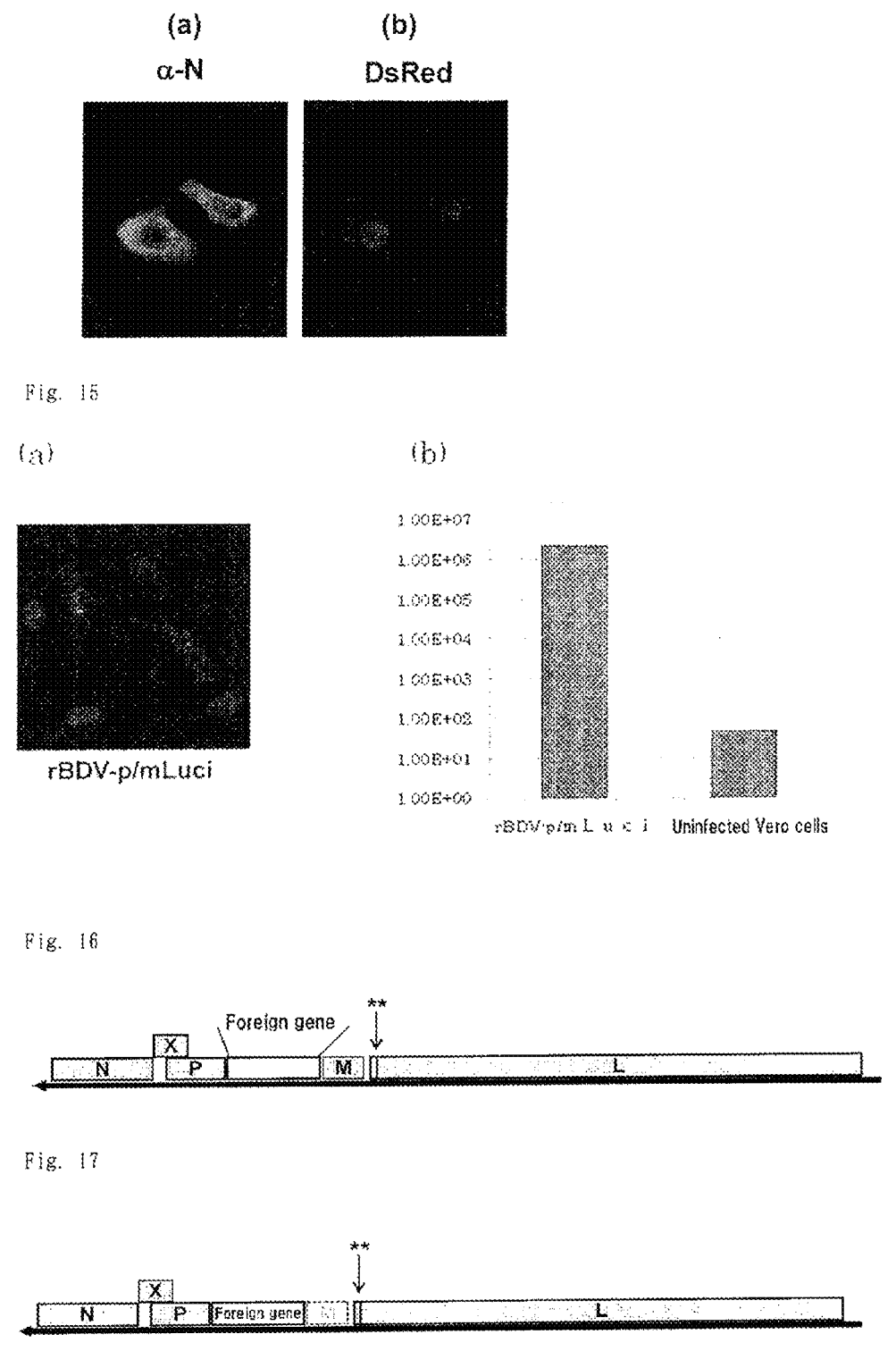

In the G gene deleted viral vector and in the G gene and M gene deleted viral vector, an intron of the L gene of the BDV genome is preferably deleted. As shown in FIG. 16, as a result of the deletion of the intron of the L gene, the ORFs of the L gene, which are divided in a wild-type BDV genome, are connected to each other and thus the replication ability of the recombinant virus, i.e., the expression efficiency of a foreign gene in a cell is further improved. The deletion of the intron of the L gene also makes possible insertion of a larger foreign gene. The deletion of the intron of the L gene can be carried out by a known method.

(a) the cDNA of a recombinant BDV genome in the present invention may be a cDNA encoding a recombinant Borna disease virus genome in which a foreign gene is inserted into the untranslated region between the open reading frame of the F gene and the open reading frame of the M gene. Such a cDNA of a recombinant BDV genome can be obtained by inserting any given foreign gene into the untranslated region between the open reading frame (ORF) of the P gene and the open reading frame of the M gene in a cDNA encoding the BDV genome (RNA viral genome).

Figure 3:
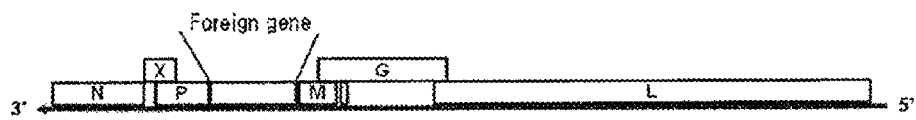

An example of the construct of (a) the cDNA of a recombinant BDV genome in the viral vector of the present invention is schematically shown in FIG. 3. FIG. 3 shows a cDNA encoding a recombinant BDV genome in which a foreign gene is inserted into the untranslated region between the open reading frame of the P gene and the open reading frame of the M gene.

An example of a preferable construct of (a) the cDNA of a recombinant BDV genome in the viral vector of the present invention is schematically shown in FIG. 16. (a) the cDNA of a recombinant BDV genome shown in FIG. 16 is a cDNA of a recombinant viral RNA having a BDV genome sequence in which the G gene is destructed (deleted) and in which a foreign gene is inserted into the untranslated region connected to the downstream of the open reading frame of the P gene.

An example of another preferable construct of (a) the cDNA of a recombinant BDV genome in the viral vector of the present invention is schematically shown in FIG. 17. (a) the cDNA of a recombinant BDV genome shown in FIG. 17 is a cDNA of a recombinant viral RNA having a BDV genome sequence in which the G gene and the M gene are destructed (deleted) and in which a foreign gene is inserted into the untranslated region connected to the downstream of the open reading frame of the P gene. In FIG. 17, the M surrounded by the dotted line represents the deleted M gene. Although the L gene is divided by the G gene in FIG. 3, the ORFs of the L gene are connected to each other at the point indicated by the arrow in the cDNA of a recombinant BDV genome shown in FIG. 16 and FIG. 17 because the intron of the L gene in the BDV genome is deleted as a result of partial deletion of the G gene.

The BDV genome in the present invention may be derived from any BDV virus or its variant as long as the virus or its variant belongs to the Bornaviridae (the Bornaviridae family). Examples of the virus belonging to the Bornaviridae family include a strain such as He80, H1766, Strain V, and huP2br. Examples of the variant include No/98, Bo/04w, and HOT6. Their genome sequences are available from, for example, the followings.

He80: GenBank Accession# L27077, Cubitt, B., Oldstone, C. and de la Torre, J. C. Sequence and genome organization of Borna disease virus. J. Virol. 68 (3), 1382-1396 (1994).

H1766: GenBank Accession# AJ311523, Pleschka, S., Staeheli, P., Kolodziejek, J., Richt, J. A., Nowotny, N. and Schwemmle, M. Conservation of coding potential and terminal sequences in four different isolates of Borna disease virus. J. Gen. Virol. 82 (PT 11), 2681-2690 (2001).

Strain V: GenBank Accession# U04608, Briese, T., Schneemann, A., Lewis, A. J., Park, Y. S., Kim, S., Ludwig, H. and Lipkin, W. I. Genomic organization of Borna disease virus. Proc. Natl. Acad. Sci. U.S.A. 91 (10), 4362-4366 (1994).

huP2br: GenBank Accession# AB258389, Nakamura, Y., Takahashi, H., Shoya, Y., Nakaya, T., Watanabe, M., Tomonaga, K., Iwahashi, K., Ameno, K., Momiyama, N., Taniyama, H., Sata, T., Kurata, T., de la Torre, J. C., Ikuta, K. Isolation of Borna disease virus from human brain tissue, J. Virol 74 (2000) 4601-4611.

No/98: GenBank Accession# AJ311524, Nowotny, N. and Kolodziejek, J. Isolation and characterization of a new subtype of Borna disease virus. J. Gen. Virol. 74, 5655-5658 (2000).

Bo/04w: GenBank Accession# AB246670, Watanabe, Y., Ibrahim, M. S., Hagiwara, K., Okamoto, M., Kamitani, W., Yanai, H., Ohtaki, N., Hayashi, Y., Taniyama, H., Ikuta, K. and Tomonaga, K. Characterization of a Borna disease virus field isolate which shows efficient viral propagation and transmissibility. Microbes and Infection 9 (2007) 417-427.

Part of the BDV genome sequence may be replaced with another base, deleted, or interrupted with a new base, or furthermore part of the base sequence may be transposed, as long as the function as BDV is maintained. Any of these derivatives can be used for the present invention. The above "part" may be, for example, in terms of the amino acid residues, 1 to several (usually 1 to 5, preferably 1 to 3, more preferably 1 to 2).

The cDNA of the BDV genome and the cDNA of an RNA having a BDV genome sequence in which the G gene and the like are destructed, i.e., a cDNA encoding an RNA having such a sequence can be prepared based on the viral genome information. For example, such a cDNA can be prepared from an RNA genome using a sequence reverse transcriptase. Alternatively, the cDNA of an RNA having a BDV genome sequence in which the G gene is destructed can be easily prepared by, for example, PCR using suitable primers with the cDNA of the BDV genome as a template. A cDNA of an RNA having a BDV genome sequence in which the G gene and the M gene are destructed can be easily prepared by, for example, PCR using suitable primers with, as a template, the cDNA of the BDV genome or a cDNA of an RNA having a BDV genome sequence in which the G gene is destructed. Alternatively, the cDNA can be chemically synthesized using a DNA synthesizer based on the RNA genome sequence or on the RNA genome sequence in which the G gene and the like are deleted. Further alternatively, (a) the cDNA of a recombinant BDV genome in the present invention can be obtained by a known amplifying means such as PCR. Procedures for PCR, primer preparation, and the like can be carried out according to a known gene engineering method (genetic manipulation technique).

Figure 2:
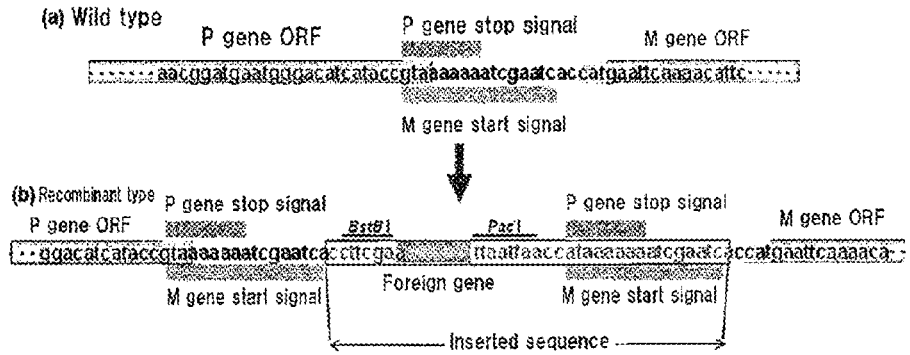

(a) the cDNA of a recombinant BDV genome is a cDNA of a recombinant viral RNA having a BDV genome sequence in which any given foreign gene is inserted into the untranslated region connected to the downstream of the ORF of the P gene. The untranslated region connected to the downstream of the ORF of the P gene is, for example, the untranslated region between the open reading frame of the P gene and the open reading frame of the M gene in the BDV genome (hereinafter sometimes simply referred to as "the untranslated region between the P gene and the M gene"). Insertion of a foreign gene in such a region can improve the recombinant virus productivity of the viral vector, i.e., the replicative efficiency of the recombinant virus produced from the viral vector and, as a result, the recombinant virus can be efficiently produced. In addition, the recombinant virus produced from (replicated by) this viral vector can efficiently express a foreign gene after introduction of the recombinant virus into a cell. Therefore, introduction of the viral vector of the present invention into a cell, or infection of a cell with the recombinant BDV produced from the viral vector enables efficient introduction of any given foreign gene into the cell, i.e., efficient expression of any given foreign gene in the cell. As shown in FIG. 2 (*a*), the stop signal sequence of the P gene (Base No. 1875 to 1882 of SEQ ID NO: 1) and the start signal sequence of the M gene (Base No. 1875 to 1890 of SEQ ID NO: 1) exist in the untranslated region connected to the downstream of the ORF of the P gene (i.e., the untranslated region between the P gene and the M gene in the BDV genome) (for example, Base No. 1875 to 1895 of the cDNA sequence of the BDV genome shown in SEQ ID NO: 1 (i.e., the bases from 1875 to 1895 of SEQ ID NO: 1)) of a cDNA of a wild-type BDV genome. The insertion site for a foreign gene in the untranslated region between the open reading frame of the P gene and the open reading frame of the M gene (for example, the region between Base No. 1878 and 1892 of SEQ ID NO: 1) is preferably a region excluding the stop signal sequence of the P gene and/or the start signal sequence of the M gene, more preferably a region excluding the stop signal sequence of the P gene and the start signal sequence of the M gene, for example, in the case of the cDNA sequence of the BDV genome shown in SEQ ID NO: 1, especially preferably the region between Base No. 1890 and 1891 of SEQ ID NO: 1.

The recombinant BDV genome in the present invention can contain a cleavage site at one end or both ends (preferably both ends) of a foreign gene. The cleavage site is preferably contained in the genome because a foreign gene can be easily inserted into the BDV genome sequence and the protein translation efficiency of a foreign gene will be increased. In the present invention, examples of the cleavage site that can be placed at one end or both ends of a foreign gene include, for the 3' end of a foreign gene, a Bst BI site, a Pac I site, an Sse8387 I site, a Swa I site, and a Kpn I site, and preferred is a Bst BI site. Examples of the cleavage site for the 5' end of a foreign gene include a Pac I site, a Bst BI site, an Sse8387 I site, a Swa I site, and a Kpn I site, and preferred is a Pac I site.

In cases where the recombinant BDV genome in the present invention contains the M gene, the cDNA of the recombinant BDV genome preferably contains a sequence containing a P-gene stop signal and M-gene start signal sequence (taaaaaaatcgaatca (SEQ ID NO: 11) both in the region between a foreign gene (including as needed a cleavage site placed at one end or both ends thereof) and the ORF of the P gene and in the region between the foreign gene (including as needed a cleavage site placed at one end or both ends thereof) and the ORF of the M gene. In the cDNA of the recombinant BDV genome in the present invention, for example, any given foreign gene is more preferably inserted in the position as shown in FIG. 2 (*b*). FIG. 2 (*b*) shows, as an example, the cDNA of the recombinant BDV genome containing the M gene. An M gene deleted viral vector also preferably has a sequence containing the P-gene stop signal and M-gene start signal sequence (SEQ ID NO: 11) downstream of a foreign gene, as shown in FIG. 2 (*b*). In the M gene deleted viral vector, the P-gene stop signal and M-gene start signal sequence placed downstream of a foreign gene, as shown in FIG. 2 (*b*), also functions as a stop signal of the foreign gene and as a start signal of the L gene. FIG. 2 (*b*) shows, as an example, the case where a Bst BI site and a Pac I site are inserted in the 3' end and the 5' end of a foreign gene, respectively, but the cleavage sites placed at both ends of a foreign gene are not limited to thereto.

The kind and length of a foreign gene in the present invention are not specifically limited, and any desired gene can be used depending on the purpose. Examples of the foreign gene include a cDNA of a gene encoding a protein or a peptide; a cDNA encoding an siRNA, a short hairpin RNA (shRNA), and a microRNA (miRNA); and a cDNA encoding an RNA aptamer. For the viral vector of the present invention, one or more foreign genes can be used.

(b) DNA Encoding Ribozyme

The DNA encoding a ribozyme may have any sequence as long as the ribozyme can cut any given foreign gene transcribed from (a) the cDNA of a recombinant virus. Examples of (b) include a DNA such as a cDNA encoding such a ribozyme as a hammer head ribozyme (HamRz), a hepatitis δ virus ribozyme (HDVRz), a hairpin ribozyme, and an artificial ribozyme. Besides these, a DNA such as a cDNA encoding a modified form of the above ribozyme can also be used as long as it has a ribozyme activity. Examples of the modified ribozyme include a polynucleotide having a consensus sequence, containing a base sequence in which 1 to several ("several" means for example, 10, preferably 5, more preferably 3, further preferably 2) bases are replaced, deleted, or added, and having a function as a ribozyme. Inter alia, as the ribozyme in the present invention, preferred are a hammer head ribozyme (HamRz) and a hepatitis δ virus ribozyme (HDVRz). Especially preferably, (b1) a DNA (preferably a cDNA) encoding HamRz is placed upstream of (a) the cDNA of a recombinant BDV genome, i.e., at the 3' end thereof, and (b2) a DNA (preferably a cDNA) sequence encoding HDVRz is placed downstream of (a), i.e., at the 5' end thereof. This improves the expression efficiency of a foreign gene in a cell.

The base sequence of HamRz is described in Yanai et al., Microbes and Infections 8 (2006) 1522-1529; Mercier et al., J. Virol. 76 (2002) 2024-2027; Inoue et al., J. Virol. Methods 107 (2003) 229-236; and the like.

The base sequence of HDVRz is described in Ferre-D' Amare, A. R., Zhou, K. and Doudna, J. A. Crystal structure of a hepatitis delta virus ribozyme. Nature 395 (6702), 567-574 (1998); and the like. The cDNAs encoding the HamRz base sequence described in these literatures can be used for the present invention. Especially preferred base sequences of HamRz and HDVRz for the present invention are shown below.

```
HamRz:
                                                 (SEQ ID NO: 2)
5'-UUGUAGCCGUCUGAUGAGUCCGUGAGGACGAAACUAUAGGAAAGGA

AUUCCUAUAGUCAGCGCUACAACAAA-3'

HDVRz:
                                                 (SEQ ID NO: 3)
5'-GGCCGGCAUGGUCCCAGCCUCCUCGCUGGCGCCGGCUGGGCAACAC

CAUUGCACUCCGGUGGCGAAUGGGAC-3'
```

(c) Promoter Sequence

Examples of (c) the promoter sequence in the present invention include an RNA polymerase II promoter sequence, an RNA polymerase I promoter sequence, and a T7 polymerase promoter sequence. Among these, preferred is an RNA polymerase II promoter sequence. Examples of the RNA polymerase II promoter include a CMV promoter and a CAGGS promoter. Among these, especially preferred is a CAGGS promoter. Such a promoter sequence is described in, for example, J. A. Sawicki, R. J. Morris, B. Monks, K. Sakai, J. Miyazaki, A composite CMV-IE enhancer/b-actin promoter is ubiquitously expressed in mouse cutaneous epithelium, Exp. Cell Res. 244 (1998) 367-369.

In a preferred embodiment of the present invention, (b1) the cDNA encoding a hammer head ribozyme is placed upstream of (a) the cDNA of a recombinant viral RNA (the cDNA of a recombinant BDV genome) and (b2) the cDNA sequence encoding a hepatitis δ virus ribozyme is placed downstream of (a). In this embodiment, (a) and (b) are placed downstream of (c) the RNA polymerase II promoter.

(d) Other Base Sequences

The viral vector of the present invention can contain the whole or part of SV40 virus replication origin/promoter region sequence. In cases where the viral vector contains the whole or part of SV40 virus replication origin/promoter region sequence, the sequence is preferably placed downstream of (a) and (b). As the part of the SV40 virus DNA replication origin/promoter region sequence, preferred is a fragment consisting of 113 bases at the 5' end in the SV40 replication origin/promoter region.

The SV40 virus replication origin/promoter region sequence (SEQ ID NO: 4) is described in, for example, D. A. Dean, B. S. Dean, S. Muller, L. C. Smith, Sequence requirements for plasmid nuclear import, Exp. Cell. Res. 253 (1999) 713-722, and the like.

The viral vector of the present invention, as long as it exerts the effect of the present invention, can further contain one or a plurality of factors that are advantageous to protein expression, for example, one or a plurality of nucleic acid sequences encoding an enhancer, an activator (for example, a transacting factor), a chaperon, and a processing protease. The viral vector of the present invention may also have any of factors that are functional in a selected cell.

The viral vector of the present invention may be a linear DNA or a circular DNA, but when the viral vector is introduced into a cell, the viral vector is preferably in a circular form. Examples of the circular viral vector include a marketed plasmid vector modified so that the above DNA sequences (a), (b), and (c) essential for the viral vector of the present invention, as well as the above DNA (d) as needed, are placed in the above predetermined order. The marketed plasmid vector may be any vector as long as it can self-replicate in a cell into which the vector is to be introduced, and examples of the vector include pBluescript SKII (−), pCAGGS, pCXN2, and pCDNA3.1.

2. Preparation Process for Viral Vector

The preparation process for the viral vector of the present invention is not specifically limited, and any gene engineering method known per se may be used. For example, according to the method described in 2.2 Plasmid construction of "Materials and methods" in Yanai et al., Microbes and Infection 8 (2006) 1522-1529, the self-replicating (persistently infecting) viral vector of the present invention can be prepared by, using the BDV genome sequence instead of the CAT gene, inserting a target foreign gene into the untranslated region connected to the downstream of the P gene (the untranslated region between the P gene and the M gene). The viral vector prepared by the above process has, as (a) the cDNA of a recombinant viral RNA, a cDNA encoding a recombinant Borna disease virus genome in which a foreign gene is inserted into the untranslated region between the open reading frame of the P gene and the open reading frame of the M gene (for example, a cDNA of a recombinant virus having the construct schematically shown in FIG. 3).

The G gene deleted viral vector and the G gene and M gene deleted viral vector can be prepared by a gene engineering method known per se. For example, the G gene deleted viral vector in the present invention can be prepared by introducing a deletion mutation or the like into the G gene through PCR or the like using, as a template, a self-replicating viral vector having, as (a) the cDNA of a recombinant viral RNA, a cDNA encoding a recombinant BDV genome in which a foreign gene is inserted into the untranslated region between the open reading frame of the P gene and the open reading frame of the M gene (for example, (a) the cDNA of a recombinant viral RNA having the construct schematically shown in FIG. 3). Preferably, in the preparation of the G gene deleted viral vector, PCR is similarly performed for further deletion of the intron of the L gene, to give a more preferred G gene deleted viral vector of the present invention. Similarly, the G gene and M gene deleted viral vector can be prepared by deleting the M gene through PCR or the like using the G gene deleted viral vector as a template.

In cases where the viral vector is in a linear form, a linear viral vector can be prepared from the above circular viral vector by selecting as appropriate, according to the kind of the vector, a restriction enzyme that cuts one site in a region other than the region of (a) the cDNA of a recombinant BDV genome, the region of (c) the promoter sequence, and other signal sequence regions necessary for protein expression; and cutting the circular viral vector with the restriction enzyme.

Examples of a process for introducing a foreign gene contained in the viral vector of the present invention into a target cell include a method involving introduction of the viral vector together with the helper plasmid described below into a target cell, a method involving infection of a target cell with the recombinant virus produced from the viral vector. Among these, preferred is the method using the recombinant virus produced from the viral vector. The recombinant virus produced from the viral vector of the present invention is a recombinant BDV having an RNA encoded not by a wild-type BDV genome but by the above viral vector.

3. Recombinant Virus

The recombinant virus containing an RNA encoded by the above viral vector is also one aspect of the present invention. The recombinant virus preferably contains an RNA encoded by the viral vector, the N protein of BDV, the P protein of BDV, and the L protein of BDV. The recombinant virus of the present invention is a persistently infecting recombinant virus, which can persistently express a foreign gene after infection of a cell, due to the above recombinant BDV genome contained therein. The recombinant virus may contain as needed the G protein of BDV, or the coat protein of another virus, and may further contain the M protein of BDV. The coat gene in the present invention is a gene encoding the coat protein of a virus. The coat protein of BDV is encoded by the G gene.

The recombinant virus of the present invention can be prepared by, for example, a process comprising the steps of introducing, as a helper plasmid, a plasmid or plasmid group expressing the N gene, the P gene, and the L gene of BDV together with the above viral vector into an in vitro cell, and culturing the cell having the introduced viral vector and helper plasmid to produce a recombinant virus. Such a preparation process of the recombinant virus is also one aspect of the present invention. By the above process, the recombinant virus can be produced in vitro. The in vitro cell into which the viral vector and the helper plasmid are to be introduced is usually a cultured cell.

In cases where the G gene deleted viral vector is used in the process of the present invention, preferably a plasmid expressing the coat gene of a virus is further introduced as a helper plasmid into an in vitro cell. The coat gene of a virus is selected as appropriate according to a target cell into which a foreign gene is to be introduced, and the coat gene may be the G gene of BDV or the coat gene of a virus other than BDV. In cases where the G gene and M gene deleted viral vector is used, preferably a plasmid expressing the M gene of BDV is further introduced as a helper plasmid into a cell. That is, in cases where the G gene and M gene deleted viral vector is used, preferably a plasmid expressing the coat gene of a virus and a plasmid expressing the M gene of BDV are further introduced together with the above plasmid or plasmid group expressing the N gene, the P gene, and the L gene of BDV into an in vitro cell.

The helper plasmid may be any plasmid as long as it can express the N gene, the P gene, the L gene, or the M gene of BDV, or the coat gene of a virus. Two or more of these genes may be contained in a single plasmid, and these genes may be separately contained in different plasmids. For example, as the plasmid(s) expressing the N gene, the P gene, and the L gene of BDV, any of the plasmid or plasmid groups of the following (1) to (4) is used as appropriate:

(1) a plasmid expressing the N gene of BDV, a plasmid expressing the P gene of BDV, and a plasmid expressing the L gene of BDV;

(2) a plasmid expressing the N gene and the P gene of BDV, and a plasmid expressing the L gene of BDV;

(3) a plasmid expressing the N gene and the L gene of BDV, and a plasmid expressing the P gene of BDV; and (4) a plasmid expressing the N gene, the L gene, and the P gene of BDV.

The helper plasmid provides a viral protein required to replicate the BDV genome and thus, by introducing the viral vector together with the helper plasmid into a cell, an infectious recombinant virus can be produced. Among the above plasmids (plasmid groups) (1) to (4) expressing the N gene, the P gene, and the L gene of BDV as the helper plasmid, preferred is any of the plasmid groups (1) to (3). The viral vector used for the process for preparing the recombinant virus of the present invention and a preferred embodiment thereof are the same as described above.

The helper plasmid in the present invention may be any plasmid as long as, after introduction together with the above viral vector into a cell, the plasmid can express the N gene, the P gene, and the L gene of BDV in the cell. For example, the plasmid expressing the N gene of BDV is preferably a plasmid in which the cDNA of the N gene of BDV is placed downstream of the promoter sequence. The plasmid expressing the P gene of BDV is preferably a plasmid in which the cDNA of the P gene of BDV is placed downstream of the promoter sequence. The plasmid expressing the L gene of BDV is preferably a plasmid in which the cDNA of the L gene of BDV is placed downstream of the promoter sequence.

The plasmid expressing the N gene and the P gene of BDV is preferably a plasmid in which the cDNA of the N gene and the cDNA of the P gene of BDV are placed downstream of the promoter sequence in this order. The plasmid expressing the N gene and the L gene of BDV is preferably a plasmid in which the cDNA of the N gene and the cDNA of the L gene of BDV are placed downstream of the promoter sequence in this order. The plasmid expressing the N gene, the L gene, and the P gene of BDV is preferably a plasmid in which the cDNA of the N gene, the cDNA of the L gene, and the cDNA of the P gene of BDV are placed downstream of the promoter sequence in this order.

In cases where the viral vector is the G gene deleted viral vector, the helper plasmid may be any plasmid as long as, after introduction together with the G gene deleted viral vector into a cell, the plasmid can express the N gene, the P gene, and the L gene of BDV as well as the coat gene of a virus in the cell. In cases where the viral vector is the G gene and M gene deleted viral vector, the helper plasmid may be any plasmid as long as it can further express the M gene of BDV in the cell.

The plasmid expressing the coat gene of a virus and the plasmid expressing the M gene of BDV can be used together with any of the above plasmids (plasmid groups) (1) to (4). The plasmid expressing the coat gene may be a plasmid expressing the coat gene of a virus in addition to one or more genes selected from the group consisting of the N gene, the L gene, and the P gene of BDV. The plasmid expressing the coat gene is preferably a plasmid in which the cDNA of the coat gene is placed downstream of the promoter sequence.

A coat protein encoded by a coat gene such as the G gene of BDV is usually a transmembrane protein and contains, in its amino acid sequence, a region positioned outside of a cell (extracellular sequence), a transmembrane region (transmembrane sequence), and a region positioned inside of a cell (intracellular sequence). The coat gene used for the helper plasmid may be the G gene of BDV, or the coat gene of any enveloped virus that utilize the host cell membrane to form a coat, for example, vesicular stomatitis virus, rabies virus, measles virus, a retrovirus, or the like. A preferred coat gene used for the helper plasmid is a gene encoding the intracellular sequence of the G protein of BDV as an intracellular sequence. That is, the coat gene in the present invention preferably a gene encoding a protein having the intracellular sequence of the G protein of BDV as an intracellular sequence and having the extracellular sequence and the transmembrane sequence of the coat protein of any given virus (BDV or a virus other than BDV). The intracellular sequence of the G protein of BDV as an intracellular sequence can improve the recombinant viral production efficiency. For example, in cases where the coat gene of a virus other than BDV is used for the helper plasmid, a gene sequence encoding the intracellular sequence of the coat gene is preferably replaced with the sequence encoding the intracellular sequence of the G protein of BDV by a known gene engineering method.

Use of a coat gene encoding the extracellular sequence and the transmembrane sequence of a virus other than BDV for the helper plasmid can alter the cell tropism of a virus to be produced according to the viral origin of the coat gene. For example, in cases where the recombinant virus is used to infect an epithelium cell, a respiratory cell, or the like, preferably used is a helper plasmid expressing a coat gene encoding the extracellular sequence and the transmembrane sequence of the coat protein of a virus that has a high tropism for an epithelium cell, a respiratory cell, or the like (for example, measles virus, Sendai virus, vesicular stomatitis virus, or the like), and also encoding the intracellular sequence of the G protein of BDV.

A plasmid that can also be used as the plasmid expressing the M gene is a plasmid expressing the M gene of BDV in addition to one or more genes selected from the group consisting of the N gene, the L gene, the P gene of BDV, and the coat gene of a virus. The plasmid expressing the M gene is preferably a plasmid in which the cDNA of the M gene of BDV is placed downstream of the promoter sequence.

The cDNA of the N gene, the cDNA of the P gene, and the cDNA of the L gene of BDV can be prepared based on the sequence information of the N gene, the P gene, and the L gene of BDV, respectively. The cDNA of the M gene and the cDNA of the G gene of BDV can be prepared based on the sequence information of the M gene, and the G gene of BDV, respectively. For example, such a cDNA can be prepared from an RNA genome using a sequence reverse transcriptase. The cDNA can be chemically synthesized using a DNA synthesizer based on an RNA sequence.

Genes that can be used as the N gene, the P gene, the L gene, the M gene, or the G gene of BDV include a gene having a sequence described in, for example, Cubitt, B., Oldstone, C. and de la Torre, J. C. Sequence and genome organization of Borna disease virus. J. Viral. 68 (3), 1382-1396 (1994), which is mentioned above. As these genes, an RNA synthesized based on the above sequence can also be used. The fragments of these genes can also be obtained by hybridization and PCR based on an amino acid sequence conserved among the N proteins, the P proteins, the L proteins, the M proteins, or the G proteins of BDVs. The fragments of these genes can also be obtained by degenerate RT-PCR using a mixed primer designed based on other known sequences of the N gene, the P gene, the L gene, the M gene, and the G gene of BDV. The base sequence of the obtained fragments can be determined by a usual method. Part of the base sequence of the N gene, the P gene, the L gene, the M gene, or the G gene of BDV in the present invention may be replaced with another base, deleted, or interrupted with a new base, or furthermore part of the base sequence may be transposed, as long as the protein encoded by the corresponding gene has the function of the N protein, the P protein, the L protein, or the M protein of BDV. Any of these derivatives can be used for the present invention. The above "part" may be, for example, in terms of the amino acid residues, 1 to several (1 to 5, preferably 1 to 3, more preferably 1 to 2).

The N gene of BDV in the present invention may be, for example, an RNA encoding a polypeptide having at least about 90%, preferably about 95% or more, more preferably about 98% or more sequence homology with the N gene of BDV, and having the function of the N protein. The P gene of BDV in the present invention may be, for example, an RNA encoding a polypeptide having at least about 90%, preferably about 95% or more, more preferably about 98% or more sequence homology with the P gene of BDV, and having the function of the P protein. The L gene of BDV in the present invention may be, for example, an RNA encoding a polypeptide having at least about 90%, preferably about 95% or more, more preferably about 98% or more sequence homology with the L gene of BDV, and having the function of the L protein. The G gene of BDV in the present invention may be, for example, an RNA encoding a polypeptide having at least about 90%, preferably about 95% or more, more preferably about 98% or more sequence homology with the G gene of BDV, and having the function of the G protein. The M gene of BDV in the present invention may be, for example, an RNA encoding a polypeptide having at least about 90%, preferably about 95% or more, more preferably about 98% or more sequence homology with the M gene of BDV, and having the function of the M protein. The sequence homology is determined by CLUSTALW, GCG program, GENETYX, or BLAST search.

The coat gene of a virus other than BDV such as vesicular stomatitis virus, rabies virus, measles virus, and a retrovirus may be, for example, the gene sequence registered in GenBank No:J 02428.1 for the coat gene of vesicular stomatitis virus, the gene sequence registered in GenBank No:AB044824.1 for the coat gene of rabies virus, or the like. Preferred sequence is a sequence which is derived from such a coat gene and encodes the extracellular sequence and the transmembrane sequence of a coat protein. The coat gene-derived sequence encoding the extracellular sequence and the transmembrane sequence of a coat protein is described in Garry RF. Proteomics computational analyses suggest that the bornavirus glycoprotein is a class III viral fusion protein (γ penetrene). Virol J. 145(6), Sep. 18 (2009), and the like. An RNA synthesized based on the above sequence can also be used as the coat gene. The coat gene of a virus in the present invention may also be, for example, an RNA encoding a polypeptide having at least about 90%, preferably about 95% or more, more preferably about 98% or more sequence homology with the coat gene, and having the function of the coat protein.

The helper plasmid in a linear form might not cause any problems when it is introduced into a cell, but preferably the helper plasmid is in a circular form. A circular helper plasmid, for example, contains the cDNA of the above protein and a promoter sequence that are essential sequences for the helper plasmid in the present invention, and also can contain one or a plurality of factors that are advantageous to protein expression, for example, one or a plurality of nucleic acid sequences encoding an enhancer, an activator (for example, a transacting factor), a chaperon, and a processing protease. The helper plasmid may also have any of factors that are functional in a selected cell. The helper plasmid is preferably constructed using a marketed plasmid vector self-replicating in a cell into which the helper plasmid is to be introduced, and examples of the marketed plasmid vector include pCAGGS, pCXN2, and pCDNA3.1. The promoter sequence contained in the helper plasmid is preferably an RNA polymerase II promoter.

The above helper plasmid can be prepared by a gene engineering method known per se. For example, the plasmid expressing the N gene of BDV, the plasmid expressing the P gene of BDV, and the plasmid expressing the L gene of BDV can be prepared by a method described in 2.2 Plasmid construction of "Materials and methods" in Yanai et al., Microbes and Infection 8 (2006), 1522-1529.

The plasmid expressing the N gene and the P gene of BDV can be prepared by, for example, selecting as appropriate a restriction enzyme that does not cut the cDNA sequence of the N gene and any signal sequence such as the promoter sequence, from unique restriction enzyme sequence regions downstream of the cDNA sequence of the N gene in a plasmid expressing the N gene of BDV, and inserting the cDNA of the P gene of BDV into the cleavage site of the selected restriction enzyme. The plasmid expressing the N gene and the L gene of BDV can prepared by, for example, selecting as appropriate a restriction enzyme that does not cut the cDNA sequence of the N gene and any signal sequence such as the promoter sequence, from unique restriction enzyme sequence regions downstream of the cDNA sequence of the N gene in a plasmid expressing the N gene of BDV, and inserting the cDNA of the L gene of BDV into the cleavage site of the selected restriction enzyme. It is also possible to insert a promoter sequence, an internal ribosome entry site, or the like that promotes the expression of the L gene or the P gene, into the region between the cDNA region of the N gene and a region into which the cDNA of the L gene or the P gene is inserted.

Figure 21:
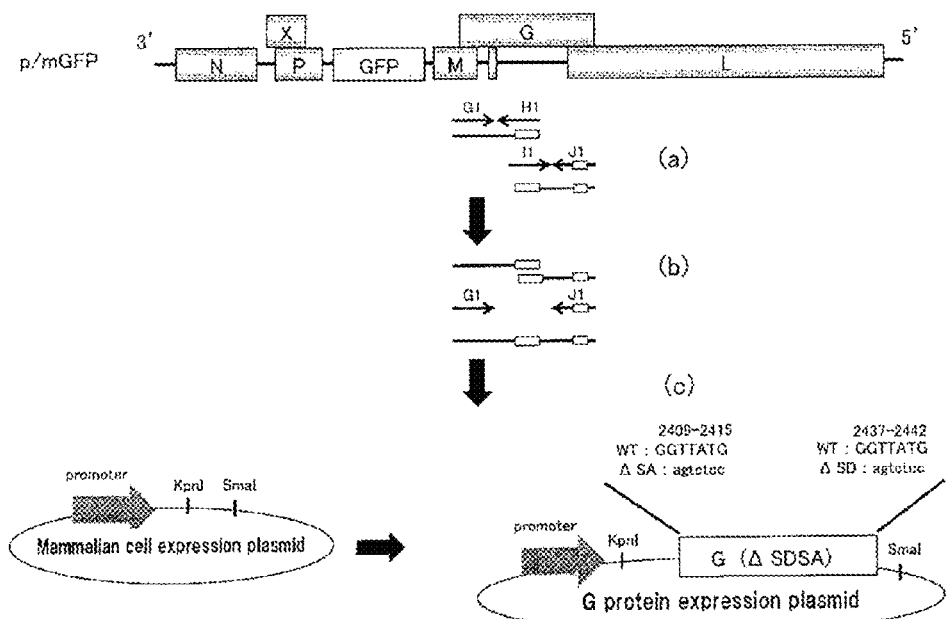
Figure 28:
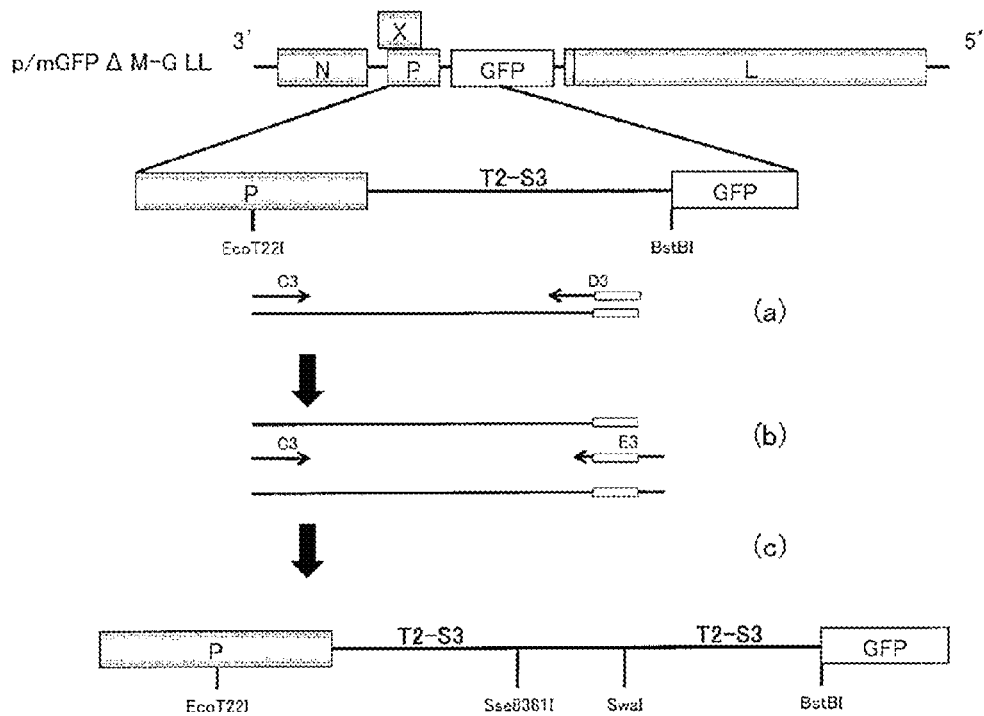

The plasmid expressing the G gene of BDV can be prepared using the cDNA of the G gene of BDV instead of the cDNA of the N gene of BDV in the preparation process for the helper plasmid expressing the N gene, the L gene, or the P gene of BDV. For example, the plasmid expressing the G gene of BDV can be prepared by the process shown, as an example, in Example 7 and FIG. 21. The plasmid expressing the M gene of BDV can be prepared according to, for example, the process described in the instruction manual attached to pEF4/myc-His A, B, and C (Invitrogen).

The helper plasmid expressing a coat gene encoding the extracellular sequence and the transmembrane sequence of the coat protein of a virus other than BDV and also encoding the intracellular sequence of the G protein of BDV can be prepared by, for example, PCR, using a plasmid expressing the coat gene of a virus other than BDV as a template and suitable primers, for replacement of a sequence encoding the intracellular sequence of the coat gene with a sequence encoding the intracellular sequence of the G protein of BDV. Such a helper plasmid can be prepared by the process shown, as an example, in Example 8 and FIG. 25. The gene sequence encoding the intracellular sequence of the G protein of BDV is, for example, the 3712th to 3747th sequence of the cDNA sequence of the BDV genome shown in SEQ ID NO: 1 (the 3712th to 3747th bases of SEQ ID NO: 1).

Introduction of the above viral vector into a cell can be carried out, for example, using a vector composition containing the viral vector. The vector composition may contain the helper plasmid besides the viral vector. The vector composition may contain, besides the viral vector and the helper plasmid, other components such as a suitable buffer solution, a phosphate buffered saline, and a standard solution for cell culture according to the introducing method, the target for introduction, or the like.

The amount of the above viral vector in the vector composition is determined as appropriate according to the infection method, and the target for infection, but preferably the vector composition contains, for example, about 0.25 to 2.0 μg/μL of the viral vector in terms of the DNA concentration.

The amount of each helper plasmid in the vector composition is preferably, for example, about 0.0125 to 0.125 μg relative to 1 μg of the above viral vector.

The method for introducing the above viral vector and the above helper plasmid into a cell in vitro is not specifically limited and, for example, a method known per se using a marketed transfection reagent can be used. Examples of the marketed transfection reagent include FuGENE (registered trademark) 6 transfection reagent (Roche Molecular Diagnostics, Pleasanton, Calif.), but are not specifically limited thereto. In particular, the viral vector and the helper plasmid can be introduced into a cell by, for example, adding an appropriate amount of a marketed transfection reagent to a vector composition containing the above amounts of the viral vector and the helper plasmid, as well as a buffer solution, and the like; and adding the resulting mixture to cells, which is usually about $10^3$ to $10^7$ cells, preferably about $10^4$ to $10^7$ cells relative per 1 µg of the viral vector. The viral vector and the helper plasmid may be introduced into a cell simultaneously or separately. The order for the separate introduction is not specifically limited.

The cell into which the viral vector is to be introduced may be any cell as long as it is a mammalian cultured cell that can produce the recombinant virus in the present invention as a result of the introduction of the viral vector. Examples of such a cell include 293T cells, which are derived from a human kidney, and BHK cells.

In cases where the G gene deleted viral vector is used, a preferred cell that can be used is a cell that can constantly express the coat gene used for the helper plasmid expressing a coat gene. Such a cell can be prepared by, for example, introducing the coat gene into a cell such as 293T cells and BHK cells using various kinds of plasmids expressing the coat gene. The plasmid expressing the coat gene is usually produced by introducing the coat gene into various kinds of plasmids according to the method described in the instruction manual attached to the various kinds of expression plasmids. The above helper plasmid expressing a coat gene can also be preferably used as such a plasmid expressing the coat gene. In cases where the G gene and M gene deleted viral vector is used, a preferred cell that can be used is a cell that can constantly express the coat gene used for the helper plasmid expressing a coat gene and express the M gene of BDV. Such a cell can be prepared by, for example, introducing the coat gene and the M gene of BDV into a cell such as 293T cells and BHK cells using various kinds of plasmids expressing the coat gene and the M gene of BDV in the same manner as described above. The plasmid expressing the coat gene and the plasmid expressing the M gene of BDV are usually easily produced by introducing the coat gene and the M gene of BDV separately into various kinds of plasmids according to the method described in the instruction manual attached to the various kinds of expression plasmids. The above helper plasmid expressing a coat gene, the above helper plasmid expressing the M gene of BDV, or the like can also be preferably used as such a plasmid expressing the coat gene and such a plasmid expressing the M gene of BDV.

Next, the cell having the introduced viral vector is cultured to produce a recombinant virus. The culture conditions such as the culture medium for recombinant virus production, the culture temperature, and the culture time are determined as appropriate depending on the kind of the cell. In cases where 293T cells or BHK cells are used, the culture temperature is usually about 36 to 37° C. The culture medium is preferably a Dulbecco Modified Eagle Medium (DMEM). The culture time is usually about 24 to 96 hours, preferably about 36 to 48 hours.

The culture of the cell having the introduced viral vector produces a recombinant virus containing an RNA encoded by the viral vector, the N protein, the P protein, and the L protein of BDV. In cases where a helper plasmid expressing the coat gene of a virus is further introduced with the viral vector, the culture of the cell produces a recombinant virus containing the coat protein encoded by the coat gene besides the RNA encoded by the viral vector, the N protein, the P protein, and the L protein of BDV. In cases where a helper plasmid expressing the coat gene of a virus and a helper plasmid expressing the M gene of BDV are further introduced with the viral vector, the culture of the cell produces a recombinant virus containing the coat protein encoded by the coat gene and the M protein of BDV besides the RNA encoded by the viral vector, the N protein, the P protein, and the L protein of BDV.

The production of a recombinant virus in the cell having the introduced viral vector can be confirmed by, for example, recovering, by centrifugation or the like, the supernatant of the culture medium in which the cell was cultured, and infecting, using the supernatant, a cell that BDV can infect, for example, a monkey kidney (Vero) cell, a rat glial (C6) cell, a human glial (OL) cell, or the like. The confirmation of the production of a recombinant virus may be carried out after the step (described below) of co-culturing the recombinant virus-producing cell with a cell having a high growth rate.

For example, the confirmation of the production of a recombinant virus can be carried out by quantitative analysis for the expression of a foreign gene (for example, GFP or the like) in an infected cell. The confirmation of the production of a persistently infecting virus can be carried out by quantitative analysis for the expression of a foreign gene (for example, GFP or the like) in an infected cell, together with the confirmation of the production of recombinant virus particles of the next generation in the culture supernatant. The confirmation of the production of the recombinant virus particles of the next generation in the culture supernatant can be carried out by, for example, recovering the supernatant by centrifugation or the like, infecting another cell using the supernatant, and analyzing the expression of the foreign gene derived from the recombinant virus in the cell.

In the preparation process of the present invention, for the purpose of efficient growth of the virus, the step of co-culturing the recombinant virus-producing cell (for example, 293T cells, BHK cells, or the like) with a cell having a high growth rate is preferably carried out after the viral vector or the like is introduced into a cell to produce a recombinant virus, as described above. When the recombinant virus-producing cell is co-cultured with a cell having a high growth rate, the infectious virus infects the cell having a high growth rate. In culture of the infected cell having a high growth rate, the virus grows as the cell grows and thus the recombinant virus can be efficiently increased. As the cell having a high growth rate, preferred are, for example, Vero cells or the like. The mixing ratio of the recombinant virus-producing cell and the cell having a high growth rate is, for example, usually about 0.1 to 10 cells, preferably about 0.2 to 2 cells of the cell having a high growth rate, relative to 1 cell of the recombinant virus-producing cell. After co-culturing, the culture conditions for the cell having a high growth rate are not specifically limited. For example, in cases where Vero cells are used, the cells are cultured in a Dulbecco Modified Eagle Medium (DMEM) at a culture temperature of usually about 36 to 37° C. for usually about 3 days to 5 weeks, preferably about 3 days to 3 weeks.

In cases where the G gene deleted viral vector is used, the cell having a high growth rate is preferably a cell that can constantly express the coat gene used for the helper plasmid expressing a coat gene. Such a cell can be prepared by, for example, introducing the coat gene into a cell such as Vero cells using various kinds of plasmids expressing the coat gene. In cases where the G gene and M gene deleted viral vector is used, the cell having a high growth rate is preferably a cell that can constantly express the coat gene used for the helper plasmid expressing a coat gene and express the M gene of BDV. Such a cell can be prepared by, for example, introducing the coat gene and the M gene of BDV into a cell such as Vero cells using a plasmid expressing the coat gene and a plasmid expressing the M gene of BDV. The plasmid expressing the coat gene and the plasmid expressing the M gene of BDV are usually easily produced by introducing the coat gene and the M gene of BDV separately into various kinds of plasmids according to the method described in the instruction manual attached to the various kinds of expression plasmids. The above helper plasmid expressing a coat gene, the above helper plasmid expressing the M gene of BDV, or the like can also be preferably used as the plasmid expressing the coat gene and the plasmid expressing the M gene of BDV.

In the preparation process of the present invention, the step of purifying the recombinant virus is preferably carried out after the production (and growth) of the recombinant virus in a cell. The purification method is not specifically limited, and can be selected as appropriate from methods known per se depending on the target for infection.

Infection of a cultured cell with the recombinant virus can be carried out by, for example, producing (and increasing) the recombinant virus as described above, recovering the supernatant of the cultured cell that has produced the recombinant virus, and disrupting the cell. The disruption of the cell can be carried out, for example, by freezing and lysing, or using an ultrasonic homogenizer. The disrupted component of the cell is then removed from the disrupted cell solution. The removal of the disrupted component of the cell from the disrupted cell solution can be carried out by centrifugation (for example, 4° C., 800 g for 10 minutes) or the like. After removal of the disruption component of the cell, the resulting solution is filtrated through a filtration membrane having a pore size of 0.22 or 0.45 μm to give a supernatant containing the recombinant virus. This supernatant can be used to infect a cultured cell with the recombinant virus. The supernatant containing the recombinant virus can also be used after concentration by a known method.

In cases where the recombinant virus is used to infect a living cell (a cell in an animal subject), the supernatant containing the recombinant virus is preferably highly purified to give virus particles by concentration gradient ultracentrifugation with an ultracentrifuge. The purified virus particles are, for example, suspended in a phosphate buffered saline and diluted, and a suitable amount of the virus particles is then used to infect an animal.

4. Introducing Process of Foreign Gene

The foreign gene integrated into the above recombinant virus can be introduced into a cell or a living body using the virus to infect the cell. Such a process for introducing a foreign gene, the process comprising the steps of infecting an in vitro cell or an animal with the above recombinant virus or a recombinant virus prepared by the above process, is also one aspect of the present invention.

The animal to be infected with the recombinant virus is not specifically limited, and examples thereof include mammals, birds, reptiles, and amphibians. Among these, preferred are mammals such as humans, monkeys, horses, dogs, cats, pigs, sheep, goats, rats, mice, rabbits, and cattle; more preferred are rats, mice, or humans; and further preferred are mice or humans. The cell of such an animal is preferably used as a cell to be infected with the recombinant virus. Since BDV is a neurotropic virus, the cell is preferably mammalian nerve system cells, and among these, the cell is especially preferably a cranial nerve system cell. Inter alia, preferred is a rat, mouse, or human nerve system cell. The cell may be a cultured cell or a living cell. Examples of the mammalian cranial nerve system cell include a glia cell, a neuron of a cerebral cortex, a hippocampal neuron, a cerebellar neuron, and a mesencephalic neuron. As the cultured cell of a mammalian cranial nerve system cell, preferred are an OL cell, a C6 cell, a U373 cell, a N2a cell, a N18 cell, a PC12 cell, and a SK-N-SH cell.

The recombinant virus produced by using the G gene deleted viral vector together with, as the helper plasmid, a plasmid expressing the coat gene of a virus exhibits an infection tropism associated with the viral origin of the coat gene. For example, in cases where the G gene of BDV is used for the helper plasmid, a recombinant virus to be obtained exhibits an infection tropism for a cranial nerve system cell, and accordingly the recombinant virus is preferably used to introduce a foreign gene into a cranial nerve system cell. In cases where the coat gene of a virus other than BDV (preferably a coat gene encoding the extracellular sequence and the transmembrane sequence of the coat protein of a virus other than BDV and also encoding the intracellular sequence of the G protein of BDV) is used for the helper plasmid, a recombinant virus to be obtained can be preferably used to infect a cell for which the virus exhibits an infection tropism.

The method for infecting a cell with the recombinant virus in vitro preferably comprises, for example, in the case of infecting a cultured cell, the step of preparing a diluted viral solution by serially diluting the supernatant containing the recombinant virus obtained by the above purification method, with a culture medium such as a Dulbecco Modified Eagle Medium or a phosphate buffered saline. The concentration of the recombinant virus in the diluted viral solution is determined as appropriate depending on the kind of the cell to be infected with the virus, or the like, and, for example, in cases where the cell is a mammalian neuron or the like, the concentration is usually about 0.01 to 10 MOI (multiplicity of infection, infectivity titer) (the amount means that there exist 0.01 to 10 infectious virus particles per cell), preferably about 1 to 10 MOI. The cell is to be infected with the recombinant virus using such a diluted viral solution.

In cases where the recombinant virus is used to infect a living cell (an animal), preferably, highly purified virus particles as described above are suspend in, for example, a phosphate buffered saline and diluted with a phosphate buffered saline, and a suitable amount of the virus particles is then used to infect an animal. The concentration of the recombinant virus in the diluted viral solution is determined as appropriate depending on the target for infection. For example, in cases where the target for infection is a mammalian neuron, the subject is preferably inoculated with the diluted recombinant viral solution having a virus titer of about $10^{-1}$ to $10^{9}$ FFU (focus-forming unit). In cases where a mouse or a rat is inoculated with the diluted recombinant viral solution, preferably the virus titer of the diluted solution is usually about $10^{-1}$ to $10^{7}$ FFU. In cases where a dog, a cat, or a human is inoculated with the diluted recombinant viral solution, preferably the virus titer is usually about 10 to $10^{8}$ FFU. In cases where a horse or cattle are inoculated with the diluted recombinant viral solution, preferably the virus titer is usually about $10^{5}$ to $10^{12}$ FFU. In cases where a human is inoculated with the diluted recombinant viral solution, preferably the virus titer is usually about $10^{5}$ to $10^{9}$ FFU. The foreign gene transfer agent described below is also preferably used for infection of a living cell with the recombinant virus.

For example, in cases where a mammalian cranial nerve system cell is infected with the recombinant virus, the diluted recombinant viral solution is preferably administered to the nasal cavity of the mammal. In cases where the cranial nerve system cell of a mouse, a rat, or the like is infected with the recombinant virus in an animal experiment, the diluted recombinant viral solution can also be administered directly to the brain of the animal.

The inoculum dose of the recombinant virus is usually about 5 µL to 1 mL of the diluted solution containing the above concentration of the recombinant virus per dose for intranasal inoculation, and usually about 1 to 50 µL per dose for intracerebral inoculation. The inoculum dose of the recombinant virus in an animal is determined as appropriate depending on the weight or the like of the animal. For example, in cases where a mouse or a rat is intranasally inoculated with the diluted solution containing the above concentration of the recombinant virus, the inoculum dose is usually about 5 to 200 µL per dose, preferably about 10 to 100 µL per dose.

In cases where a living cell other than a cranial nerve system cell is infected with the recombinant virus, the diluted recombinant viral solution is preferably parenterally administered. For example, preferred is intraperitoneal inoculation, intravascular inoculation, intramuscular inoculation, or the like for a mammal.

The inoculum dose of the recombinant virus is determined as appropriate depending on the inoculation site or the like and is not specifically limited. For example, in cases where the virus titer of the diluted recombinant viral solution is about $10^{-1}$ to $10^9$ FFU, the inoculum dose of the diluted recombinant viral solution for a mouse is usually about 5 to 500 µL, preferably about 20 to 200 µL per dose.

5. Foreign Gene Transfer Agent

A foreign gene transfer agent containing (1) the above viral vector, (2) the above recombinant virus, or a recombinant virus prepared by the above process is also one aspect of the present invention. A preferred embodiment of the foreign gene transfer agent is a foreign gene transfer agent containing the above recombinant virus or a recombinant virus prepared by the above process. Such a foreign gene transfer agent can be preferably used to infect an in vitro cell or a living cell (an animal) with the recombinant virus in the above process for introducing a foreign gene. This embodiment of the present invention can be preferably used to introduce a foreign gene into a nerve system cell or the like of an animal. In particular, this embodiment of the present invention is preferably used to introduce a foreign gene into a cranial nerve system cell.

A preferred embodiment of the foreign gene transfer agent of the present invention is a foreign gene transfer agent, for a cranial nerve system cell, containing the above recombinant virus or a recombinant virus prepared by the above process. As the cranial nerve system cell, preferred is a mammalian cranial nerve system cell, and examples of the mammalian cranial nerve system cell include a glia cell, a neuron of a cerebral cortex, a hippocampal neuron, a cerebellar neuron, and a mesencephalic neuron. The foreign gene transfer agent of the present invention may further contain other drugs such as a therapeutic agent for neurological diseases, and may contain a pharmaceutically acceptable component according to the dosage form. The dosage form of the foreign gene transfer agent of the present invention is preferably a dosage form for parenteral administration, for example, an injection, an infusion, an ointment, a gel, a cream, a patch, a nebula, a spray, or the like. Among these, preferred is an injection.

An injection for parenteral administration may be an aqueous injection or an oily injection. In cases where the injection is an aqueous injection, it can be prepared according to a known method by, for example, mixing the recombinant virus with a solution in which a pharmaceutically acceptable additive is added as appropriate to an aqueous solvent (water for injection, purified water, or the like), sterilizing the mixture by filtration with a filter or the like, and packing the resulting solution into a sterilized container. Examples of the pharmaceutically acceptable additive include isotonizing agents such as sodium chloride, potassium chloride, glycerin, mannitol, sorbitol, boric acid, borax, glucose, and propylene glycol; buffers such as a phosphate buffer solution, an acetate buffer solution, a borate buffer solution, a carbonate buffer solution, a citrate buffer solution, a Tris buffer, a glutamate buffer solution, and an epsilon aminocaproic acid buffer solution; preservatives such as methyl parahydroxybenzoate, ethyl parahydroxybenzoate, propyl parahydroxybenzoate, butyl parahydroxybenzoate, chlorobutanol, benzyl alcohol, benzalkonium chloride, sodium dehydroacetate, sodium edetate, boric acid, and borax; thickeners such as hydroxyethyl cellulose, hydroxypropyl cellulose, polyvinyl alcohol, and polyethylene glycol; stabilizers such as sodium hydrogen sulfite, sodium thiosulfate, sodium edetate, sodium citrate, ascorbic acid, and dibutylhydroxytoluene; and pH adjusters such as hydrochloric acid, sodium hydroxide, phosphoric acid, and acetic acid. To the injection, a suitable solubilizer may be further added, and examples of the solubilizer include alcohols such as ethanol; polyalcohols such as propylene glycol and polyethylene glycol; and nonionic surfactants such as polysorbate 80, polyoxyethylene hydrogenated castor oil 50, lysolecithin, and Pluronic polyol. The injection may also contain proteins such as bovine serum albumin and keyhole limpet hemocyanin; polysaccharides such as aminodextran; and the like. In cases where the injection is an oily injection, for example, sesame oil or soybean oil is used as an oily solvent, and benzyl benzoate or benzyl alcohol may be mixed as a solubilizer. A prepared injection solution is usually packed into a suitable ampule, vial, or the like. A liquid preparation such as an injection can be subjected to cryopreservation, lyophilization, or the like, which removes the water in the preparation, and then stored. Before use, the lyophilized preparation is redissolved with an added water for injection or the like.

The amount of the recombinant virus contained in the foreign gene transfer agent of the present invention varies depending on the dosage form or the administration route of the foreign gene transfer agent, but the amount is usually selected and determined as appropriate from the range of about 0.0001 to 100% in a final preparation. The administration method and administration amount of the foreign gene transfer agent are the same as those of the recombinant virus in the above process for introducing a foreign gene. The foreign gene transfer agent of the present invention is useful as, for example, a composition for gene delivery that is used as a therapeutic agent for cranial nerve diseases of an animal, a therapeutic agent for chronic liver diseases such as hepatitis C, an antitumor drug, a vaccine, or the like. The administration target of the foreign gene transfer agent of the present invention is preferably the mammals described above.

6. Use of Viral Vector

The viral vector, the recombinant virus, the process for introducing a foreign gene, and the foreign gene transfer agent of the present invention can be applied, as a gene transfer technique not affecting a host chromosome, to various fields.

For example, the viral vector and the recombinant virus of the present invention can be used as a gene delivery vector for treating cranial nerve diseases of animals including humans. The viral vector and the recombinant virus can also be preferably used for vaccines against chronic liver diseases, tumors, infections, or the like.

Examples of the cranial nerve disease include Alzheimer's disease, Parkinson's disease, multiple sclerosis, schizophrenia, autism, and other functional psychiatric disorders. The recombinant virus of the present invention is useful for treating or preventing such a disease. For example, in cases where a gene of an enzyme that degrades a protein causing a cranial nerve disease, or a nucleic acid sequence having a function of inhibiting the expression of the causal protein, or the like is used as the foreign gene in the viral vector of the present invention, infection of a cranial nerve system cell with the recombinant virus produced from the viral vector allows degradation of the causal protein or inhibition of the expression of the protein, thereby preventing or treating the above diseases. In terms of the prevention or the treatment of a disease caused by reduced secretion of a brain substance (for example, serotonin, dopamine, somatostatin, neprilysin, or the like), infection of a cranial nerve system cell with the recombinant virus produced from the viral vector into which a gene encoding such a brain substance is inserted can enhance the production of the brain substance, thereby preventing or treating the brain disease.

The word "treat" means, besides to completely cure a clinical condition, to inhibit the progress and/or deterioration of the symptom and then to stop the progress of the clinical condition even when the disease is not cured completely, or to improve all or part of the clinical conditions and then to lead to recovery. The word "prevent" means to prevent, inhibit, or delay the onset of the clinical condition.

The viral vector and the recombinant virus of the present invention can also be used to treat or prevent viral encephalitis such as Japanese encephalitis. The viral vector and the recombinant virus of the present invention can also be preferably used for a cranial nerve disease of an experimental animal, a companion animal, or a producing animal. Examples of the disease include BSE (bovine spongiform encephalopathy) and rabies. Examples of the experimental animal include a mouse, a rat, a guinea pig, a rabbit, a cat, and a dog, and examples of the companion animal include a mouse, a rat, a guinea pig, a rabbit, a cat, and a dog. Examples of the producing animal include cattle, a horse, a pig, and a sheep.

The viral vector and the recombinant virus of the present invention can be applied to a visualization technique of a nerve system cell in the field of neuroscience. The viral vector of the present invention is also useful as an RNA viral vector expressing a functional RNA molecule, and can also be applied to a technique for a vector stably expressing a functional RNA such as an siRNA, a miRNA, and an RNA aptamer. For example, in cases where a sequence encoding a functional RNA such as an siRNA, a miRNA, and an RNA aptamer is used as the foreign gene in the viral vector of the present invention, such a functional RNA molecule can be expressed in a desired cell. With the use of the viral vector and the recombinant virus of the present invention, a single-strand antibody (scFv) can also be expressed in the brain.

Use of a coat protein derived from another virus can convert the viral vector or the recombinant virus of the present invention into a viral vector or a recombinant virus that specifically infects a tumor cell, and such a viral vector or a recombinant virus can be used, as an antitumor viral vector, to introduce a drug gene or an siRNA inhibiting overexpressed gene into a tumor cell. Further, in cases where a gene having a neutralization activity against HIV, influenza virus, or the like (for example, env, gag, or the like of HIV; the HA gene, the NA gene, or the like of influenza virus; or the like) is introduced as the foreign gene, the viral vector or the recombinant virus of the present invention can be used for recombinant vaccines. In addition, with regard to infections associated with a chronic course, for example, HCV or the like, use of the viral vector or the recombinant virus into which a siRNA of a target virus genome is introduced is beneficial for the development of a new infection therapy using a functional RNA.

A kit for introducing a foreign gene, the kit comprising the above viral vector, is also one aspect of the present invention.

The kit of the present invention may comprise as appropriate, besides the viral vector, a helper plasmid, a cell into which a foreign gene is to be introduced, a buffer solution, a culture medium, and the like. A preferred embodiment of the viral vector is as described above. The cell into which a foreign gene is to be introduced is preferably a nerve system cell, such as a cranial nerve system cell, or the like. The kit of the present invention can be preferably used for the introduction of a foreign gene into a cranial nerve system cell or the like, which introduction has been technically difficult.

EXAMPLES

The present invention will be described in detail below with reference to Examples. However, Examples are provided only for illustrating the present invention and the present invention is not limited thereto.

Example 1

1. Preparation of Plasmid pCAG-Fct

Based on the plasmid pCAG-HR-SV3 described in Yanai et al., Microbes and Infection 8 (2006), 1522-1529, a plasmid was prepared by replacing the region of the chloramphenicol acetyltransferase (CAT) gene inserted into the above plasmid with the genome sequence of the Borna disease virus strain He/80 (SEQ ID NO: 1) as follows.

A cytomegalovirus (CMV)-derived BDV mini genome vector (pCMV-HR) was obtained as follows. A chemically synthesized oligonucleotide encoding a hammer head ribozyme (HamRz) (Briese et al., Proc. Natl. Acad. Sci. U.S.A. 89 (1992) 11486-11489; and Le Mercier et al., J. Virol., 76 (2002) 2024-2027) and a chemically synthesized oligonucleotide encoding the 5' untranslated region (UTR) sequence of BDV (Cubitt, B., Oldstone, C. and de la Torre, J. C., Sequence and genome organization of Borna disease virus. J. Virol. 68 (3), 1382-1396 (1994)) were annealed and ligated between the KpnI and XhoI sites of a vector pcDNA3 (Invitrogen, San Diego, Calif.). The obtained plasmid was cut at the Eco47III and XbaI sites. Into the obtained plasmid, a BDV 3' UTR fused with a hepatitis δ virus ribozyme (HdRz)) and a cDNA clone encoding the BDV strain He/80 genome were inserted to give a plasmid pc-HR. The BDV 3' UTR fused with HdRz had been amplified from a plasmid phuPol I-MG (Perez et al., J. Gen. Virol. 84 (2003) 3099-3104). Finally, the BglII and XbaI fragment of the pc-HR was inserted between the BamHI and XbaI sites of pBluescript SKIT (-) (Stratagene, La Jolla, Calif.) to give the pCMV-HR. A BDV mini genome vector pCAG-HR containing CAG (a complex of a chicken β-actin promoter and a CMV enhancer) was obtained as follows. First, a CAG promoter was subcloned into pBluescript SKII (-) (Stratagene, La Jolla, Calif.) (pBS-CAG). The CAG promoter is a hybrid promoter composed of a cytomegalovirus IE enhancer fused with a chicken δ-actin promoter, and described in Sawichi et al., Exp. Cell Res. 244 (1998) 367-369. Next, the region from HamRz to HdRz in the pCMV-HR was amplified by PCR, and the PCR product was inserted into the blunt ends of the SalI and EcoRI sites in the pBS-CAG.

Next, the fragment consisting of 113 bases at the 5' end in an SV40 origin/promoter (SV3 region) was amplified from a pEGFP-N1 (Clontech) by PCR (Clontech Laboratory, Inc., Palo Alto, Calif.), and the PCR product was inserted into the NotI site of the pCAG-HR to give a plasmid pCAG-Fct.

2. Preparation of BDV Genome Plasmid in which GFP is Inserted into Untranslated Region Between P Gene and M Gene (PCAG-Fct-P/M-GFP)

A plasmid pCAG-Fct-P/M was prepared by inserting a foreign gene insertion cassette into the untranslated region between the P gene and the M gene as follows.

A) With the use of the pCAG-Fct (a plasmid in which the cDNA of the Borna virus strain He/80 (SEQ ID NO: 1) was cloned) prepared in Example 1 as a template, the region from the EcoT22I site to the Bst1107I site was amplified by PCRs using primers 1 and 4, as well as using primers 2 and 3. Next, 0.5 µL each of the PCR products were mixed and amplified again using the primers 1 and 2 to give a foreign gene insertion cassette having a BstBI site and a PacI site between the P gene and the M gene.

B) The PCR product of A) was recombined into the pCAG-Fct using EcoT22I and Bst1107I, and thus the pCAG-Fct-P/M was obtained.

C) A GFP was inserted using BstBI and PacI and thus the plasmid pCAG-Fct-P/M-GFP was obtained.

```
<Primer>
Primer 1:
                                    (SEQ ID NO: 5)
5-GGAATGCATTGACCCAACCGGTAGACCAGC-3

Primer 2:
                                    (SEQ ID NO: 6)
5-AACATGTATTTCCTAATCGGGTCCTTGTATACGG-3

Primer 3:
                                    (SEQ ID NO: 7)
5-ttcgaaGGTTGGttaattaaccataaaaaaatcgaatcacc-3

Primer 4:
                                    (SEQ ID NO: 8)
5-ttaattaaCCAACCttcgaaGGTGATTCGATTTTTTTATGG-3
```

3. Preparation of Helper Plasmids

Helper plasmids, i.e., a plasmid expressing the N gene of BDV (pcN), a plasmid expressing the P gene of BDV (pCXN2-P), and a plasmid expressing the L gene of BDV (pcL) were prepared by the following procedures.

The pcN was prepared by amplifying the N gene region from a pHA-p40N plasmid (Kobayashi T, Watanabe M, Kamitani W, Zhang G, Tomonaga K and Ikuta K. Borna disease virus nucleoprotein requires both nuclear localization and export activities for viral nucleocytoplasmic shuttling. J. Virol. 75: 3404-3412. (2001)) by PCR, and inserting the PCR product into the pBS-CAG (mentioned above).

The plasmid pCXN2-P was prepared by inserting the fragment of a pcD-P obtained by gel extraction (Zhang G, Kobayashi T, Kamitani W, Komoto S, Yamashita M, Baba S, Yanai H, Ikuta K and Tomonaga K. Borna disease virus phosphoprotein represses p53-mediated transcriptional activity by interference with HMGB1. J. Virol. 77: 12243-12251. (2003)) between the EcoRI and XhoI sites of a pCXN2 (Niwa H, Yamamura K, Miyazaki J 1991 Efficient selection for high-expression transfectants with a novel eukaryotic vector. Gene 108: 193-199).

The pcL was prepared by the method described in Perez et al., J. Gen. Virol. 84 (2003) 3099-3104. The nucleotide sequences of the recombinant plasmids were determined by DNA sequence.

Reference Example 1

Figure 4:
Figure 5:
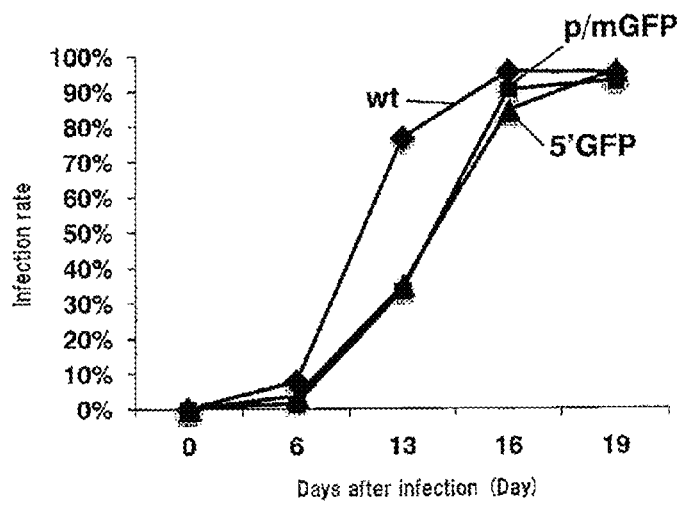
Figure 6:
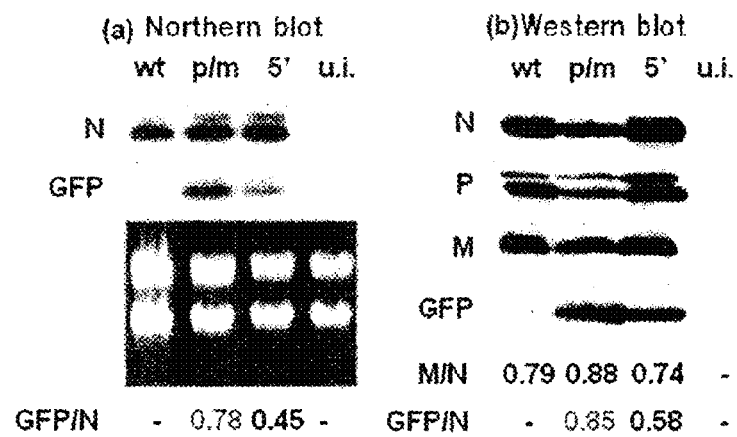
Figure 7:
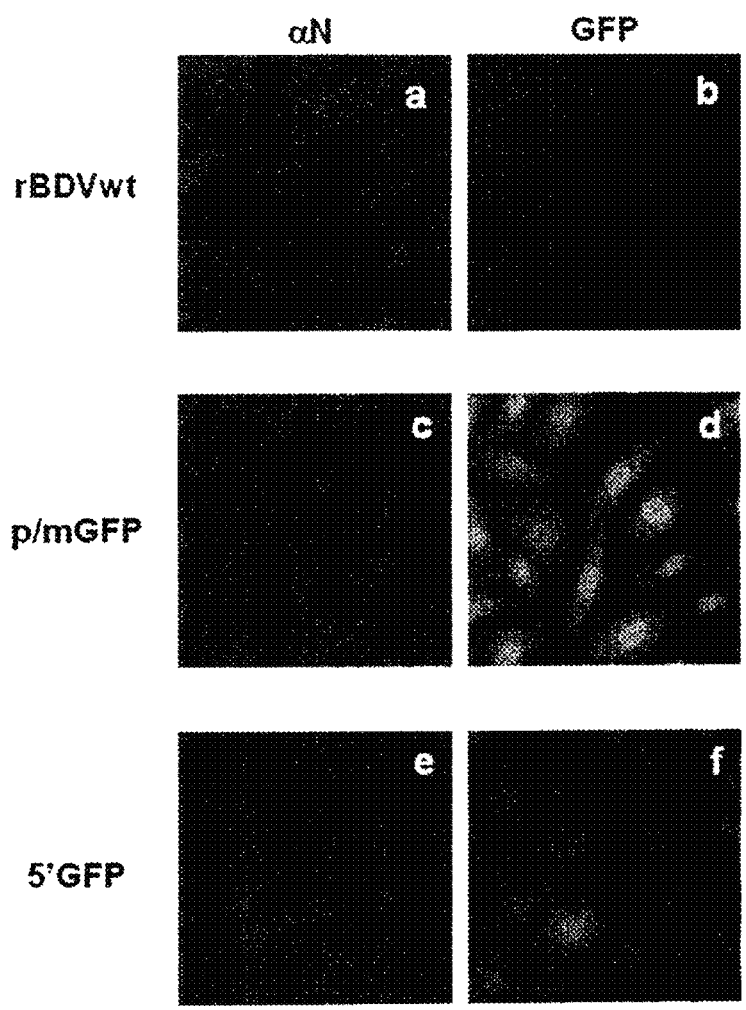

A recombinant viral vector in which the GFP gene was inserted into the untranslated region at the 5' end of the BDV genome was prepared according to the method described in U. Schneider et al., Journal of Virology (2007) 7293-7296. The construct of this recombinant viral vector (rBDV-5' GFP) is schematically shown in FIG. 4.

Example 2

Preparation and Characteristics Comparison of BDV Vectors Using Plasmid with Insertion Between P/M Genes The pCAG-Fct-P/M-GFP and the helper plasmids (the N gene expression plasmid, the P gene expression plasmid, and the L gene expression plasmid; which are the pcN, the pCXN2-P, and the pcL, respectively) were introduced into 293T cells using FuGENE (registered trademark) 6 transfection reagent (Roche Molecular Diagnostics, Pleasanton, Calif.) or Lipofectamine (registered trademark) 2000 (Invitrogen). The following amounts of the viral vectors and the like were used: 1 to 4 µg of the pCAG-Fct-P/M-GFP was used relative to $10^4$ to $10^6$ cells (293T cells), and the helper plasmids in a ratio of 0.125 to 0.5 µg of the pcN, 0.0125 to 0.05 µg of the pCXN2-P, and 0.125 to 0.5 µg of the pcL were added thereto.

After introduction of the viral vector and the helper plasmids, the 293T cells were cultured in a Dulbecco Modified Eagle Medium at 37° C. for 48 hours. The supernatant was then recovered and centrifuged at 800 g for 10 minutes, and purified by filtration with a filter having a pore size of 0.22 to 0.45 µm to give a recombinant GFP expression virus (hereinafter sometimes referred to as the recombinant virus p/mGFP).

As a comparison, a recombinant virus (hereinafter sometimes referred to as the recombinant virus 5' GFP) was prepared by introducing the vector rBDV-5' GFP prepared in Reference Example 1 into 293T cells, and purifying the obtained recombinant virus, in the same manner as described above. As a control, a wild-type BDV (hereinafter sometimes referred to as wt) was introduced into 293T cells.

48 hours after infection of the cultured cells, the spread of infection among the cells and the release of the viruses to the supernatant from the infected cells were investigated by indirect immunofluorescence and Western blot. It was observed that the production of each of the recombinant virus p/mGFP, the recombinant virus 5' GFP, and wt started 24 hours after the infection.

The wild-type BDV (wt), and the purified recombinant viruses p/mGFP and 5' GFP were separately used to infect Vero cells at an M.O.I. of 0.01, and the spread of infection among the cells from the zero day to the 19th day after the infection was investigated by Northern blot, Western blot, or indirect immunofluorescence. The results are shown in FIGS. 5 to 8.

The indirect immunofluorescence was carried out by the following process.

An anti-BDV N antibody and an anti-BDV M antibody were prepared according to the methods described in Watanabe M, Zhong Q, Kobayashi T, Kamitani W, Tomonaga K, Ikuta K. Molecular ratio between Borna disease viral-p40 and -p24 proteins in infected cells determined by quantitative antigen capture ELISA. Microbiol Immunol. 2000. 44: 765-72; and Chase G, Mayer D, Hildebrand A, Frank R, Hayashi Y, Tomonaga K, Schwemmle M. Borna disease virus matrix protein is an integral component of the viral ribonucleoprotein complex that does not interfere with polymerase activity. J. Virol. 2007. 81: 743-749.

After the Vero cells infected with the wild-type BDV or each recombinant virus were cultured for a certain period of days, the cells were recovered and fixed on glass plates. The fixed cells were reacted with the anti-BDV N antibody (diluted with a phosphate buffer solution to a concentration of 0.2 to 5 µg/mL), or with the anti-BDV M antibody (diluted with a phosphate buffer solution to a concentration of 0.2 to 5 µg/mL) at 37° C. for about 1 hour. After washing, the cells were reacted with a secondary antibody, a fluorescent-labeled anti-IgG antibody (Molecular Probes) (diluted with a phosphate buffer solution to a concentration of 0.01 to 0.1 μg/mL), in the same manner as described above, and the fluorescence (anti-N antibody or anti-M antibody: red, and GFP green) of the cells was observed under a fluorescent microscope.

The Northern blot and the Western blot were carried out according to the methods described in Watanabe Y, Ibrahim M S, Hagiwara K, Okamoto M, Kamitani W, Yanai H, Ohtaki N, Hayashi Y, Taniyama. H, Ikuta K, Tomonaga K. Characterization of a Borna disease virus field isolate which shows efficient viral propagation and transmissibility. Microbes Infect. 2007. 9: 417-427.

FIG. 5 is a graph showing the time course of the infection rates of the wild-type BDV or the recombinant BDVs in Vero cells from the zero day to the 19th day after the infection. The infection rates shown in FIG. 5 were determined as follows: the infection rate of the wild-type BDV was determined by indirect immunofluorescence using, as an indicator, the fluorescence of the fluorescent-labeled antibody against the anti-BDV N antibody, and the infection rates of the recombinant BDVs were determined by indirect immunofluorescence using, as an indicator, the fluorescence of the GFP and the fluorescence of the fluorescent-labeled antibody against the anti-BDV N antibody. In FIG. 5, wt (lozenge symbol) represents the wild-type BDV, p/mGFP (square symbol) represents the recombinant virus p/mGFP, and 5' GFP (triangle symbol) represents the recombinant virus 5' GFP prepared in Reference Example 1. FIG. 5 shows that about 100% of the Vero cells were infected by both of the recombinant viruses, p/mGFP and 5' GFP, about 15 days after the infection in the same manner as the infection of the Vero cells with the wild-type BDV. This result revealed that both recombinant viruses, p/mGFP and 5' GFP, have a similar virus production capacity to that of the wild-type BDV.

FIG. 6 shows the results of Northern blot. In FIG. 6, wt represents the wild-type BDV, p/m represents the recombinant virus p/mGFP, and 5' represents the recombinant virus 5' GFP. u. i. represents uninfected cells.

FIG. 6 (*a*) is the results of Northern blot for the expressions of the N gene of BDV (top) and the GFP gene (middle) in the Vero cells 19 days after the infection. As is apparent from FIG. 6(*a*), the gene of the virus protein (N protein) is almost equally expressed in the cells infected with any of the BDVs. The expression ratio of the foreign gene (the GFP gene) to the virus that infected in the cells infected with the recombinant virus p/mGFP (GFP gene/N gene) was 0.78, and the expression ratio in the cells infected with the recombinant virus 5' GFP (GFP gene/N gene) was 0.45. That is, the expression ratio of the GFP gene to the virus that infected the cells for the recombinant virus p/mGFP was about twice as large as that for the recombinant virus 5' GFP. In the bottom figure of FIG. 6 (*a*), the ribosomal RNA contained in the electrophoretic samples was visualized for quantification of the RNAs that were used for the above analyses.

FIG. 6 (*b*) is the results of Western blot for the expressions of the N protein (top), the P protein (the second from the top), and the M protein (the third from the top) of BDV, and the GFP (bottom) in the Vero cells 19 days after the infection. FIG. 6(*b*) shows that the virus proteins (the N protein, the P protein, and the M protein) were almost equally expressed in the cells infected with any of the BDVs. The expression ratio of the foreign gene (the GFP gene) to the virus that infected the cells for the recombinant virus p/mGFP (GFP gene/N protein) was 0.85, and the expression ratio for the recombinant virus 5' GFP (GFP gene/N protein) was 0.58. That is, the expression ratio of the GFP gene to the virus that infected the cells for the recombinant virus p/mGFP was larger than that for the recombinant virus 5' GFP.

FIGS. 7*a* to 7*f* are photomicrographs of the cells infected with the wild-type BDV, the recombinant virus p/mGFP, or the recombinant virus 5' GFP. FIGS. 7*a* and 7*b* show the cells infected with the wild-type BDV, FIGS. 7*c* and 7*d* show the cells infected with the recombinant virus p/mGFP, and FIGS. 7*e* and 7*f* show the cells infected with the recombinant virus 5' GFP. FIGS. 7*a*, 7*c*, and 7*e* are the results of investigation into the infection of the cells with the viruses, by means of indirect immunofluorescence using the anti-N protein antibody (anti-BDV N antibody) and the fluorescent-labeled antibody (Molecular Probes). In FIGS. 7*a*, 7*c*, and 7*e*, the light-emitting substances (red) are the N protein. FIGS. 7*b*, 7*d*, and 7*f* are the results of investigation into the foreign gene (GFP) expression by the viruses, by means of the fluorescence (green fluorescence) of the protein of the foreign gene. In FIGS. 7*b*, 7*d*, and 7*f*, the GFP is detected by green fluorescence.

In FIGS. 7*a* to 7*f*, the N protein is almost equally expressed in the cells infected with any of the BDV viruses, which reveals that the replication abilities of these BDV viruses are almost the same. However, the fluorescence intensity of the GFP in the cells infected with the recombinant virus p/mGFP is significantly larger than that in the cells infected with the recombinant virus 5' GFP, which reveals that the expression efficiency of the foreign gene (GFP) in the recombinant virus p/mGFP is significantly higher than that in the recombinant virus 5' GFP.

FIGS. 8*a* to 8*f* are photomicrographs of the cells infected with the wild-type BDV, the recombinant virus p/mGFP, or the recombinant virus 5' GFP. FIGS. 8*a* and 8*b* show the cells infected with the wild-type BDV, FIGS. 8*c* and 8*d* show the cells infected with the recombinant virus p/mGFP, and FIGS. 8*e* and 8*f* show the cells infected with the recombinant virus 5' GFP. FIGS. 8*a*, 8*c*, and 8*e* are the results of investigation into the infection of the cells with the viruses, by means of indirect immunofluorescence using the anti-M protein antibody (anti-BDV M antibody) and the fluorescent-labeled antibody (Molecular Probes). FIGS. 8*b*, 8*d*, and 8*f* are the results of investigation into the foreign gene (GFP) expression by the viruses, by means of the fluorescence (green fluorescence) of the protein of the foreign gene. In FIGS. 8*a*, 8*c*, and 8*e*, the light-emitting substances (red) are the M protein. In FIGS. 8*b*, 8*d*, and 8*f*, the GFP is detected by green fluorescence.

In FIGS. 8*a* to 8*f*, the M protein is almost equally expressed in the cells infected with any of the BDV viruses, which reveals that the replication abilities of these BDV viruses are almost the same. However, the fluorescence intensity of the GFP in the cells infected with the recombinant virus p/mGFP is significantly larger than that in the cells infected with the recombinant virus 5' GFP, which reveals that the expression efficiency of the foreign gene in the recombinant virus p/mGFP is significantly higher than that in the recombinant virus 5' GFP.

Example 3

The recombinant virus p/mGFP prepared in Example 2 and the recombinant virus 5' GFP prepared in Reference Example 1 were separately used to infect the brain of a rat as follows.

The purified recombinant viruses were separately diluted with a PBS or a culture medium to a virus titer of $10^3$ FFU, and then 10 to 20 of each of the diluted recombinant virus solutions was separately inoculated into the cranium of a neonatal rat from the left side of the head within 24 hours after birth (FIG. 9). The brains were harvested 7, 14, and 21 days after inoculation, and divided into each region as shown in FIG. 10. DNAs were extracted from each region (with the use of a DNA extraction kit (QIAGEN)), and recombinant virus infection was separately investigated by means of PCR and the expression of the GFP. For PCR, primers specific to BDV were used. The sequences of these primers are shown below. The sequence of a forward primer specific to BDV:

(SEQ ID NO: 9)
5-GGAATGCATTGACCCAACCGGTAGACCAGC-3

The sequence of a reverse primer specific to BDV:

(SEQ ID NO: 10)
5-AACATGTATTTCCTAATCGGGTCCTTGTATACGG-3

The PCR products were subjected to 1% agarose electrophoresis. The result shows that in the rat 7 days after the virus was inoculated into the left-middle part of the brain, the recombinant virus was found in, besides the inoculation site, the cerebral cortex (the anterior part of the right brain in FIG. 10) and the cerebellum (the posterior part of the right brain in FIG. 10). FIG. 11 shows the results of electrophoresis of the PCR products. The lane indicated by p/mGFP is the PCR product of the rat brain infected with the recombinant virus p/mGFP. The lane indicated by 5' GFP is the PCR product of the rat brain infected with the recombinant virus 5' GFP. In each lane of p/mGFP and 5' GFP, a and b are the PCR products of the DNAs from the cerebral cortex and the cerebellum, respectively. The bands detected in FIG. 11 are the bands of the BDV genome fragments amplified by the above PCR. In the above PCR, the region between the P gene and the M gene of BDV was amplified. Since the recombinant virus p/mGFP contains the GFP gene between the P gene and the M gene, the band of its PCR product was detected closer to the high molecular weight side compared with that of the PCR product of the recombinant virus 5' GFP. In FIG. 11, I indicates the Vero cells infected with the wild-type BDV, and U indicates uninfected cells. These results revealed that the inoculated recombinant viruses were transmitted to other parts of the brain.

Figure 12:
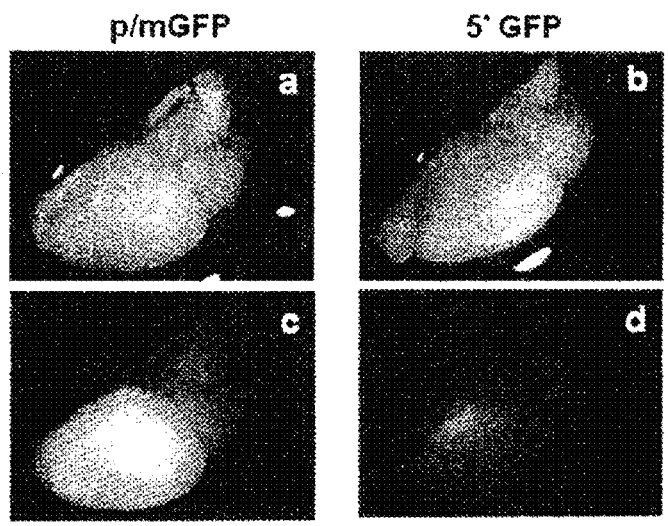

FIG. 12 is the macro photographs (a and b) of the reversed side of the rat brain incised 14 days after the inoculation, and the fluorescent macro photographs (c and d) of said brain. In FIGS. 12c and 12d, the fluorescent part has the expressed GFP. As is apparent from FIGS. 12c and 12d, the fluorescence intensity of the GFP in the cerebral cortex of the brain infected with the recombinant virus p/mGFP was significantly larger than that in the cerebral cortex of the brain infected with the recombinant virus 5' GFP, which reveals that the expression efficiency of the foreign gene (GFP) in the recombinant virus p/mGFP is significantly higher than that in the recombinant virus 5' GFP.

Figure 13:
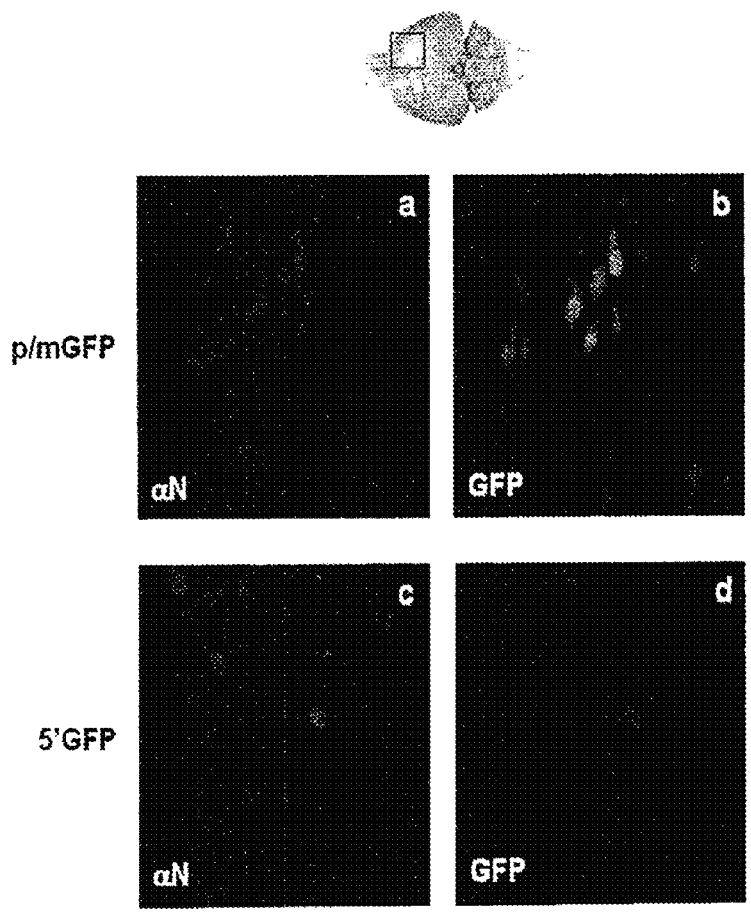

FIGS. 13a to 13d are photomicrographs of the sections of the cerebral cortex (the area indicated by the square in the photograph shown above FIGS. 13a to 13d). FIGS. 13a and 13c are the results of investigation into the expression of the N gene in the cerebral cortex of the rat 7 days after the inoculation, by means of indirect immunofluorescence using the same anti-N protein antibody (anti-BDV N antibody) and fluorescent-labeled antibody (Molecular Probes) as those used in Example 2. The N protein was detected by red fluorescence. The results revealed that the N protein was almost equally expressed in the cells infected with any of the recombinant virus p/mGFP and the recombinant virus 5' GFP (the amounts of these viruses that infected the cells were almost the same). FIGS. 13b and 13d show the results of fluorescent detection of the expression of the GFP in the same sections as those shown in FIGS. 13a and 13c. The fluorescence intensity of the GFP in the cerebral cortex of the brain infected with the recombinant virus p/mGFP (FIG. 13b) was significantly larger than that in the cerebral cortex of the brain infected with the recombinant virus 5' GFP (FIG. 13d).

Example 4

A recombinant vector in which the DsRed gene was inserted into the untranslated region between the P gene and the M gene (rBDV-p/mDsRed vector) was prepared in the same manner as in Example 1 except that the DsRed gene (Clontech) was used instead of the GFP gene, and a recombinant virus was prepared using the vector in the same manner as in Example 2. As a comparison, a recombinant vector in which the DsRed gene was inserted into the 5' end of the BDV genome (rBDV-5' DsRed vector) was prepared in the same manner as in Reference Example 1 except that the DsRed gene (Clontech) was used instead of the GFP gene, and a recombinant virus was prepared using the vector in the same manner as in Example 2. Ten days after each recombinant virus was separately used to infect cultured cells, the infection of the cells with the recombinant viruses and the expression of the DsRed gene were investigated by indirect immunofluorescence using the same anti-N protein antibody (anti-BDV N antibody) and fluorescent-labeled antibody (Molecular Probes) as those used in Example 2. In the cells infected with the recombinant virus produced from the rBDV-p/mDsRed vector, the expressions of the N protein (FIG. 14 (*a*)) and DsRed (FIG. 14 (*b*)) were observed as shown in FIG. 14 (the N protein was detected as green fluorescence of the secondary antibody and DsRed was detected as red fluorescence). On the other hand, the cells infected with the rBDV-5'DsRed vector were not able to produce a recombinant virus.

Example 5

A recombinant vector in which the luciferase gene was inserted into the untranslated region between the P gene and the M gene (rBDV-p/mLuci vector) was prepared in the same manner as in Example 1 except that the firefly-derived luciferase gene (1.6 kb) was used instead of the GFP gene, and a recombinant virus was prepared using the vector in the same manner as in Example 2. As a comparison, a recombinant vector in which the luciferase gene was inserted into the 5' end of the BDV genome (rBDV-5'Luci vector) was prepared in the same manner as in Reference Example 1 except that the luciferase gene was used instead of the GFP gene. Ten days after each recombinant virus was separately used to infect cultured cells, the infection of the cells with the recombinant viruses and the expression of the luciferase gene were investigated by indirect immunofluorescence using the same anti-N protein antibody (anti-BDV N antibody) as that used in Example 2. In the cells infected with the recombinant virus produced from the rBDV-p/mLuci vector, the N protein was observed as shown in FIG. 15*a*. On the other hand, the cells infected with the rBDV-5' Luci vector were not able to produce a recombinant virus. The luciferase activity in the Vero cells infected with the recombinant virus rBDV-p/mLuci (rBDV-p/mLuci in FIG. 15*b*) was measured using a luciferase assay kit (Promega) according to the attached instruction manual. The luciferase activity was significantly higher than that in uninfected cells (FIG. 15*b*). The above results confirmed that the luciferase produced from the recombinant virus rBDV-p/mLuci functions properly.

Example 6

In the same manner as in Example 3, the recombinant virus p/mGFP produced from the plasmid in which the GFP was inserted between the P gene and the M gene (plasmid pCAG-Fct-P/M-GFP; hereinafter referred to as "p/mGFP") prepared in Example 1 was intracranially inoculated into a neonatal mouse. Samples were harvested form the cerebral cortex and cerebellum of the mouse (n=2, respectively) 2 months and 8 months after the inoculation of the recombinant virus, and the infection of cells with the virus was investigated by (1) indirect immunofluorescence using an anti-N protein antibody (anti-BDV N antibody) and a fluorescent-labeled antibody (Molecular Probes) and by (2) the fluorescence of the GFP in the same manner as in Example 3. The results revealed that the BDV virus is persistently expressed in the infected cells (of the cerebral cortex and the cerebellum of the mouse) for 2 to 8 months after the inoculation.

FIGS. 18*a* and 18*b* are fluorescent photomicrographs of the cross section of a mouse brain 8 months after the inoculation of the recombinant virus. FIG. 18*a* is a macro photograph and FIG. 18*b* is the microscopically enlarged photograph of the area enclosed by the square in FIG. 18*a*. In FIGS. 18*a* and 18*b*, the GFP is detected by green fluorescence. In FIGS. 18*a* and 18*b*, the part emitting the green fluorescence of the GFP is shown by the gray part.

Example 7

Recovery of G-Deleted Virus (1) Construction of Plasmid

A) Preparation of p/mGFP deltaG L linear (p/mGFP ΔG LL)

Based on the p/mGFP prepared in Example 1, the G gene encoding the viral membrane glycoprotein was deleted by point mutation using PCR. In particular, two sequences encoding methionine present in the G gene (Genome (i.e., the bases of SEQ ID NO: 1) No. 2236 to 2238 and 2248 to 2250) were replaced with sequences encoding threonine (ATG->ACG). FIG. 19 shows a schematic view of the preparation procedure of a plasmid p/mGFP ΔG encoding a G gene deleted virus. First, with the use of the p/mGFP as a template, PCRs (25 cycles of 98° C. for 10 seconds, 55° C. for 5 seconds, and 72° C. for 0.5 or 1 minute) were performed using primers A1 and B1, as well as using primers C1 and D1, whose sequences are shown in Table 1 (FIG. 19 (*a*)).

Next, with the use of the amplification products (the 1st PCR products) as a template, PCR (25 cycles of 98° C. for 10 seconds, 55° C. for 5 seconds, and 72° C. for 1.5 minutes) was performed again using the above primers A1 and D1 (FIG. 19 (*b*)). The obtained amplification product (the 2nd PCR product), in which methionine in the G gene was mutated into threonine, was recombined into the vector p/mGFP using restriction enzymes Bst1107I and NheI to give a p/mGFP ΔG (FIG. 19 (*c*)).

Next, the intron region of the L gene (originally part of the G gene region), which became unnecessary, was deleted and the divided parts of the L gene were connected (L linearize). In particular, the region from the cleavage site Bst1107I (the 2166th to the 2171st base sequence of SEQ ID NO: 1) to the first half of the exon of the L gene and the region of the latter half of the exon of the L gene (until the NheI site (the 6158th to 6163rd base sequence of SEQ ID NO: 1)) were separately amplified, connected to each other, and recombined into the p/mGFP ΔG. The outline of this procedure is shown in FIG. 20. First, with the use of the P/mGFP ΔG as a template, PCRs (25 cycles of 98° C. for 10 seconds, 55° C. for 5 seconds, and 72° C. for 0.5 minutes) were performed using primers A1 and E1, as well as using primers F1 and D1, whose sequences are shown in Table 1 (FIG. 20 (*a*)). Next, with the use of the amplification products (the 1st PCR products) as a template, PCR (25 cycles of 98° C. for 10 seconds, 55° C. for 5 seconds, and 72° C. for 1 minute) was performed using the above primers A1 and D1 (FIG. 20 (*b*)). The obtained amplification product (the 2nd PCR product), in which the intron region of the L gene was deleted, was recombined into the vector P/mGFP ΔG using restriction enzymes Bst1107I and NheI to give a p/mGFP ΔG LL (FIG. 20 (*c*)).

B) BDV G Gene Expression Plasmid

For the purpose of recovering a G-deleted virus, a plasmid expressing the G protein of BDV in a mammalian cell was prepared as a helper plasmid. The outline of this procedure is shown in FIG. 21. In particular, the G gene region was amplified by PCR using the p/mGFP as a template and inserted downstream of a chicken β-actin promoter (in the same manner as in the above preparation process for N, P, and L gene helper plasmids). First, with the use of the p/mGFP as a template, PCRs (25 cycles of 98° C. for 10 seconds, 55° C. for 5 seconds, and 72° C. for 0.5 or 1.0 minute) were performed using primers G1 and H1, as well as using primers I1 and J1, whose sequences are shown in Table 1 (FIG. 21 (*a*)). Next, with the use of the amplification products (the 1st PCR products) as a template, PCR (25 cycles of 98° C. for 10 seconds, 55° C. for 5 seconds, and 72° C. for 1.5 minutes) was performed using the above primers G1 and J1 (FIG. 21 (*b*)). The obtained amplification product (the 2nd PCR product) encodes the G gene, but mutation was introduced during the PCR into the splicing site (SD=2409 to 2415, and SA=2437 to 2442) that BDV originally possess, so that the G gene does not function (no amino acid mutation). In particular, the 2409th to the 2415th of the wild-type (WT) BDV genome, GGTTATG, was mutated into agtctcc (ΔSA), and the 2437th to the 2442nd of the wild-type (WT) BDV genome, GGTTATG, was mutated into agtctcc (ΔSD). This 2nd PCR product (ΔSDSA G gene) was inserted into an expression plasmid (the pCXN2 used for the preparation of the helper plasmid in Example 1) using restriction enzymes KpnI and SmaI (FIG. 21 (*c*)) to give a BDV G gene expression plasmid. The nucleotide sequence of the recombinant plasmid was determined by DNA sequencing. In this experiment, the pCXN2 was used for the preparation of the G gene expression plasmid, but other plasmids that can express a gene in a mammalian cell can be used.

The sequences of the primers used above are shown in Table 1.

TABLE 1

| Primer No. | Sequence |
|---|---|
| A1 | CCGTATACAAGGACCCGATTAGGAAATACATGTT (SEQ ID NO: 12) |
| B1 | AAGAGAAGACGTTGAAAGCTGCGTTAATTGCG (SEQ ID NO: 13) |
| C1 | CGCAATTAACGCAGCTTTCAACGTCTTCTCTT (SEQ ID NO: 14) |
| D1 | GGGTCTGCAAGAGTGCTAGCTGAAAGGGC (SEQ ID NO: 15) |
| E1 | GCGAAGGAGGCTCGCATGAAATGACATTTTCCG (SEQ ID NO: 16) |
| F1 | TCATTTCATGCGAGCCTCCTTCGCGAGGAGGAGAC (SEQ ID NO: 17) |
| G1 | TCGGTACCATGCAGCTTTCAATGTCTTCTCTTATC (SEQ ID NO: 18) |
| H1 | ATAGGAGACTTCGCATGAAATG (SEQ ID NO: 19) |
| I1 | TTCATGCGAAGTCTCCTATCTTAACC (SEQ ID NO: 20) |
| J1 | TCCCCCGGGTTATTCCTGCCACCGGCCGAGGCGTC TCCTCCTCGCGAAGCTTGCGGGTAAGG (SEQ ID NO: 21) |

(2) Preparation of BDV G Gene Expressing Cell

A BDV G gene stably expressing cell was prepared using the G protein expression plasmid prepared in the above (1) A). In particular, a mammalian cultured cell used for the recovery of the virus, i.e., 293T cells and Vero cells were separately seeded at $1 \times 10^5$ to $5 \times 10^5$ cells/dish in a 9.4-cm$^2$ culture petri dish, and on the following day, 2 to 5 μg of the plasmid DNA prepared in the above (1) was introduced into these cells using a marketed transfection reagent (FuGENE 6 or Lipofectamine 2000). Culture of the cells was carried out in a Dulbecco Modified Eagle Medium (DMEM) at 37° C. Three days after the addition of the plasmid, one-third of the cells were seeded (subcultured) in a new culture plate. In this subculture, 1 μg/mL Geneticin (G418) (Invitrogen: GIBCO) as a selective drug was added to the Dulbecco Modified Eagle Medium (DMEM). The drug selection allows the survival of only cells into which the target gene was stably introduced. In this way, a G gene stably expressing cell line (G gene stable expression 293T cells and G gene stable expression Vero cells) was isolated.

(3) Recovery of G Gene Deleted Virus

A) Recovery of G Gene Deleted Virus-Infected Vero Cells

The N, P, L, and G genes were introduced as helper plasmids into 293T cells. The P/mGFP ΔG or the p/mGFP ΔG LL prepared in the above was further introduced into the cells (the transfection process is the same as that in the above (2)). The amount of each plasmid introduced into the cells was the N gene=0.25 μg, the P gene=0.025 μg, the L gene=0.25 μg, the G gene=0.01 μg, and the p/mGFP ΔG or the p/mGFP ΔG LL=2.0 μg. After the gene introduction, the 293T cells were cultured at 37° C. Three days after the gene introduction, the cells were subcultured and co-cultured with the G gene stable expression Vero cells prepared in the above. The Vero cells were then recovered as G gene deleted virus-infected Vero cells.

B) Recovery of G Gene Deleted Virus Particles

The infected Vero cells prepared in the above (3) A) were recovered from the culture plate using a trypsin solution (0.03% w/v trypsin and 0.02% w/v EDTA/2Na in PBS-), and the cells were isolated as a cell precipitate by centrifugation at 100 to 150 g and at room temperature for 5 minutes. The recovered cell precipitate was re-suspended in a Modified Eagle Medium (MEM). The prepared suspension was processed using an ultrasonic cell homogenizer. The homogenated suspension was centrifuged at 1000 to 1200 g and at 4° C. for 25 minutes, and the supernatant was recovered as a virus solution. Recombinant BDVs were recovered from the cells in which any of the p/mGFP ΔG and p/mGFP ΔG LL was introduced.

C) Virus Concentration

The virus solution was concentrated as needed using a ultracentrifuge. In particular, a 20% sucrose solution was added to an ultracentrifuge tube, and the virus solution recovered in the above (3) B) was added thereonto. The solution was centrifuged at 50000 to 100000 g and at 4° C. for 2 hours, and the precipitate was re-suspended in PBS- and recovered as a concentrate.

Example 8

Preparation of p/mGFP ΔG LL-Infected Cells and Preparation of Pseudovirus (1) Preparation of p/mGFP ΔG LL-Infected Cell and Confirmation of Persistent Infectivity A) Preparation of p/mGFP ΔG LL-Infected Cells The virus recovered in (3) B) or C) of Examples 7 was inoculated into Vero cells to give p/mGFP ΔG LL-infected cells. In particular, the virus solution was diluted with Opti-MEM (Invitrogen: GIBCO), and a single layer of Vero cells seeded in a 24-well plate was inoculated with 100 μL of the diluted virus solution in Opti-MEM (about 0.1 to 0.01 virus particles per Vero cell) and sensitized at 37° C. for 1 hour. The cells were then washed with PBS- and culturing was continued in a Dulbecco Modified Eagle Medium (DMEM) at 37° C. Since the virus inoculated into the cells is not transmissible to other cells, isolation of 100% infected cells was carried out by cell cloning method (limiting dilution analysis). Confirmation of an infected cell was carried out by observation of the expression of the GFP under a fluorescent microscope. The infected cells isolated here were also used for the preparation of a pseudovirus described below.

The p/mGFP ΔG and the G gene deleted virus-infected Vero cells prepared in Example 7, and the p/mGFP ΔG LL and the p/mGFP ΔG LL-infected cells prepared in the above A), respectively, were used to compare the recombinant BDV production capabilities of the plasmid p/mGFP ΔG and of the p/mGFP ΔG LL. Infection of cells with each of the p/mGFP ΔG and of p/mGFP ΔG LL was carried out by the same manner as in Example 7.

Figures 22, 23, 24:
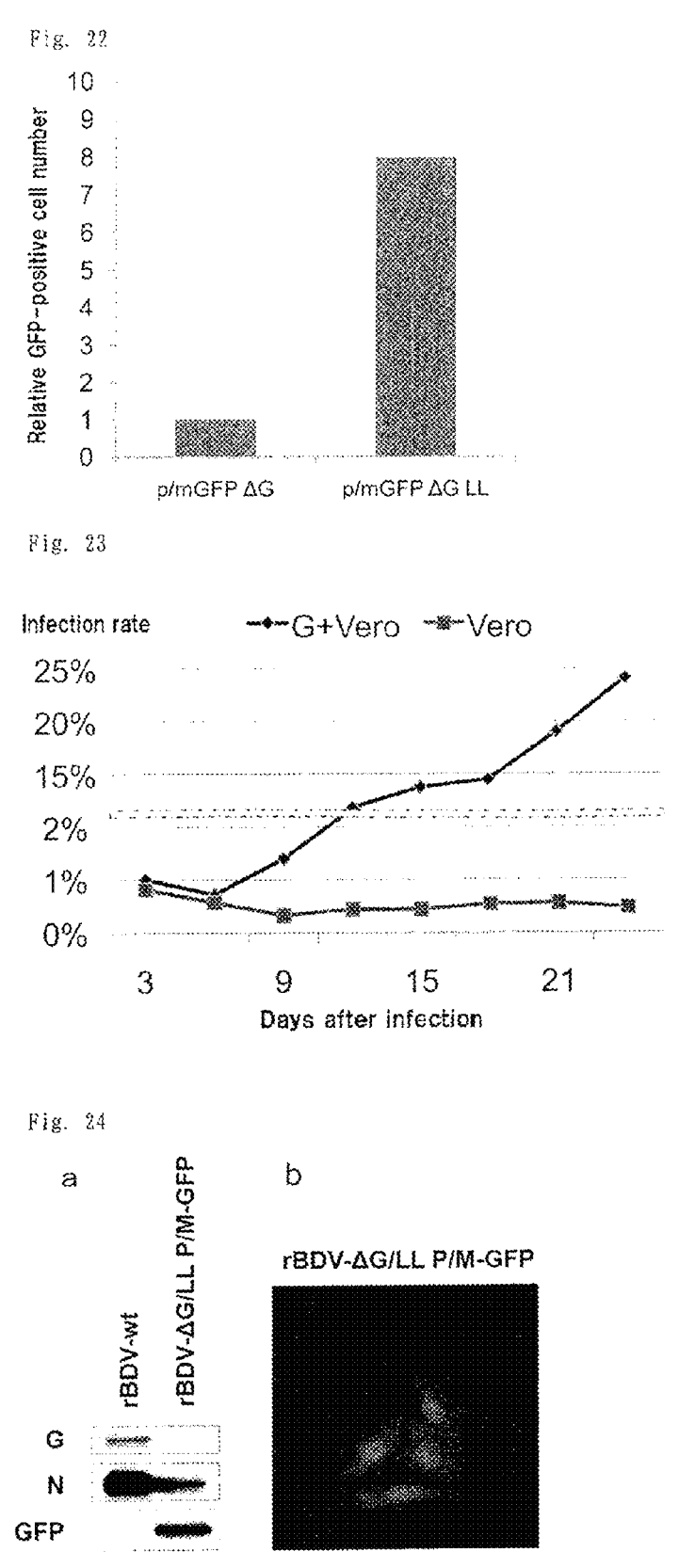

FIG. 22 shows the virus-positive rates measured using the GFP as an indicator on the 12th day after co-culturing with the G gene stably expressing cells. In FIG. 22, the number of the GFP-positive cells per 100,000 cells obtained using the p/mGFP ΔG LL was about 8 times larger than that obtained using the p/mGFP ΔG, when the number of the positive cells obtained using the p/mGFP ΔG is set at 1.

This result revealed that the recombinant BDV production capability of the p/mGFP ΔG LL is higher than that of the p/mGFP ΔG.

B) Persistent infectivity and Transmissibility of p/mGFP ΔG-LL Virus

The virus recovered in (3) B) or C) of Example 7 (the G-deleted recombinant virus) was inoculated into Vero cells or the G gene stable expression Vero cells in a ratio of the virus: the cells=1:100, and the productivity and the persistency were investigated. The infection rate was measured by counting the number of infected cells per 100,000 cells seeded on a 24-well plate. The results show that, as shown in FIG. 23, in cases where the virus was inoculated into Vero cells, the infection rate was maintained at about 1%; however, in cases where the virus was inoculated into the G gene stable expression Vero cells, the infection rate increased with time. This result confirmed that BDV not having the G gene can establish persistent infection in cells (observed for at least 100 days or more), but in order to spread the infection, the G gene is necessary. In FIG. 23, the rhombus symbol represents the BDV G gene stable expression Vero cells and the square symbol represents the Vero cells (cells not expressing the G gene).

FIG. 24a is the results of Western blot for the protein expression in cells infected with the wild-type BDV or the G-deleted recombinant virus. In FIG. 24a, G, N, and GFP represent the G protein, the N protein, and the GFP, respectively. FIG. 24b is a fluorescent photomicrograph of the Vero cells infected with the G-deleted recombinant virus. In FIG. 24b, the part emitting the green fluorescence of the GFP is shown by the gray part. FIGS. 24a and 24b confirmed that in the cell infected with the G gene deleted virus, the GFP that had been introduced by the virus was expressed.

(2) Preparation of Pseudovirus with the Use of p/mGFP ΔG LL Infected Cells

A) Preparation of Chimeric Protein Expression Plasmid Having Intracellular Region of BDV G Gene and Extracellular Region and Transmembrane Region of G Gene of Vesicular Stomatitis Virus (VSV) or Rabies Virus (RabV)

Figures 25, 26, 27:
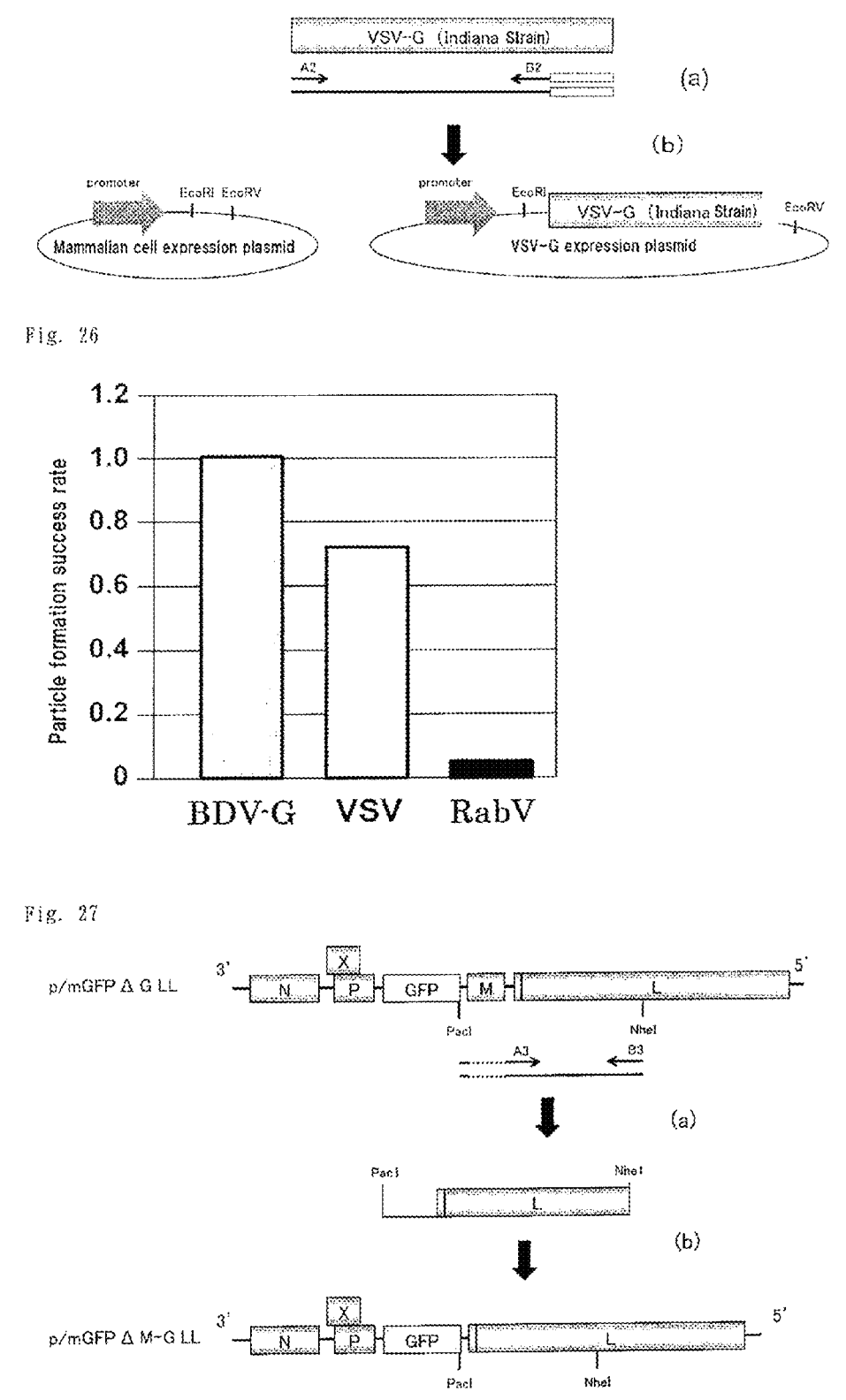

For the purpose of preparing a pseudovirus, a plasmid expressing the membrane protein gene of another virus was prepared. The outline of the procedure is shown in FIG. 25. In particular, with the use of a plasmid expressing the G gene of VSV (Indiana strain) (GenBank ID: J 02428.1) as a template, PCR (25 cycles of 98° C. for 10 seconds, 55° C. for 5 seconds, and 72° C. for 1.5 minutes) was performed using the primers A2 and B2 shown in Table 2 (FIG. 25 (a)). The amplification product (PCR product) was a DNA sequence encoding a chimeric membrane protein having a BDV-derived intracellular region and VSV-derived extracellular and transmembrane regions (hereinafter sometimes referred to as the chimeric VSV-G protein). This PCR product was recombined into the mammalian cell expression plasmid, the pCXN2 (see (1) B) of Example 7), using restriction enzymes EcoRI and EcoRV (FIG. 25 (b)) to give a VSV-G expression plasmid.

A plasmid expressing a chimeric membrane protein derived from BDV and RabV (chimeric Rab-G expression plasmid) was prepared in the same manner as in the above except that a RabV G gene expression plasmid (RabV: Nishigahara strain; GenBank ID: AB044824.1) was used as a template, that the primers C2 and D2 shown in Table 2 were used as the primers instead of the primers A2 and B2, and that restriction enzymes KpnI and EcoRV were used as the restriction enzymes. The Rab-G expression plasmid expresses a chimeric membrane protein having a BDV-derived intracellular region and RabV-derived extracellular and transmembrane regions (hereinafter sometimes referred to as the chimeric Rab-G protein).

TABLE 2

| Primer No. | Sequence |
|---|---|
| A2 | CCGAATTCACCGCCACCATGAAGTGCCTTTTGTACTTAGCC (SEQ ID NO: 22) |
| B2 | GGGATATCTTATTCCTGCCACCGGCCGAGGCGTCTCCTCCTC GCGAGAACCAAGAATAGTCCAATGATTAACCC (SEQ ID NO: 23) |
| C2 | CCGGTACCGCCACCATGGTTCCGCAAGCTCTTCTGCTTGTAC CC (SEQ ID NO: 24) |
| D2 | GGGATATCTTATTCCTGCCACCGGCCGAGGCGTCTCCTCCTC GCACAACATGTCATTAGGAAAATTATCAACATCAAGGC (SEQ ID NO: 25) |

B) Preparation of Chimeric Membrane Protein Stably Expressing Cells

A cell line stably expressing the G gene of VSV or RabV (a VSV-G protein stable expression strain and a Rab-G protein stable expression strain) was prepared. The plasmid prepared in the above (2) A), or a plasmid prepared in the same manner as in the above (2) A) except that the plasmid had been recombined into a Tet system expression plasmid, was used for the preparation of the chimeric membrane protein stably expressing cells. In particular, the expressing cells were prepared in the same manner as in (2) of Example 7 except that the chimeric G protein expression plasmid prepared in the above (2) A), or a plasmid prepared in the same manner as in the above (2) A) except that the plasmid had been recombined into a Tet system expression plasmid, was used instead of the G protein expression plasmid, and that the plasmid was introduced into 293T cells, Vero cells, and the p/mGFP ΔG LL-infected cells prepared in the above (1). The drug resistance concentration and the like of the Tet system were determined according to the attached instruction manual. The Tet system used herein was T-REx system (Invitrogen).

C) Recovery of Pseudovirus

A pseudovirus was recovered using the p/mGFP ΔG LL infected cell clone prepared in the above (1) A). In particular, the p/mGFP ΔG LL-infected cells were transfected with the chimeric membrane protein expression plasmid, and the cells were cultured in a Dulbecco Modified Eagle Medium (DMEM) or in a Nutrient Mixture F-12 HAM culture medium (SIGMA) at 37° C. for 48 to 96 hours. After that, the supernatant was recovered as a pseudovirus containing solution. The recovered pseudovirus had the recombinant BDV genome encoded by the p/mGFP ΔG LL, and was covered with the viral membrane protein of VSV or Rab. FIG. 26 shows the differences in the virus recovery efficiencies (the particle formation success rates) of three different viruses prepared using the G gene of BDV, the coat gene of VSV, or the coat gene of Rab, as the G gene. In FIG. 26, the recovery efficiencies of the viruses are expressed as the relative values when the recovery efficiency of a virus prepared using the G gene of BDV is set at 1.

In the same manner as in Example 7 (3) B) and C), a pseudovirus covered with the membrane protein of VSV or Rab was recovered using chimeric protein expressing cells. Such a pseudovirus has a coat derived from VSV or Rab, and can express the recombinant BDV genome encoded by the p/mGFP ΔG LL.

Example 9

M and G Gene Deleted Virus (1) A plasmid p/mGFP ΔM-G LL, in which the M gene was deleted, was prepared based on the p/mGFP ΔG LL.

A) Construction of p/mGFP ΔM-G LL Plasmid

Figure 29:
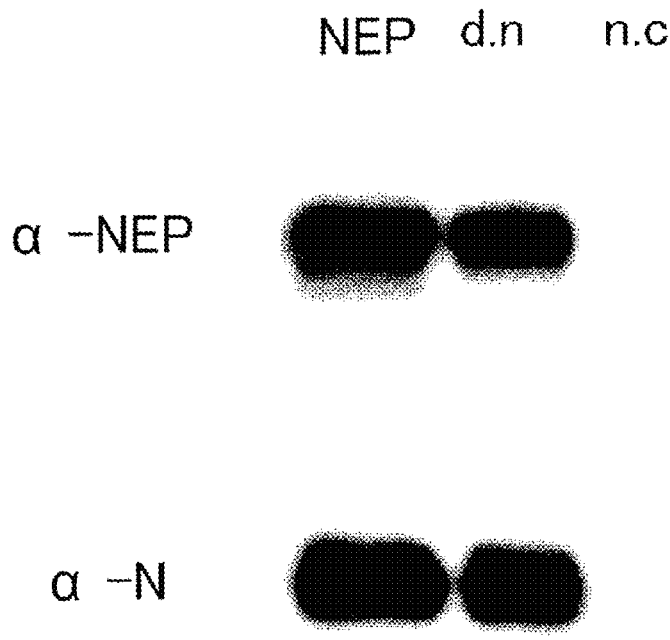

For the purpose of further improving safety and extending the foreign gene insertion site, the M gene, which encodes the membrane scaffold protein of BDV, was deleted. The outline of the preparation procedure for the p/mGFP ΔM-G LL plasmid in which the M gene is deleted is shown in FIG. 27. In particular, with the use of the P/mGFP ΔG LL as a template, PCR (25 cycles of 98° C. for 10 seconds, 55° C. for 5 seconds, and 72° C. for 1.5 minutes) was performed using the primers A3 and B3 shown in Table 3 (FIG. 27 (*a*)). The obtained PCR product (the 1st PCR product) was inserted into the p/mGFP ΔG LL using PacI and NheI to give the p/mGFP ΔM-G LL (FIG. 27 (*b*)).

B) Recovery of p/mGFP ΔM-G LL Virus

In the same manner as the recovery of the p/mGFP ΔG-LL virus in Example 7, a cultured cell line stably expressing both of the M protein and the G protein was prepared (Zeocin was used as the selective drug for the M gene), and a p/mGFP ΔM-G LL virus was recovered.

C) Characteristics Analysis of p/mGFP ΔM-G LL Virus

The obtained p/mGFP ΔM-G LL virus was used to infect Vero cells and, as a result, it was confirmed that the p/mGFP ΔM-G LL virus has the same infectivity as the wild strain.

(2) Preparation of p/mGFP ΔM-G LL P-M Tandem Vector

A foreign gene cassette in which another foreign gene was inserted into the region between the p/m genes of the p/mGFP ΔM-G LL was prepared.

For the purpose of inserting a further foreign gene, a new foreign gene insertion cassette was inserted between the P/M genes. The outline of the preparation procedure of the p/mGFP ΔM-G LL P-M tandem vector is shown in FIG. 28. In particular, with the use of the P/mGFP ΔM-G LL as a template, PCR (25 cycles of 98° C. for 10 seconds, 55° C. for 5 seconds, and 72° C. for 0.5 minutes) was performed using the primers C3 and D3 shown in Table 3 (FIG. 28 (*a*)). With the use of the obtained PCR product (the 1st PCR product) as a template, PCR (25 cycles of 98° C. for 10 seconds, 98° C. for 5 seconds, and 72° C. for 0.5 minutes) was further performed using the primers C3 and E3 (Table 3) (FIG. 28 (*b*)). The obtained PCR product (the 2nd PCR product) was inserted into the p/mGFP ΔM-G LL using EcoT22I and BstBI. In this way, insertion of a new foreign gene insertion cassette, Sse8381 I-SwaI, into the p/mGFP ΔM-G LL was achieved, and thus the p/mGFP ΔM-G LL P-M tandem vector was obtained.

This cassette can be recombined using EcoT22I and BstBI into other p/m vectors having a BstBI-PacI site between the ORF of the P gene and the ORF of the M gene.

TABLE 3

| Primer No. | Sequence |
|---|---|
| A3 | GTAATTAATTAACCATAAAAAAATCGAATCACCATGTCATTTCATGCGAGCCTCCTTCGCGAGGAGGAGACGC (SEQ ID NO: 26) |
| B3 | GGGTCTGCAAGAGTGCTAGCTGAAAGGGC (SEQ ID NO: 27) |

TABLE 3-continued

| Primer No. | Sequence |
|---|---|
| C3 | GGAATGCATTGACCCAACCGGTAGACCAGC (SEQ ID NO: 28) |
| D3 | ATTTAAATGGTTGGCCTGCAGGGGTGATTCGATTTTTTTATGG (SEQ ID NO: 29) |
| E3 | AAGGTTCGAAGGTGATTCGATTTTTTTATGGTATTTAAATGGTTGGCCTGCAGGGGTGATTCG (SEQ ID NO: 30) |

Example 10

Use of p/m Vector (1) Preparation of p/mNEP Vector for Treatment for Alzheimer's Disease A) Preparation of p/mNEP Vector For the purpose of developing a gene therapy for Alzheimer's disease, prepared was a p/mNEP vector in which an amyloid-β-protein (Aβ) degradative enzyme, Neprilysin (NEP: Gene ID=4311), was inserted into the region between the p/m genes. In particular, RNA was extracted from a human-derived cultured cell, and reverse transcription reaction of mRNA was performed using oligodT as a primer and a reverse transcriptase (Invitrogen, Super script III). With the use of the obtained cDNA as a template, NEP was amplified by PCR (25 cycles of 98° C. for 10 seconds, 55° C. for 5 seconds, and 72° C. for 2.5 minutes) using the primers A4 and B4 shown in Table 6. The obtained PCR product was recombined into the p/mGEP vector using BstBI-PacI to give a p/mNFP vector. In the p/mNEP vector, the cDNA of the GFP in the plasmid having the inserted GFP between the BDV P-M genes (p/mGFP), prepared Example 1, was replaced with the cDNA of NEP. As a comparison, prepared was a recombinant p/m vector into which a mutated NEP enzyme active site was inserted (hereinafter referred to as the reference vector 1). In particular, with the use of the p/mNEP as a template, PCRs (25 cycles of 98° C. for 10 seconds, 55° C. for 5 seconds, and 72° C. for 2 or 0.5 minutes) were performed using the primers A4 and C4, as well as using the primers B4 and D4 shown in Table 6. Next, with the use of the amplification products (the 1st PCR products) as a template, PCR (25 cycles of 98° C. for 10 seconds, 55° C. for 5 seconds, and 72° C. for 2.5 minutes) was performed using the primers A4 and B4. In the amplification product (the 2nd PCR product), glutamic acid (GAA), the 585th residue in the amino acid sequence of NEP, is replaced with valine (GtA). This amplification product was recombined into the p/mNEP vector using BstBI-PacI to give the reference vector 1.

Recombinant viruses were recovered from each of the prepared p/mNEP vector and the reference vector 1 in the same manner as in Example 2, and used for characteristics analysis. The recovered viruses were also administered to an Alzheimer's disease model mouse.

B) p/mNEP Expression and Activity Measurement in Vero Cells

With the use of the p/mNEP vector prepared in the above, p/mNEP-infected Vero cells were obtained in the same manner as in Example 2.

Western Blotting and indirect immunofluorescence were performed to confirm whether the obtained p/mNEP-infected Vero cells in fact express NEP. The primary antibody used here was an anti-CD10 [56C6] mouse monoclonal antibody (Abcam: ab951). FIG. 29 shows the results of the Western blotting for the p/mNEP-infected cells. In FIG. 29, NEP represents the cells infected with the recombinant virus p/mNEP produced from the p/mNEP vector, d.n represents reference cells infected with the virus produced from the reference vector 1, n.c represents uninfected cells, and α-N represents the N protein of BDV. From FIG. 29, it was confirmed that NEP was expressed both in the cells infected with the recombinant virus produced from the p/mNEP vector and in the cells infected with the recombinant virus produced from the reference vector 1 (reference cell 1).

Figure 30:
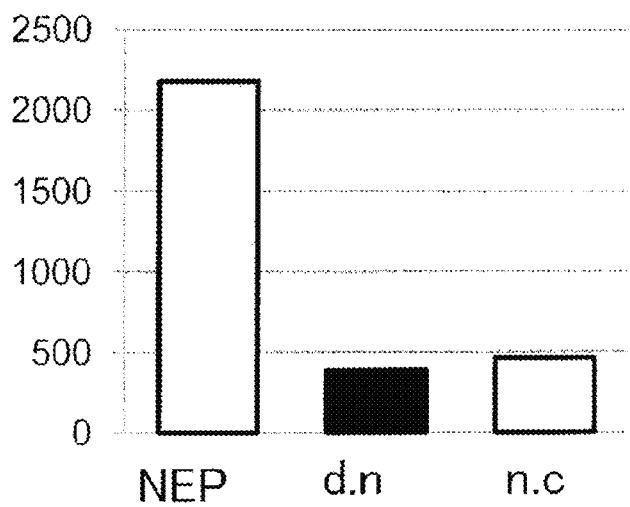

For the activity measurement of NEP, DAGNPG (Sigma), which is a synthetic mimic of the reaction site for NEP, was used. First, the p/mNEP-infected cells were dissociated from a culture petri dish with trypsin, and recovered by centrifugation. The recovered cells were re-suspended in a solution containing DAGNPG (50 mM Tris-HCl, 1 μM captopril, and 50 μM DAGNPG), and reacted at 37° C. for 2 hours. After the reaction, the solution was heated at 100° C. for 5 minutes for deactivation of the enzyme. The solution was then centrifuged at about 15000 g and at 4° C. for 5 minutes, and the supernatant was recovered. The recovered solution was placed at 200 per well into a 96-well plate. The solution was excited with an excitation wavelength of 342 nm and the luminescence was read with a microplate reader at a wavelength of 580 nm. As the NEP activity is stronger, the amount of detected luminescence increases. The measurement results of the cutting enzyme activity are shown in FIG. 30. The NEP activity in the p/mNEP-infected cells was significantly higher than those in uninfected cells and in the reference cells 1.

D) Persistency of Recombinant Virus Produced from p/mGFP Vector in Brain

Figure 18:
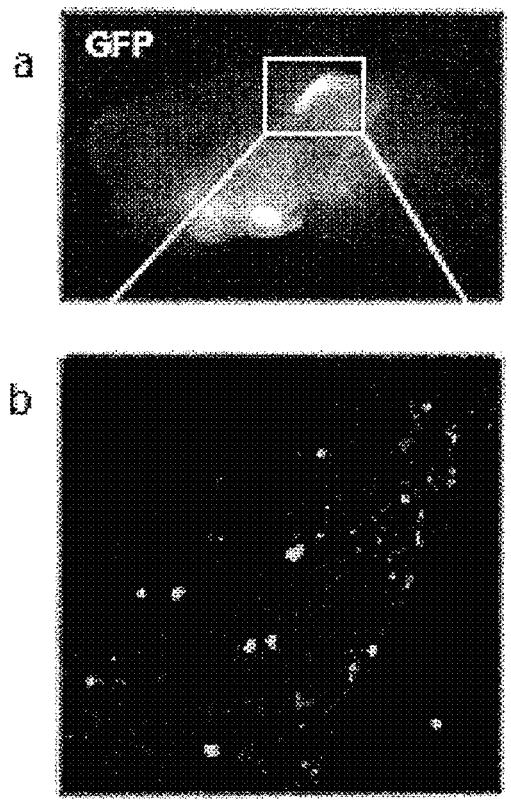
Figure 19:
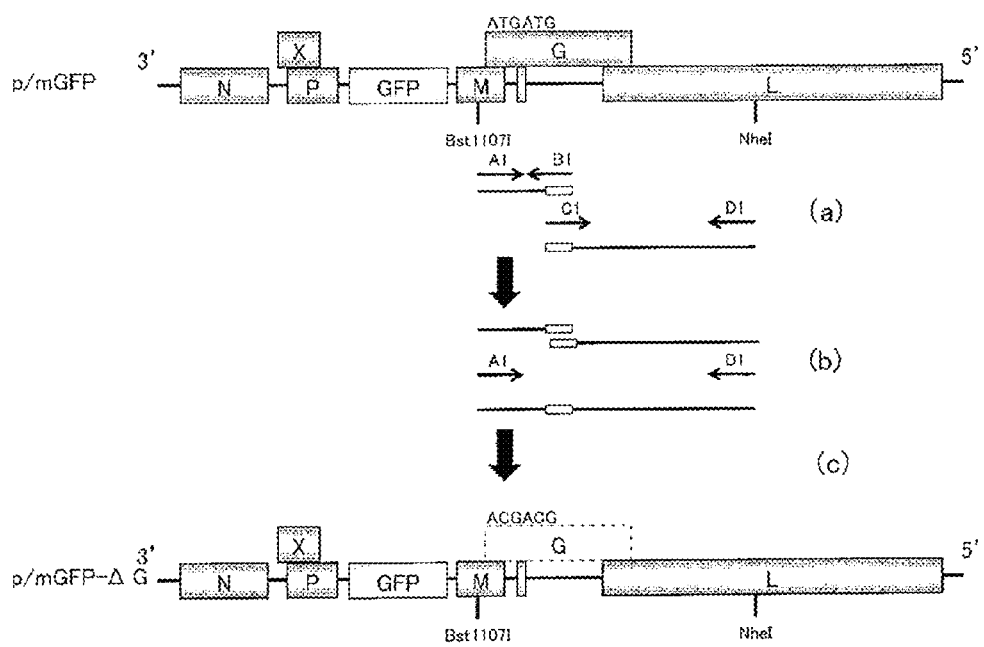
Figure 20:
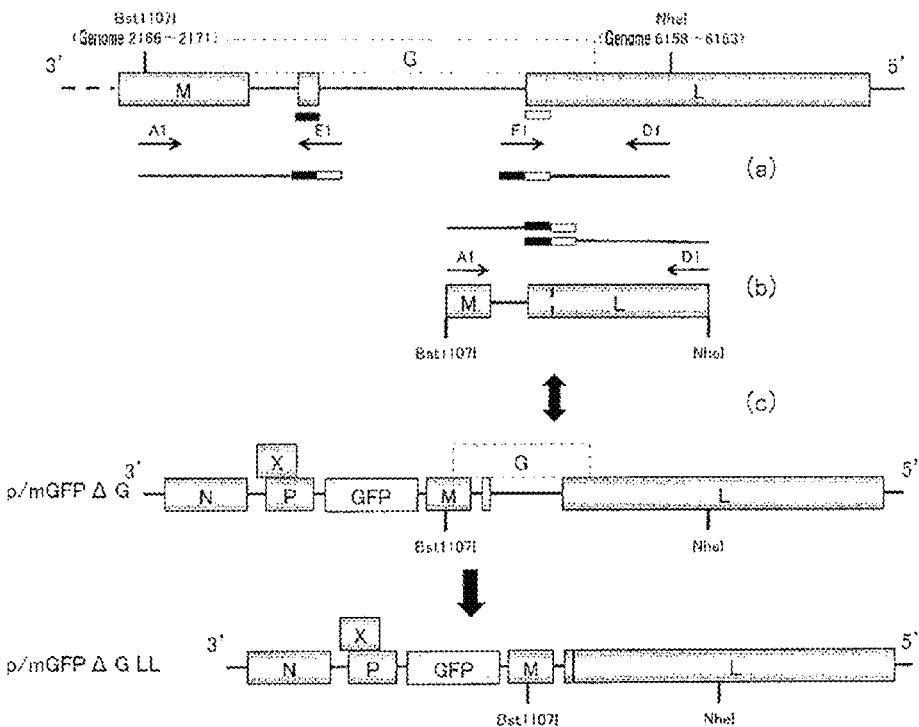

It was confirmed at this point that the expression of the introduced GFP in the brain of the mice inoculated with the recombinant virus produced from the p/mGFP vector lasted for at least 8 months after the inoculation (Example 6 and FIG. 18). From this result, the p/m vector is considered to be applicable to neurological diseases having a prolonged course, for example, Alzheimer's disease or the like.

Example 11

(1) Development of miRNA Introducing Vector

In view of application to medical care and research, a p/m vector capable of introducing a miRNA, which is a functional RNA, was prepared.

A) Preparation of p/m miR155 Introducing Vector (pSIRIUS-B)

Figure 31:
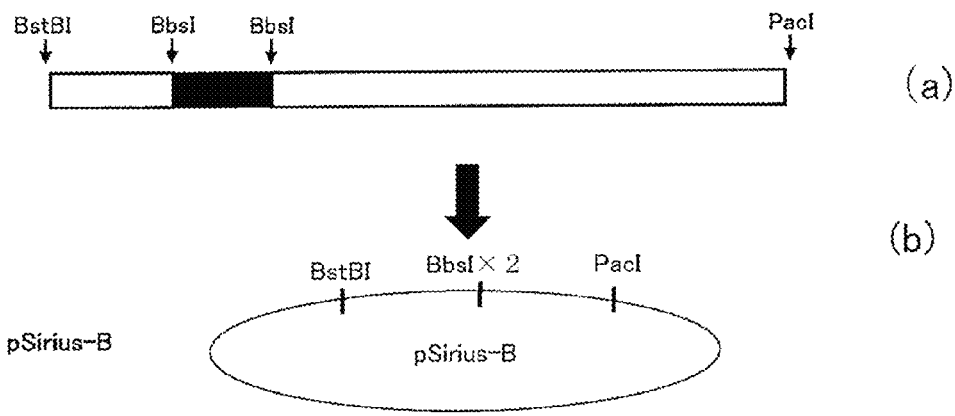
FIG. 31 is a schematic view of the preparation procedure of a p/m miR155 transfer vector (pSIRIUS-B).

The outline of the preparation procedure of pSIRIUS-B is shown in FIG. 31. An introducing vector required to introduce various miRNA sequences was prepared. First, the cleavage sites of BstBI and PacI were introduced into the multi-cloning site of pBluescript SK- (FIG. 31 (*b*)), and a p/m miR155 introducing vector, pSIRIUS-B, was obtained. Next, a miR155-based designed control sequence required to express a miRNA was introduced between the BstBI and Pad sites. A BbsI-digested cassette was inserted into the center between the BstBI and PacI sites so that various miRNA sequences could be introduced (FIG. 31 (*a*)).

In the schematic view of FIG. 31 (*a*), the white part is a control region for miRNA expression, and the black part is the oligo introduction cassette. The sequence of the DNA fragment schematically shown in FIG. 31 (*a*) and the cleavage sites in the sequence are shown in Table 4 below.

TABLE 4

(SEQ ID NO: 31)

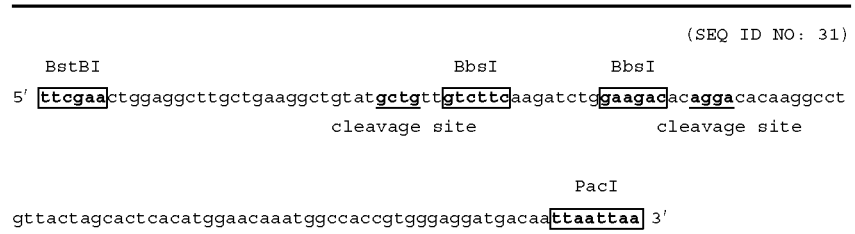

C) Inoculation of p/mNEP into Alzheimer's Disease Model Mouse

In view of developing a therapy for the disease, first, p/mNEP was inoculated into a Alzheimer's disease model mouse. Among various kinds of Alzheimer's disease model mice, B6SJL-Tg (APPSwFlLon, PSEN1*M146L*L286V) 6799Vas/J (Jackson laboratory No. 6554) and B6.Cg-Tg (APPSwe, PSEN1dE9) 85 Dbo/J (Jackson laboratory No. 5864) were used in this experiment. In these model mice, a human Aβ precursor protein and the mutant of the degradative enzyme thereof, presenilin, are expressed in neurons, and these model mice have been reported to develop the Alzheimer's disease-like symptoms in the early postnatal period.

Into the brain of the above neonatal model mice, the recombinant virus produced from the p/mNEP vector was inoculated.

B) Preparation of Vector for Activity Measurement Using p/m miR155

Figure 32:
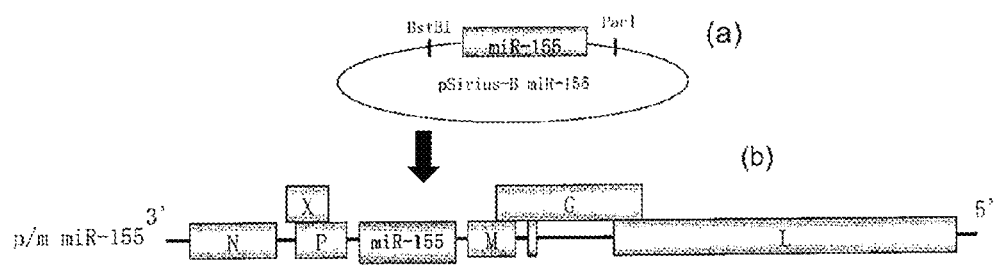
FIG. 32 is a schematic view of the preparation procedure of a plasmid p/m miR155.

With the use of the vector prepared in A) together with BstBI and PacI, various miRNA sequences can be inserted into the p/m vector. miR155 was used as an example here. A miR155 target sequence was synthesized, and this sequence was inserted using BbsI into pSIRIUS-B to give pSirius-B miR-155 (FIG. 32 (*a*)). The sequence of the miR155 target sequence synthesized herein is shown in Table 5. The upper row is the sequence of miRNA155 (SEQ ID NO: 32). The sequence in the lower row in Table 5 is shown in SEQ ID NO: 33. The miR155 target sequence (oligo) in the pSirius-B miR-155 was inserted using BstBI-PacI into the p/m vector to give p/m miR155 (FIG. 32 (*b*)).

TABLE 5

| GCTG | TTAATGCTAATTGTGATAGGGG | TTTTGGCCTCTGACTGA | CTCCTACCTGTTAGCATTAAC | |
|---|---|---|---|---|
| | AATTACGATTAACACTATCCCC | AAAACCGGAGACTGACT | GAGGATGGACAATCGTAATTG | AGGA |
| | Target Sequence | miR-155 loop | complementary strand Sequence | |

Further, for the purpose of investigating whether the introduced miR155 functions, a plasmid into which the miR155 target sequence was introduced downstream of a reporter gene luciferase was prepared so that the effect of miR155 could be judged.

C) Recovery and Activity Measurement of p/m miR155

Figures 33, 34, 35:
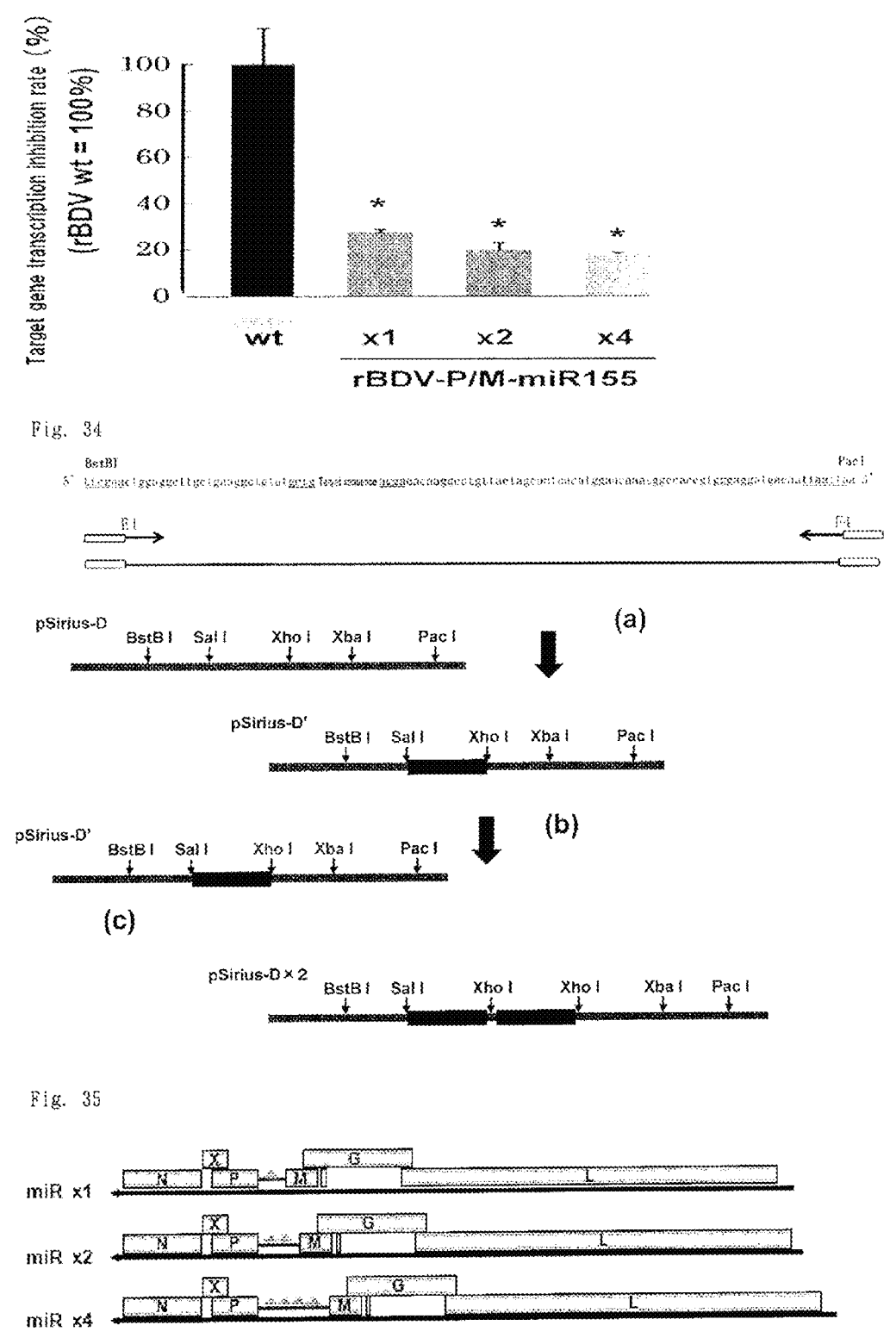

In the same manner as in Example 2, a recombinant virus was recovered from the p/m miR155 plasmid, and the activity of the recombinant virus was measured using the plasmid prepared in B). In particular, a reporter plasmid was introduced using a transfection reagent (Lipofectamine 2000 or the like) into p/m miR155-infected cells and into wild-type BDV strain-infected cells (both cells were obtained by infecting Vero cells with the viruses). Two to three days later, experiments were carried out according to the protocol attached to Luciferase Assay System (Promega), and the activity in the p/m miR155-infected cells was compared with that in the wild-type BDV strain-infected cells. The transcription inhibition rates of the target gene in cells infected with the recombinant virus are shown in FIG. 33 (wt: wild-type BDV strain-infected cells, and ×1: p/m miR155-infected cells).

D) Preparation of p/m miR×2 and p/m miR×4

A new plasmid for insertion of miRNA×2 (a twice-repeated sequence) or miRNA×4 (a 4 time-repeated sequence) was prepared by modifying a). The outline of the preparation procedure is shown in FIG. 34. First, BstBI and PacI were inserted into the multi-cloning site of pcDNA3 (pSIRIUS-D). Next, with the use of the plasmid prepared in A) (in which the target miRNA had been inserted) as a template, PCR (25 cycles of 98° C. for 10 seconds, 55° C. for 5 seconds, and 72° C. for 0.5 minutes) was performed using the primers E4 and F4 shown in Table 6. The obtained PCR product was inserted using SalI and XhoI into pSIRIUS-D (FIG. 34 (*a*)) (caution was taken in the insertion direction). From the prepared plasmid, the insert was cut out using SalI and XbaI (FIG. 34 (*b*)), and the obtained fragment was inserted into the same (but intact) plasmid using XhoI and XbaI (SalI and XbaI have the same cutting sequence) (FIG. 34 (*c*)). Thus a plasmid having miRNA×2 was obtained. The obtained miRNA×2 plasmid was cut out using EstBI and PacI and inserted into the p/m vector to give a p/m miRNA×2. A miRNA×4 was prepared by repeating the above steps. The schematic views of the miRNA×2 and miRNA×4 p/m vectors are shown in FIG. 35. From the obtained miRNA×2 and miRNA×4 p/m vectors, recombinant viruses were recovered in the same manner as in Example 2, and the effects of thereof were investigated. The results are shown in FIG. 33. In FIG. 33, ×1, ×2, and ×4 represent the number of miR155 inserted into the plasmid. As is apparent from FIG. 33, as the number of the introduced miR155 was greater, the expression of the target gene was more efficiently inhibited. In addition, it was confirmed that the miR155 introduced into the cells can be persistently expressed in the cells, which reveals that the vector of the present invention is useful as an RNA vector expressing a functional RNA.

TABLE 6

| Primer No. | Sequence |
|---|---|
| A4 | GGTCTTCGAAATGGGCAAGTCAGAAAGTCAGATGG (SEQ ID NO: 34) |
| B4 | GTGCAGTTAATTAATCACCAAACCCGGCACTTCTTTTCTGG (SEQ ID NO: 35) |
| C4 | ATTACGTGTCCTATGACCATGCCGATG (SEQ ID NO: 36) |
| D4 | CGTAATCACCCATGGCTTCGATGAC (SEQ ID NO: 37) |
| E4 | GCGGAAATTCGTCGACCTGGAGGCTTGCTGAAGG (SEQ ID NO: 38) |
| F4 | CGCTCTAGACTCGAGTTGTCATCCTCCCACGGTG (SEQ ID NO: 39) |
| G4 | CTGGCCTGCTGGCTGAACCC (SEQ ID NO: 44) |
| H4 | GCCCCGCTTGCACCAGTTCT (SEQ ID NO: 45) |

(2) Application of miRNA Introducing Vector

Figures 36, 37:
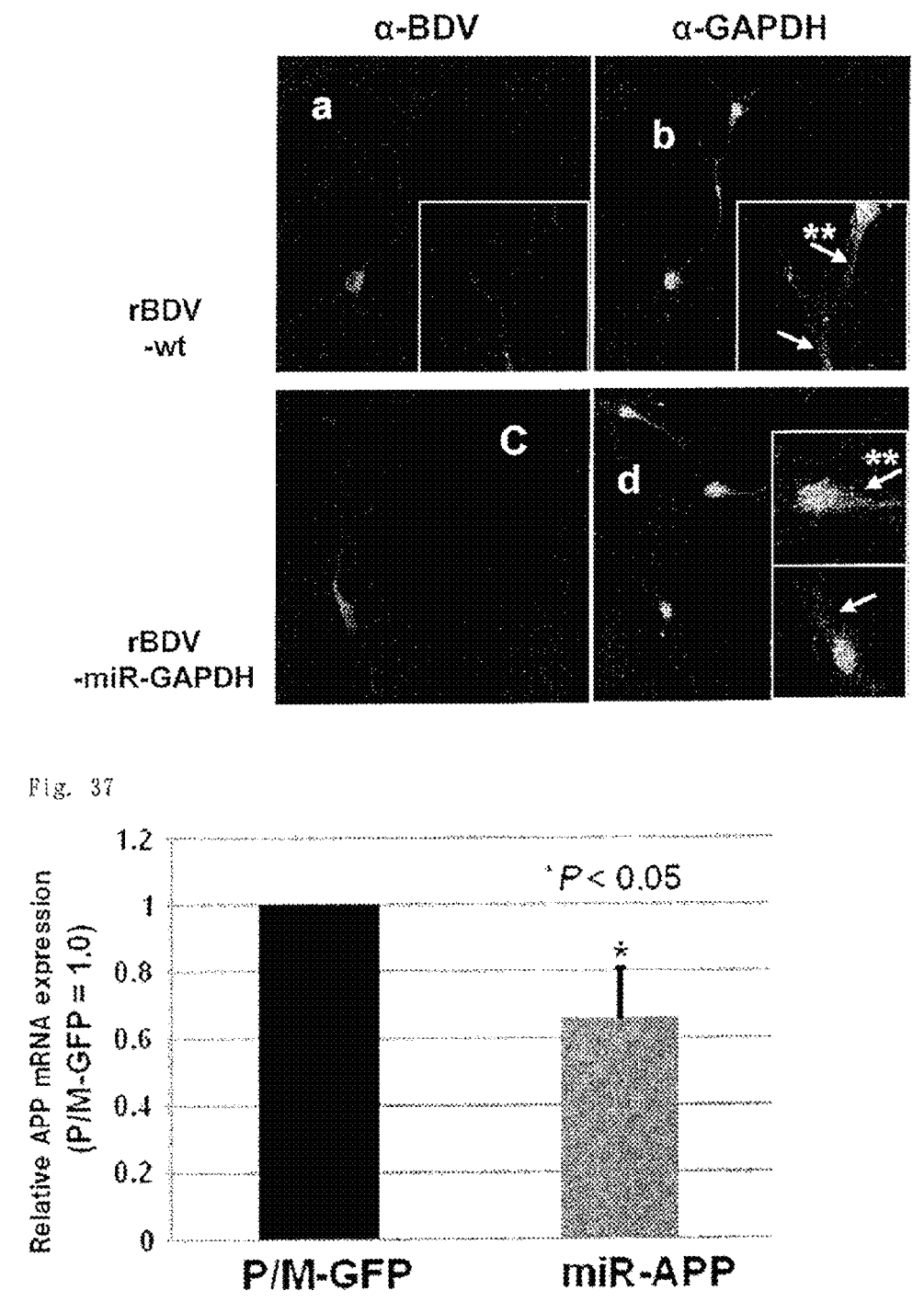

A) Effect of miRNA in Primary Cultured Mouse Hippocampal Cells Using p/m miRNA GAPDH In the same manner as in the preparation of the p/m miRNA155, a miRNA for GAPDH (miR-GAPDH), which is constantly expressed in a cell, was inserted instead of miRNA155 to give a plasmid (p/m miRNA-GAPDH), and the effect of the p/m miRNA-GAPDH was investigated using primary cultured mouse hippocampal cells, whose characteristics are close to those of a living body. The preparation method for the p/m miRNA-GAPDH is similar to that for the p/m miR155 described in (1) (the sequence of the synthesized miR-GAPDH is shown in SEQ ID NOs: 40 and 41). The DNAs of SEQ ID NOs: 40 and 41 form a double strand in the plasmid. In the same manner as in Example 2, the recombinant virus p/m miRNA-GAPDH produced from the p/m miRNA-GAPDH was recovered. The recovered recombinant virus p/m miRNA-GAPDH was inoculated at a MOI=0.01 into the primary cultured cells harvested from the hippocampus of a neonatal mouse. Seven days later, the cells were fixed, stained with an anti-BDV N antibody and an anti-GAPDH antibody, and observed under a fluorescent microscope. The observation revealed that the expression of GAPDH was more significantly inhibited in the cell infected with the recombinant virus p/m miR-GAPDH than that in the cells infected with a wild-type BDV (FIG. 36). FIGS. 36*a* and 36*b* show the cells infected with the wild-type BDV, and FIGS. 36*c* and 36*d* show the cells infected with the recombinant virus p/m miR-GAPDH. FIGS. 36*a* and 36*c* are the fluorescent photomicrographs of the cells stained with an anti-BDV N antibody, and FIGS. 36*b* and 36*d* are the fluorescent photomicrographs of the cells stained with an anti- GAPDH antibody. The photographs enclosed by the squares in FIGS. 36*b* and 36*d* are enlarged photographs, and the arrow with  indicates uninfected cells. The arrow without  indicates the infected cells (the wild type in FIG. 36*b*, and p/m miR-GAPDH in FIG. 36*d*). It was observed that in FIG. 36*b* the expression level of GAPDH was high both in the uninfected cells and in the infected cells (GAPDH was not inhibited), while in FIG. 36*d* the expression of GAPDH was inhibited more in the infected cells than in the uninfected cells.

B) Effect of miRNA-APP in Infected Vero Cells Using p/m miRNA APP

In the same manner as in the preparation of the p/m miRNA155, a miRNA for APP (miRNA-APP), which is a protein that causes Alzheimer's disease, was inserted instead of the miRNA155 to give a plasmid (p/m miRNA-APP), and the effect of the p/m miRNA-APP was investigated using p/m miRNA-APP-infected Vero cells. The preparation method for the p/m miRNA-APP is similar to the preparation method for the p/m miR155 described in (1) (the sequence of the synthesized p/m miRNA-APP is shown in SEQ ID NOs: 42 and 43). The DNAs of SEQ ID NOs: 42 and 43 form a double strand in the plasmid. In the same manner as in Example 2, the recombinant virus p/m miRNA-APP produced from the p/m miRNA-APP was recovered. The recovered recombinant virus p/m miRNA-APP was used to infect cells, and an APP expression plasmid (prepared according to the attached instruction manual of pcDNA3; the cDNA of APP (Accession No.=NM_000484) was prepared from RNA extracted from an a human-derived cultured cell using an oligo dT primer and a reverse transcriptase.) was introduced into the infected cells using Lipofectamine 2000 according to the attached instruction manual. 48 hours later, RNA was recovered, and the mRNA level of APP was measured by quantitative RT-PCR (40 cycles of 95° C. for 10 seconds and 60° C. for 30 seconds) using the APP-specific primers G4 and H4 shown in the above Table 6. As a control, the same experiment was conducted using cells infected with the recombinant virus produced from the p/mGFP. The results revealed that the amount of the mRNA of APP in the Vero cells infected with the recombinant virus p/m miRNA-APP was significantly reduced compared with that in the Vero cells infected with the p/mGFP (FIG. 37).

INDUSTRIAL APPLICABILITY

The recombinant virus produced from the viral vector of the present invention can noncytotoxically and efficiently express a foreign gene in the cell nucleus. In addition, the viral vector, which contains a RNA viral genome, is a safe vector that is not integrated into a host chromosome. Further, since the viral vector of the present invention utilizes Borna disease virus, which is a neurotropic virus, the viral vector has an excellent specificity that allows selective introduction of a foreign gene into a cranial nerve system. Thus, the present invention can be applied, as a gene transfer technique not affecting a host chromosome, to various fields such as the treatment and prevention of cranial nerve diseases, and a visualization technique of nerve system cells in the field of neuroscience, and therefore the present invention is useful. The present invention can also be applied to a technique for a vector stably expressing a functional RNA such as an siRNA, a miRNA, and an RNA aptamer. Therefore, the present invention is useful in fields such as medical care, animal medical care, clinical trials, and research.

The invention claimed is:

1. A viral vector comprising:

(a) a cDNA of a recombinant viral RNA having at least the N gene, the X gene, the P gene, and the L gene of a Borna disease virus genome in the same order as that in the Borna disease virus genome, having a sequence in which a foreign gene is inserted into the untranslated region connected to the downstream of the open reading frame of the P gene, containing restriction enzyme sites both at the 3' end and at the 5' end of the foreign gene, containing the sequence shown in SEQ ID NO: 11 (1) both in the region between the restriction enzyme site at the 3' end of the foreign gene and the open reading frame of the P gene and in the region between the restriction enzyme site at the 5' end of the foreign gene and the open reading frame of the L gene, or (2) both in the region between the restriction enzyme site at the 3' end of the foreign gene and the open reading frame of the P gene and the region between the restriction enzyme site at the 5' end of the foreign gene and the open reading frame of the M gene when the M gene of the Borna disease viral genome is contained in the same order as that in the Borna disease viral genome, and containing at least a base sequence cc inserted in the region between the restriction enzyme site at the 3' end of the foreign gene and the sequence shown in SEQ ID NO: 11, and at least a base sequence cca in the region between the restriction enzyme site at the 5' end of the foreign gene and the sequence shown in SEQ ID NO: 11, (b) a DNA encoding a ribozyme, and (c) a promoter sequence, each being disposed in a position in which (b) is placed upstream and downstream of (a), and (a) and (b) are placed downstream of (c), wherein (a) the cDNA of a recombinant viral RNA has a sequence in which the G gene and the M gene of the Borna disease virus genome are destructed and has a sequence in which a foreign gene is inserted into the untranslated region connected to the downstream of the open reading frame of the P gene, and wherein an intron of the L gene of the Borna disease virus genome is deleted from (a) the cDNA of a recombinant viral RNA.

2. The viral vector according to claim 1, wherein the restriction enzyme site at the 3' end of the foreign gene is a Bst BI site, and the restriction enzyme site at the 5' end of the foreign gene is a Pac I site.

3. The viral vector according to claim 1, wherein (c) the promoter sequence is an RNA polymerase II promoter sequence.

4. A kit comprising the viral vector according to claim 1.

5. The viral vector according to claim 1, wherein the foreign gene expresses a functional RNA.

* * * * *